United States Patent
Burns et al.

(10) Patent No.: US 9,029,386 B2
(45) Date of Patent: May 12, 2015

(54) PYRIDINE DERIVATIVES USEFUL AS KINASE INHIBITORS

(71) Applicant: YM Biosciences Australia Pty Ltd, Melbourne (AU)

(72) Inventors: Christopher John Burns, Richmond (AU); Michael Francis Harte, Viewbank (AU); James T. Palmer, Templestowe (AU)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/747,343

(22) Filed: Jan. 22, 2013

(65) Prior Publication Data

US 2013/0137660 A1 May 30, 2013

Related U.S. Application Data

(63) Continuation of application No. 12/515,250, filed as application No. PCT/AU2007/001761 on Nov. 15, 2007, now Pat. No. 8,461,161.

(60) Provisional application No. 60/901,512, filed on Feb. 14, 2007.

(30) Foreign Application Priority Data

Nov. 15, 2006  (AU) ................ 2006906359

(51) Int. Cl.
| | |
|---|---|
| A61K 31/435 | (2006.01) |
| C07D 213/74 | (2006.01) |
| C07D 241/20 | (2006.01) |
| C07D 213/75 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| C07D 409/14 | (2006.01) |
| C07D 413/12 | (2006.01) |
| C07D 417/12 | (2006.01) |
| C07D 213/82 | (2006.01) |
| C07D 241/18 | (2006.01) |
| C07D 241/24 | (2006.01) |
| C07D 241/28 | (2006.01) |
| C07D 405/12 | (2006.01) |
| C07D 405/14 | (2006.01) |
| C07F 9/6558 | (2006.01) |

(52) U.S. Cl.
CPC ............ *C07D 241/20* (2013.01); *C07D 213/75* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 409/14* (2013.01); *C07D 413/12* (2013.01); *C07D 417/12* (2013.01); *C07D 213/82* (2013.01); *C07D 241/18* (2013.01); *C07D 241/24* (2013.01); *C07D 241/28* (2013.01); *C07D 405/12* (2013.01); *C07D 405/14* (2013.01); *C07F 9/65583* (2013.01)

(58) Field of Classification Search
CPC ........................... A61K 31/435; C07D 213/74
USPC .......................................... 514/277; 546/304
See application file for complete search history.

(56) References Cited

U.S. PATENT DOCUMENTS

| | | | |
|---|---|---|---|
| 5,093,340 | A | 3/1992 | Mohrs et al. |
| 5,874,451 | A | 2/1999 | Glombik et al. |
| 6,001,879 | A | 12/1999 | Seitz et al. |
| 6,143,780 | A | 11/2000 | Brouwer et al. |
| 6,635,641 | B2 | 10/2003 | Bender et al. |
| 7,122,550 | B2 | 10/2006 | Burns et al. |
| 7,259,179 | B2 | 8/2007 | Burns et al. |
| 7,511,047 | B2 | 3/2009 | Burns et al. |

(Continued)

FOREIGN PATENT DOCUMENTS

| | | |
|---|---|---|
| EP | 1 522 314 A1 | 4/2005 |
| GB | 2 011 892 A | 7/1979 |

(Continued)

OTHER PUBLICATIONS

Purandare et al. (2005). "Identification of Chemokine Receptor CCR4 Antagonist," *Bioorganic & Medicinal Chemistry Letters* 15:2669-2672.

(Continued)

*Primary Examiner* — Douglas M Willis
(74) *Attorney, Agent, or Firm* — Yu-Ming Dammann; Brian Lewis

(57) ABSTRACT

Derivatives of pyridine of the formula

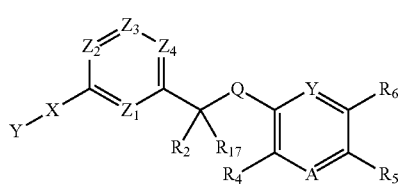

wherein one of Y and A is CR and the other is N are kinase inhibitors useful in treating conditions associated with excess kinase activity.

16 Claims, 2 Drawing Sheets

(56) References Cited

U.S. PATENT DOCUMENTS

| | | |
|---|---|---|
| 7,598,272 B2 | 10/2009 | Burns et al. |
| 8,084,456 B2 | 12/2011 | Burns et al. |
| 8,461,161 B2 | 6/2013 | Burns et al. |
| 2002/0120011 A1 | 8/2002 | Sikorski et al. |
| 2004/0235862 A1 | 11/2004 | Burns et al. |
| 2007/0161635 A1 | 7/2007 | Burns et al. |
| 2007/0191370 A1 | 8/2007 | Devasagayaraj et al. |

FOREIGN PATENT DOCUMENTS

| | | |
|---|---|---|
| JP | 63-93765 A | 4/1988 |
| JP | 09-268169 A | 10/1997 |
| JP | 10-287651 A | 10/1998 |
| JP | 10-513442 A | 12/1998 |
| JP | 11-130750 A | 5/1999 |
| JP | 2004-502635 A | 1/2004 |
| JP | 2005-501821 A | 1/2005 |
| JP | 2005-538975 A | 12/2005 |
| JP | 2006-111553 A | 4/2006 |
| JP | 2009-523812 A | 6/2009 |
| WO | WO-96/23783 A1 | 8/1996 |
| WO | WO-97/03967 A1 | 2/1997 |
| WO | WO-97/08135 A1 | 3/1997 |
| WO | WO-01/23357 A2 | 4/2001 |
| WO | WO-01/23357 A3 | 4/2001 |
| WO | WO-01/53274 A1 | 7/2001 |
| WO | WO-03/000666 A1 | 1/2003 |
| WO | WO-03/099796 A1 | 12/2003 |
| WO | WO-2004/004720 A1 | 1/2004 |
| WO | WO-2004/006858 A2 | 1/2004 |
| WO | WO-2004/052868 A1 | 6/2004 |
| WO | WO 2005/002673 * | 1/2005 |
| WO | WO-2005/002673 A1 | 1/2005 |
| WO | WO-2005/013982 A1 | 2/2005 |
| WO | WO-2005/054199 A1 | 6/2005 |
| WO | WO-2005/066156 A1 | 7/2005 |
| WO | WO 2006/010637 * | 2/2006 |
| WO | WO-2006/010637 A2 | 2/2006 |
| WO | WO-2006/010637 A3 | 2/2006 |
| WO | WO-2006/010637 A8 | 2/2006 |
| WO | WO 2006/065204 * | 6/2006 |
| WO | WO 2006/074428 * | 7/2006 |
| WO | WO-2007/084667 A2 | 7/2007 |
| WO | WO-2007/084667 A3 | 7/2007 |
| WO | WO-2008/058341 A1 | 5/2008 |

OTHER PUBLICATIONS

Tümer, M. et al. (1999). "Antimicrobial Activity Studies of the Binuclear Metal Complexes Derived from Tridentate Schiff Base Ligands," *Transition Metal Chemistry* 24:414-420.

International Search Report mailed on Jan. 9, 2008, for PCT Patent Application No. PCT/AU2007/001761, filed on Nov. 15, 2007, 2 pages.

Hartwig, J.F. (1998). "Transition Metal Catalyzed Synthesis of Arylamines and Aryl Ethers from Aryl Halides and Triflates: Scope and Mechanism," *Angew. Chem. Int. Ed.* 37:2046-2067.

Kumada, M. et al. (1988). "Phosphine-Nickel Complex Catalyzed Cross-Coupling of Grignard Reagents with Aryl and Alkenyl Halides: 1,2-Dibutylbenzene," *Organic Syntheses Collective* vol. 6, pp. 407-411.

March, J. (1992). "Aliphatic Nucleophilic Substitution," *in Advanced Organic Chemistry:.Reactions, Mechanisms, and Structure*, 4th Edition, John Wiley & Sons, New York, pp. 352-357.

Miyaura, N. et al. (1995). "Palladium-Catalyzed Cross-Coupling Reactions of Organoboron Compounds," *Chem. Rev.* 95(7):2457-2483.

Negishi, E. (Jul. 1, 2002). "A Genealogy of Pd-Catalyzed Cross-Coupling," *Journal of Organometallic Chemistry* 653:34-40.

Stille, J.K. (1986). "The Palladium-Catalyzed Cross-Coupling Reactions of Organotin Reagents with Organic Electrophiles," *Angew. Chem. Int. Ed. Engl.* 25:508-524.

Written Opinion mailed on Jan. 9, 2008, for PCT Patent Application No. PCT/AU2007/001761, filed on Nov. 15, 2007, 6 pages.

Advisory Action mailed on Mar. 1, 2012 for U.S. Appl. No. 12/515,250, filed Jan. 5, 2010, 3 pages.

Advisory Action mailed on Jul. 11, 2012 for U.S. Appl. No. 12/515,250, filed Jan. 5, 2010, 3 pages.

Advisory Action mailed on Aug. 21, 2012 for U.S. Appl. No. 12/515,250, filed Jan. 5, 2010, 3 pages.

Advisory Action mailed on Sep. 5, 2012 for U.S. Appl. No. 12/515,250, filed Jan. 5, 2010, 3 pages.

Advisory Action mailed on Jan. 16, 2013 for U.S. Appl. No. 12/515,250, filed Jan. 5, 2010, 3 pages.

Final Office Action mailed on Dec. 22, 2011 for U.S. Appl. No. 12/515,250, filed Jan. 5, 2010, 11 pages.

Non-Final Office Action mailed on Jul. 5, 2011 for U.S. Appl. No. 12/515,250, filed Jan. 5, 2010, 17 pages.

Notice of Allowance mailed on Feb. 7, 2013 for U.S. Appl. No. 12/515,250, filed Jan. 5, 2010, 11 pages.

Australian Office Action mailed on Feb. 15, 2012 for AU Patent Application No. 2007321719, filed on Nov. 15, 2007, 7 pages.

Canadian Office Action mailed on Sep. 24, 2013 for CA Patent Application No. 2,701,959 filed on Nov. 15, 2007, 3 pages.

European Office Action mailed on Mar. 23, 2012 for EP Patent Application No. 07815564.5 filed on Nov. 15, 2007, 6 pages.

Extended European Search Report mailed on Oct. 27, 2010 for EP Patent Application No. 07815564.5 filed on Nov. 15, 2007, 8 pages.

Japanese Office Action mailed on Dec. 4, 2012 for JP Patent Application No. 2009-536562 filed on Nov. 15, 2007, 4 pages.

* cited by examiner

PYRIDINE DERIVATIVES USEFUL AS KINASE INHIBITORS

CROSS-REFERENCE TO RELATED APPLICATIONS

This application is a continuation of U.S. application Ser. No. 12/515,250 having an international filing date of 15 Nov. 2011 and now U.S. Pat. No. 8,461,161, which is the national phase of PCT application PCT/AU2007/001761 having an international filing date of 15 Nov. 2007, which claims benefit of Australian patent application No. 2006906359 filed 15 Nov. 2006 and U.S. Provisional Application Ser. No. 60/901,512 filed 14 Feb. 2007. The contents of the above patent applications are incorporated by reference herein in their entirety.

FIELD OF THE INVENTION

The present invention relates to pyridines or pyrazines that inhibit kinases. In particular the compounds of the invention inhibit members of the class III PTK receptor family such as FMS (CSF-1R), c-KIT, PDGFRβ, PDGFRα or FLT3 and KDR, SRC, EphA2, EphA3, EphA8, FLT1, FLT4, HCK, LCK, PTK5 (FRK), SYK, DDR1 and DDR2 and RET. The compounds of the invention are useful in the treatment of kinase associated diseases such as immunological and inflammatory diseases; hyperproliferative diseases including cancer and diseases involving neo-angiogenesis; renal and kidney diseases; bone remodeling diseases; metabolic diseases; and vascular diseases.

BACKGROUND OF THE INVENTION

Protein kinases are a family of enzymes that catalyse the phosphorylation of specific residues in proteins. In general protein kinases fall into three groups; those which preferentially phosphorylate serine and/or threonine residues, those which preferentially phosphorylate tyrosine residues, and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control including proliferation and cell growth, differentiation, metabolism, apoptosis, cell mobility, mitogenesis, transcription, translation and other signalling processes.

The Protein Tyrosine Kinase family (PTKs) can be divided into the cytoplasmic PTKs (CTKs) and the receptor PTKs (RTKs). The cytoplasmic PTKs include the SRC family, (including: BLK; FGR; FYN; HCK; LCK; LYN; SRC; YES and YRK); the BRK Family (including: BRK; FRK (PTK5), SAD; and SRM); the CSK family (including: CSK and CTK); the TEC family, (including BTK; ITK; TEC; MKK2 and TXK), the Janus kinase family, (including: JAK1, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (also known as the Class III receptors, including PDGFRα, PDGFRβ, CSF-1R, KIT, FLT3); the VEGF-Receptor family (including FLT1, FDR and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family (including LMR1, LMR2 and LMR3); and the SuRTK106 family (including SuRTK106). Similarly, the serine/threonine specific kinases comprise a number of distinct sub-families, including the extracellular signal regulated kinases, (p42/ERK2 and p44/ERK1); c-Jun NH2-terminal kinase (JNK); cAMP-responsive element-binding protein kinases (CREBK); the cyclin dependent kinases (CDKs); cAMP-dependent kinase (CAPK); mitogen-activated protein kinase-activated protein kinase (MAPK and its relatives); stress-activated protein kinase p38/SAPK2; mitogen- and stress-activated kinase (MSK); and protein kinases, PKA, PKB and PKC inter alia.

Additionally, the genomes of a number of pathogenic organisms possess genes encoding protein kinases. For example, the malarial parasite *Plasmodium falciparum* and viruses such as HPV and Hepatitis viruses appear to bear kinase related genes, suggesting that inhibition of kinases may be a useful therapeutic option in the diseases caused by these organisms.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect. Diseases where aberrant kinase activity has been implicated include immunological and inflammatory diseases such as Atopic Dermatitis, asthma, rheumatoid arthritis, Crohn's disease, psoriasis, inflammatory bowel disease, multiple sclerosis, Alzheimers disease and Type I diabetes; hyperproliferative diseases such as cancer for example prostate cancer, colon cancer, gastrointestinal tumors, breast cancer, head and neck cancer, leukemia including acute myelogenous leukemia (AML) and chronic myelogenous leukemia (CML) and lymphoma and diseases involving neo-angiogenesis; renal and kidney diseases such as transplant allograft rejection and fibrosis of the liver and kidney; bone remodeling diseases including osteoporosis; metabolic diseases such as atherosclerosis; and vascular diseases.

Compounds can therefore be directly targeting one or more kinases to achieve a therapeutic effect. Desirable targets of an inhibitor molecule are described below.

PDGF Receptor Family (Class III PTK Receptor Family)

Platelet-derived growth factor (PDGF) is a major mitogen for cells of mesenchymal origin such as fibroblasts, smooth muscle cells, and glial cells. PDGF is a 32 kDa protein heterodimer usually composed of two polypeptide chains, A and B, linked by disulfide bonds. In addition to the PDGF AB heterodimer, two homodimeric forms of PDGF exist, (AA and BB). During blood clotting and platelet adhesion, the PDGF is released from granules at sites of injured blood vessels, suggesting that PDGF may have a role in the repair of blood vessels. PDGF may stimulate migration of arterial smooth muscle cells from the medial to the intimal layer of the artery where the muscle cells may proliferate. The cellular proliferation induced by all isoforms of PDGF is mediated by ligand binding to the PDGF receptor. The PDGF receptor belongs to the class III tyrosine kinase family and consists of two receptor subtypes, termed type A (or type alpha), and type B (or type beta. Other members of the PDGF receptor family include CSF-1R, cKIT and FLT3.

FMS (CSF-1R)

CSF-1 is a potent growth and differentiation factor for bone marrow progenitor cells in particular those of the mononuclear phagocyte lineage. CSF-1 stimulates the proliferation and end-cell function of mature macrophages via specific receptors on responding cells. The biological activities of CSF-1 are mediated by a receptor of 165 kDa. The CSF-1 receptor is encoded by the c-fms gene which encodes the proto-oncogene c-FMS. As a member of the type III receptor tyrosine kinase family, CSF-1R has overall structural similarity to c-KIT, PDGFRα, PDGFRβ and FLT3. The receptor is a transmembrane protein with an extracellular ligand-binding domain of 512 amino acids, an intramembrane domain of 25 amino acids, and a cytoplasmic domain of 435 amino acids encoding a bipartite tyrosine kinase interrupted by a so-called kinase insert. Binding of the ligand activates the tyrosine kinase activity of the receptor. The cellular c-FMS proto-oncogene is the cellular homologue of a viral oncogene called v-FMS which is encoded by SM-FeSV (Susan McDonough strain of Feline sarcoma virus). The viral oncogene encodes a protein with a constitutive kinase activity.

Mutations activating the CSF-1 receptors have been observed in approximately 10 percent of the patients with myelodysplastic syndromes. A deletion of both alleles of the CSF-1R locus, which maps to human chromosome 5q33.2-3 in the vicinity of the receptor gene for PDGF, is found in the bone marrow cells of some of these patients (known as 5q minus syndrome). Mice with a targeted disruption of the c-fms gene are essentially a phenocopy of the op/op mouse, indicating that all of the actions of CSF-1 are mediated by the CSF-1R. These data indicate that a specific inhibitor of the CSF-1R would be expected to reduce monocyte production and macrophage numbers in vivo.

The major source of circulating CSF-1 is thought to be endothelial cells that line blood vessels, but a range of other cell types including fibroblasts, osteoblasts, monocytes, B cells, T cells and bone marrow stromal cells also produce CSF-1. Plasma CSF-1 levels are dramatically increased upon challenge with lipopolysaccharide or with infectious agents such as *Listeria monocytogenes* and *Candida albicans*. In humans, CSF-1 levels appear to be enhanced in patients with sepsis and LPS administration to cancer patients increased CSF-1 levels.

The involvement of macrophages in chronic inflammatory diseases such as rheumatoid arthritis (RA) is well established. In a murine model of collagen-induced arthritis, administration of CSF-1 exacerbated disease severity whilst an anti-CSF-1 antibody reduced the severity of established arthritis. CSF-1 has also been implicated as a contributor to disease severity in other arthritic models. Evidence exists for CSF-1 involvement in RA itself; synovial fibroblasts from RA patients produce CSF-1; CSF-1 levels were elevated in RA patient sera and synovial fluid.

There is an extensive literature on the contribution of CSF-1 to kidney disease.

Macrophage accumulation is a predictor of renal outcome in glomerulonephritis and correlates with kidney dysfunction in humans and elevated levels of renal CSF-1 are apparent in glomerulonephritis patients. In experimental disease models, there is clear evidence for the involvement of CSF-1 in directing excessive macrophage proliferation and tissue damage. The severity of lupus nephritis in MRL-lpr mice correlated with CSF-1 levels, whereas treatment with anti-CSF-1R antibody reduced local macrophage proliferation during experimentally-induced renal inflammation.

Multiple Sclerosis (MS) is a heterogenous disease in which various cellular infiltrates occur at different stages of the disease. In early steps, the immunopathology involves specific antigen recognition by autoreactive T cells and autoantibodies. In later stage, activated macrophages and glial cells predominate producing a large number of inflammatory mediators.

Alzheimer's disease (AD) constitutes a chronic cerebral inflammatory state that eventuates in neuronal injury. Microglia cells contribute to the pathophysiology of AD. CSF-1, a microglial activator is found at high levels in the central nervous system and augments β-amyloid peptide-induced microglial production of IL-1, Il-6 and nitric oxide which in turn intensify the cerebral inflammatory state by activating astrocytes and other microglia and directly induce neuronal injuries.

Expression of CSF-1 and its cognate receptor, c-fms have been detected at both the transcript and protein levels in Hodgkin's disease-derived cell lines derived from patients with nodular sclerosis. Inhibition of cell growth with antiserum to CSF-1 is indicative of an autocrine growth regulation pathway in these cells.

CSF-1 is produced by a very wide diversity of tumour cells in mouse and human and CSF-1 contributes to the attraction of large numbers of macrophages that are a significant component of the stroma of all solid tumours. CSF-1 is produced in more than 70% of breast tumours and may contribute to the overall disease through autocrine stimulation of the tumour cells, as well as through tumour-associated immunosuppression.

Macrophages attracted to the tumour by CSF-1 may also play a role in the metastatic spread of the tumour, and it has been shown that anti-CSF-1 therapy can diminish growth of human tumour xenografts in mice. Interestingly, ectopic expression of the native CSF-1R appears to be sufficient to generate transformation of non-malignant cells to clonogenic growth in vitro. In cells that are already clonogenic, CSF-1R expression can increase both clonogenicity and the size of individual clonal colonies formed in semi-solid medium.

There have been a number of reports indicating the CSF-1 can be expressed outside of the macrophage lineage, in testis, uterus, ovary and mammary glands, at some stages of development. A role for CSF-1 in normal development of the mammary gland in mice has been demonstrated, although this could be attributable to the crucial role of infiltrating macrophages in branching morphogenesis. By contrast, CSF-1R is expressed on a wide range of human solid tumours, notably breast, ovarian, endometrial and prostate tumours and also of B lymphocyte malignancies. A functional autocrine loop in these tumour types has been demonstrated based upon immunocytochemical localisation using antibodies directed against phosphotyrosine moieties on the active receptor, and the expression of a CSF-1/CSF-1R autocrine loop in breast and ovarian cancer is strongly correlated with disease progression and poor prognosis and is most likely causally linked to activation of the ras-raf-MAPK-Ets pathway inducing the production of invasive mediators, such as urokinase plasminogen activator. The most direct evidence for a causal role of CSF-1/CSF-1 autocrine/paracrine signalling in the progression stage of breast cancer came from crossing a mammary cancer prone mouse strain to the CSF-1-deficient op/op mouse strain, Lin and co-workers showed that cancer incidence was unaffected, but progression and metastasis were constrained in the absence of the growth factor.

It is well established that the skeleton is the most common site of distant metastases of breast, prostate, and lung carcinoma. The bone appears to provide a 'fertile soil' or environment for the cancer cells to germinate. Once tumour has metastasized to the bone, the disease is incurable due to bone pain, fracture, hypercalcemia and nerve compression. The bone is a repository of a number of growth factors and histology sections confirm that the tumour cells reside adjacent to osteoclasts and bone destruction in cancer is mediated by osteoclasts. Osteoclasts arise from a common progenitor as blood-borne monocytes and the activities of bone resorption is dependent on the actions of CSF-1, the ligand for fms and also RANKL. It has been demonstrated that many tumours spontaneously secrete large quantity of CSF-1 and RANKL is expressed by osetoblasts in the bone. In this respect, osteoclasts is reliant on CSF-1 and RANKL for their degradative activities.

The osteoclast, the exclusive bone resorptive cell, is a member of the monocyte/macrophage family that arises in vitro from myeloid precursors, with bone marrow macrophages representing the largest reservoir. Whilst M-CSF mediates the survival and proliferation of precursors of the monocyte/macrophage lineage and their differentiation into mature phagocytes supports the notion that cells of the myeloid lineage are osteoclast precursors suggested that M-CSF plays an important role in osteoclast biology and indeed, op/op mice, which fail to express functional M-CSF, are osteopetrotic.

Furthermore, administration of soluble M-CSF to op/op mice rescues their osteoperosis. The critical role played by the CSF-1/FMS axis in osteoclast differentiation suggests that manipulation of this axis by the use of a FMS inhibitor may be useful pharmacologically in situations where osteoclast function might be too high.

M-CSF has been implicated as playing a role in several diseases including inflammation. Most notable is the role of M-CSF in cancer, particularly angiogenism. Therefore down regulating M-CSF is an area of intense interest.

Atherosclerosis is a complex pathological process resulting from the interaction of inflammatory and fibro-proliferative responses. Administration of a macrophage-colony stimulating factor (M-CSF) monoclonal antibody (AFS98) to adult apolipoprotein E (apoE)-deficient mice demonstrated that the macrophage and M-CSF/c-FMS axis play an essential role in the arterial wall during development of the fatty streak lesion and that blockade of the M-CSF/c-fms pathway could act as protection from at least early atherogenesis.

Macrophages are a major component of the innate immune system. Their destructive potential is essential for protection against a wide diversity of infection, and is required for normal tissue turnover, remodelling during development and repair of injury. However, uncontrolled macrophage infiltration into tissues, or activated release of their products, causes much of the pathology of infectious, inflammatory and malignant disease. Therapies that control macrophage production, recruitment or activation are likely to have wide application in clinical and veterinary medicine. Osteoarthritis, in particular has been shown to be caused in part the over-production of macrophages in the synovial fluid of joints, leading to cartilage loss, inflammation and pain. One effective approach to the control of macrophage populations would be the generation of inhibitors of the CSF-1R, such as those described in this application. This would be desirable in diseases such as immunological and inflammatory diseases; hyperproliferative diseases including cancer and diseases involving neo-angiogenesis; renal and kidney diseases; bone remodeling diseases; metabolic diseases; and vascular diseases. Particularly therapies for myelodisplastic syndromes, rheumatoid arthritis, multiple sclerosis, Alzheimer's disease, Hodgkin's disease, kidney disease, human solid tumors including breast, ovarian, endometrial and prostate tumors, osteoperosis and artherosclerosis.

PDGFRβ

The two PDGF receptor isoforms may be distinguished by their markedly different ligand binding specificities. PDGF beta receptor binds only B-chain (isoforms BB and AB), while PDGF alpha receptor can bind all forms of PDGF (isoforms containing A and/or B chain).

With the importance of PDGF-related processes to proliferation of endothelial cells and vascular smooth muscle, there are a range of pathogenic processes that an inhibitor of the PDGFRβ kinase domain could be used for diseases such as immunological and inflammatory diseases; hyperproliferative diseases including cancer and diseases involving neo-angiogenesis; renal and kidney diseases; bone remodeling diseases; metabolic diseases; and vascular diseases. Specifically, these include: restenosis, including coronary restenosis after angioplasty, atherectomy, or other invasive methods of plaque removal, and renal or peripheral artery restenosis after the same procedures; vascular proliferative phenomena and fibrosis associated with other forms of acute injury such as: pulmonary fibrosis associated with adult respiratory distress syndrome, renal fibrosis associated with nephritis, coronary stenosis associated with Kawasake's disease and vascular narrowings associated with other arteritides such as Takayasha's disease; prevention of narrowings in vein grafts; prevention of narrowings due to accelerated smooth muscle cell migration and proliferation in transplanted organs; other fibrotic processes, such as scleroderma and myofibrosis and inhibition of tumor cell proliferation that is mediated by PDGF.

KIT

Stem cell factor (SCF), also known as Kit ligand (KL), steel factor or mast cell growth factor is the ligand of the c-kit proto-oncogene product. W and SI mice are two strains of mice with similar phenotypic defects in pigmentation. Both are anemic and sterile and have mutations in the c-kit and scf loci, respectively. SCF was first described as a pluripotent growth factor involved in the early stages of haematopoiesis, as well as in the development and function of germ cells and melanocytes. In addition, SCF may be implicated in inflammatory processes. More than thirty activating mutations of the Kit protein have been associated with highly malignant tumors in humans. The c-kit proto-oncogene is a Class III RTK, believed to be important in embryogenesis, melanogenesis, and hematopoiesis. There is evidence that this receptor is involved in the pathogenesis of Mastocytosis/Mast Cell Leukemia, Gastrointestinal Stromal Tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. Accordingly, it would be desirable to develop compounds that are inhibitors of the tyrosine kinase activity of c-KIT receptor for use in diseases such as immunological and inflammatory diseases; hyperproliferative diseases including cancer and diseases involving neo-angiogenesis; renal and kidney diseases; bone remodeling diseases; metabolic diseases; and vascular diseases, such as the examples described above.

FLT3

FMS-related tyrosine kinase 3 (FLT3) is a receptor tyrosine kinase preferentially expressed in hematopoietic progenitor cells. Its ligand, FLT3-L, stimulates the growth of hematopoietic progenitors from the bone marrow, peripheral blood, and cord blood. FLT3-L appears to work in synergy with other hematopoietic growth factors exerting pleiotropic effects on precursors of both the myeloid and lymphoid lineages. In combination with myeloid growth factors such as granulocyte-macrophage and granulocyte colony-stimulating factor (GM-CSF and G-CSF), or CSF-1, FLT3-L increases the number of myeloid colonies generated from the committed colony-forming units. Similarly, there is evidence that FLT3-L synergizes with the interleukins IL-7, IL-3, and IL-11 to stimulate B lymphopoiesis in vitro, with IL-12 in the presence of thymic stroma to promote T cell development, and with IL-15 to drive the development of NK cells. Taken together, these observations suggest that FLT3-L is able to nuance the induction of the development of several hematopoietic lineages, by enhancing and/or modifying the action of other cytokines or interleukins.

Recent studies have indicated that the FLT3 gene is mutated by internal tandem duplication in 20-25% of adults with acute myelogenous leukemia (AML), leading to phosphorylation and overactivation of FLT3 activity in cancerous cells. AML is the most common type of leukemia in adults, with an estimated 10,000 new cases annually. FLT3 has also been implicated in neural-crest derived tumors and myelodysplastic syndromes. Furthermore, mutation of FLT3 at aspartic acid 835 (asp835) has been implicated in progression of AML. It is conceivable also that activation of the FLT3 receptor kinase leading to AML may occur in the absence of genetic mutations of the FLT3 gene. Inhibitors of FLT3 are presently being studied as potential AML therapeutics. For example, agonist antibodies that bind the extracellular domain of FLT3 and activate its tyrosine kinase activity have been described. More recent results indicate that FLT3 inhibitors have anti-tumor activity in pre-clinical models.

Accordingly, new and improved reagents for the detection of FLT3 activity would be desirable, including development of reagents against newly-identified sites of FLT3 phosphorylation. Since phosphorylation-dependent over-activation of FLT3 is associated with diseases such as AML, reagents enabling the specific detection of FLT3 activation would be useful tools for research and clinical applications.

Furthermore FLT3 inhibitors are likely to be useful in hyperproliferative diseases including myeloproliferative diseases such as AML.

VEGF Receptor Family

The Vascular Endothelial Growth Factor (VEGF) is a dimeric protein also known as vascular permeability factor because it acts on endothelial cells to regulate the permeability of those cells as well as their proliferation. These two activities are mediated through its tyrosine kinase receptors (FLT1, FLT4 and KDR), which are also regulators of angiogenesis. The KDR receptor mediates the biological activity of mitogenesis and proliferation of endothelial cells.

Angiogenesis is limited in normal adults primarily to wound healing, pregnancy and corpus luteum formation, but it is induced in many diseases including cancer (particularly pulmonary adenocarcinoma and non small cell carcinoma), diabetic retinopathy, rheumatoid arthritis, psoriasis, atherosclerosis and restenosis. Solid tumours particularly rely on angiogenesis for their growth, and successful metastasis also requires the presence of blood vessels to allow tumour cells to enter the circulation.

Inhibitors of KDR will be useful in the treatment of diseases such as immunological and inflammatory diseases; hyperproliferative diseases including cancer and diseases involving neo-angiogenesis; renal and kidney diseases; bone remodeling diseases; metabolic diseases; and vascular diseases, including those described above.

SRC Family

The SRC and BTK families of kinases are important for normal cellular proliferation, however their over expression and over activation can promote the development of cancer. There are nine members of the SRC family of PTKs, including c-SRC, YES, FGR, FYN, LYN, LCK, HCK, BLK and YRK. The BRK family includes BRK, FRK (PTK5), SAD and SRM.

c-SRC is found in a broad range of tissues with especially high levels of expression in neuronal and heatopoietic cells. c-SRC is involved in cellular adhesion, invasion and motility of tumour cells.

The effects of elevated SRC kinase activity have been extensively studied in vitro using a variety of human neoplastic cell lines and in vivo with murine models. Using these systems, the effects of SRC on tumour initiation and progression were studied and suggested a role for c-SRC in almost every aspect of a cell's life including mitogenesis, proliferation, survival, control of cellular adhesion and migration, all of these processes are de-regulated during cancer progression. These factors led to investigation of a possible role of SRC in human tumorigenesis. Elevated SRC kinase activity has been found in human mammary carcinoma. Using a human breast cancer cell line, MDA-MB-231, which was injected into the left ventricle of Balb/C-nu/nu mice, a c-SRC inhibitor was seen to reduce morbidity and lethality, and also the incidence of metastases both in bone and visceral organs. The compound also inhibited osteoclast formation and bone resorption suggesting a direct inhibition of osteoclast activity and contribute to the reduced incidence of osteolytic lesions. One advantage for using SRC inhibitors for cancer therapy is that deficiency of SRC in mice appears to affect only bone cell formation with no effects on other organs.

In addition to breast cancer, elevated SRC activity has been reported in many other epithelial tumours including pancreatic, lung, ovarian, esophageal, colonic, neuroblastoma, melanoma, mesothelioma and gastric cancer. Cell lines derived from these tumours display up to 30× elevation of SRC activity.

In regard to the mode of SRC activation, SRC can be activated by receptor tyrosine kinases such as EGFR and HGF all of which are known to be active in the course of cancer progression. In this respect, SRC association with these receptor tyrosine kinases is instrumental in malignant transformation. C—SRC has also been implicated to interact with the JM domain of CSF1-R, a receptor tyrosine kinase that mediates CSF-1 signalling. CSF-1 is a key cytokine for growth and survival of cells of the mononuclear-phagocytic lineage and cells of this lineage have been known to associate with solid tumours and are known as tumour-associated macrophages (TAMs) that elaborate release of VEGF, MMPs and uPA, mediators that facilitate tumour metastatic processes. Furthermore, elevated epithelial co-expression of CSF-1 and fms has been shown in >50% of mammary tumours and autocrine CSF1-R activation has been shown to promote SRC-dependent disruption of junctional integrity in acinar structures in human mammary epithelial cells, a pre-requisite to tumour escape from primary sites.

A SRC inhibitor, AP23846, has been shown to reduce VEGF and IL-8 expression in human solid tumour cell lines and fails to support angiogenesis into gel foams implanted s.c. in mice. IL-8 is a pro-angiogenic factor that is a prognostic marker for many tumours and VEGF is an essential factor in support of angiogenesis. Other experiments have also shown that following VEGF stimulation, SRC preferentially associates with KDR/VEGFR-2 rather than Flt-1, the two main VEGF receptors present on vascular endothelial cells, thus highlight the potential significance of upregulated KDR-associated SRC activity in the process of angiogenesis.

The SRC family of kinases have also been implicated in bone remodelling diseases. For example, mice deficient in SRC develop osteoporosis because of depressed bone resorption by osteoclasts, suggesting that osteoporosis resulting from abnormally high bone resorption can be treated by inhibiting SRC. SRC inhibition may prevent joint destruction that is characteristic in patients suffering from rheumatoid arthritis. SRC is also required for replication of the hepatitis B virus, suggesting a role for SRC inhibitors in viral diseases.

Thus inhibitors of SRC family kinases could be useful for treatment of diseases such as immunological and inflammatory diseases; hyperproliferative diseases including cancer and diseases involving neo-angiogenesis; renal and kidney diseases; bone remodeling diseases; metabolic diseases; and vascular diseases. Examples include breast, pancreatic, lung, ovarian, esophageal, colonic, neuroblastoma, melanoma, mesothelioma and gastric cancer, pulmonary adenocarcinoma and non small cell carcinoma, osteoporosis, and rheumatoid arthritis.

EPH Family

The Eph family of receptor tyrosine kinases are epithelial cell kinases and family members include EPHA2, EPHA3, and EPHA8.

EPHA2 is a 130 kDa member of the EPH family. The function of EPHA2 has been suggested to include regulation of proliferation, differentiation, and barrier function of colonic epithelium, vascular network assembly, endothelial migration, capillary morphogenesis and angiogenesis, nervous system segmentation and axon path finding.

The ligand of EPHA2 is Ephrin A1 and this interaction is thought to help anchor cells on the surface of an organ, as well as down regulating epithelial and/or endothelial proliferation. It is understood that under normal conditions the interaction helps regulate over proliferation and growth of epithelial cells, however if this barrier is prevented from forming or shed, prevention of proper healing may result.

As a result inhibitors of the EPH family of kinases, and in particular EPHA2 will be useful in a range of immunological and inflammatory disorders including interstitial cystitis (IC) and inflammatory bowel disease (IBD).

RET

RET encodes a receptor tyrosine kinase. Somatic chromosomal rearrangements involving the RET gene represent the most frequent genetic alteration in papillary thyroid cancer (PTC), the most common thyroid malignancy. As activating mutations of genes coding for tyrosine kinases occur early in cancer development, targeting these kinases provides a promising therapeutic opportunity.

Consequentially an inhibitor of RET is desirable for the treatment of a range of diseases including hyperproliferative diseases such as thyroid cancer.

There is therefore a need to develop inhibitors of one or more of FMS (CSF-1R), c-KIT, PDGFRβ, FLT3, KDR, SRC, EphA2, EphA3, EphA8, FLT1, FLT4, HCK, LCK, PTK5 (FRK) and RET, for therapies of a range of disease states including immunological and inflammatory diseases; hyperproliferative diseases including cancer and diseases involving neo-angiogenesis; renal and kidney diseases; bone remodeling diseases; metabolic diseases; and vascular diseases.

SUMMARY OF THE INVENTION

In a first aspect, the present invention provides a compound of formula I:
wherein

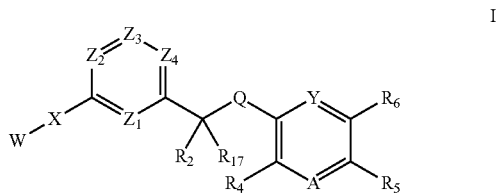

Q is $NR^3$, O or S;

W is H, 3 to 8 membered cycloalkyl, 5 to 7 membered aryl or heterocyclyl having from 1 to 3 heteroatoms selected from N, O, S, S(O) and $S(O)_2$, wherein the cycloalkyl, aryl or heterocyclyl may be substituted with 1 to 3 substituents independently selected from $R_{17}$, substituted or unsubstituted $C_{1-4}$ alkyl, OH, $NO_2$, $NR_7R_8$, halogen, $CF_3$, $OCF_3$, CN, $SO_2C_{1-4}$ alkyl, $OC_{1-4}$ alkyl, $C_{1-4}$ alkyl OH, $C_{1-4}$ alkyl$OC_{1-4}$ alkyl, $C_{1-4}$ alkyl $NR_7R_8$, $CONR_7R_8$, $COR_9$, $CO_2R_9$, $C_{3-8}$ cycloalkyl, aryl or heterocyclyl, wherein the cycloalkyl, aryl or heterocyclyl may be substituted 1 or 2 times with substituted or unsubstituted $C_{1-4}$alkyl;

X is absent or selected from O, $NR_9$, S, SO, $SO_2$, NHCO, CONH, NHCONH, $NHCH(CH_3)$, $NHCH(CF_3)$, $NHCH_2$, $N(CH_3)CO$, $N(CH_2CH_3)CO$, $N(CH_3)CH_2$, $NHSO_2$, $N(CH_3)CH(CF_3)$ and $NHC_{1-6}$ alkylene wherein up to 3 carbon atoms of the alkylene are optionally replaced with $NR_3$, S or O;

each of $Z_1$ to $Z_4$ is independently selected from N and $CR_1$ provided that no more than two of $Z_1$ to $Z_4$ are N;

each $R_1$ is independently selected from H, halogen, $CF_3$, $OCF_3$, substituted or unsubstituted $C_{1-4}$ alkyl and substituted or unsubstituted $OC_{1-4}$ alkyl;

$R_2$ and $R_{17}$ are independently selected from H, substituted or unsubstituted $C_{1-4}$ alkyl, $CF_3$, substituted or unsubstituted $C_{1-4}$ alkylOH and substituted or unsubstituted $C_{1-4}$ alkyl$OC_{1-4}$ alkyl; or $R_2$ and $R_{17}$ together with the carbon atom to which they are attached form a substituted or unsubstituted $C_{3-8}$cycloalkyl or substituted or unsubstituted 3 to 8 membered saturated heterocyclyl;

$R_3$ is selected from H and substituted or unsubstituted $C_{1-4}$ alkyl;

A and Y are independently selected from $CR_3$ and N;

$R_4$ and $R_5$ are independently selected from H, substituted or unsubstituted $C_{1-4}$ alkyl, $CF_3$, halogen and $NR_9R_{10}$;

$R_6$ is selected from H, halogen, $OR_{11}$, $NR_{12}R_{13}$, substituted or unsubstituted $C_{1-4}$alkyl, substituted or unsubstituted $C_{1-4}$ alkylOH, $CO_2R_9$, and $CONR_7R_8$, $S(O)_nR_{14}$ and aryl or 5 to 7 membered heterocyclyl having from 1 to 3 heteroatoms selected from N, O, S, SO and $SO_2$, wherein the aryl or heterocyclyl may be substituted with 1 to 3 substituents independently selected from substituted or unsubstituted $C_{1-4}$ alkyl, OH, $NR_{15}R_{16}$, halogen, $CF_3$, $OCF_3$, CN, substituted or unsubstituted $OC_{1-4}$ alkyl, substituted or unsubstituted $OC_{2-4}$ alkyleneOH, $OC_{2-4}$alkyleneNR$_7R_8$, substituted or unsubstituted $C_{1-4}$ alkyleneOH, substituted or unsubstituted $C_{1-4}$ alkyleneOC$_{1-4}$ alkyl, substituted or unsubstituted $C_{1-4}$ alkyleneNR$_7$R$_8$, CONR$_7$R$_8$, CO$_2$R$_9$, NR$_7$COR$_9$, NR$_7$SO$_2$C$_{1-4}$ alkyl, N(SO$_2$C$_{1-4}$ alkyl)$_2$, NR$_7$CONR$_8$C$_{1-4}$ alkyl, SO$_2$NR$_9$R$_{10}$, OP(O)(OR$_7$)$_2$, SO$_2$C$_{1-4}$ alkyl, substituted or unsubstituted aryl or substituted or unsubstituted heterocyclyl;

n is 0 to 2;

$R_7$ and $R_8$ are independently selected from H, substituted or unsubstituted $C_{1-4}$ alkyl, substituted or unsubstituted $C_{1-4}$ alkyleneOH, $C_{1-4}$ alkylene OC$_{1-4}$alkyl, $C_{1-4}$alkylene NR$_{15}$R$_{16}$, COC$_{1-4}$ alkyl and substituted or unsubstituted aryl; or $R_7$ and $R_8$ together with the nitrogen to which they are attached form a 5 to 7 membered heterocyclyl which contains 1 to 2 heteroatoms selected from N, O, S, SO and SO$_2$ which may be substituted with H, $C_{1-4}$alkyl, OR$_9$ or NR$_9$R$_{10}$;

$R_9$ and $R_{10}$ are independently selected from H and substituted or unsubstituted $C_{1-4}$ alkyl;

$R_{11}$ is independently selected from H, substituted or unsubstituted $C_{1-4}$ alkyl, substituted or unsubstituted $C_{2-4}$ alkyleneOH and substituted or unsubstituted $C_{2-4}$ alkylene NR$_7$R$_8$;

$R_{12}$ and $R_{13}$ are independently selected from H, substituted or unsubstituted $C_{1-4}$ alkyl, substituted or unsubstituted aryl, substituted or unsubstituted $C_{2-4}$ alkyleneOH, COC$_{1-4}$ alkyl, COaryl and COheterocyclyl; or $R_{12}$ and $R_{13}$ together with the nitrogen to which they are attached form a 5 to 7 membered heterocyclyl which contains 1 or 2 heteroatoms selected from N, O, S, SO and SO$_2$ and may be substituted with substituted or unsubstituted $C_{1-4}$ alkyl, OR$_9$ or NR$_9$R$_{10}$;

$R_{14}$ is selected from aryl or a 5 to 7 membered heterocyclyl having from 1 to 3 heteroatoms selected from N, O, S, SO and SO$_2$, wherein the aryl or heterocyclyl may be substituted with 1 to 3 substituents selected from substituted or unsubstituted $C_{1-4}$ alkyl, OH, NR$_{15}$R$_{16}$, halogen, CF$_3$, OCF$_3$, CN, OC$_{1-4}$alkyl, OC$_{2-4}$ alkyleneOH, C$_{1-4}$ alkylene OH, C$_{1-4}$ alkyleneOC$_{1-4}$ alkyl, $C_{1-4}$ alkyleneNR$_{15}$R$_{16}$, CONR$_{15}$R$_{16}$, CO$_2$R$_9$, NR$_7$SO$_2$CH$_3$, N(SO$_2$CH$_3$)$_2$, NR$_7$CONR$_8$C$_{1-4}$ alkyl, SO$_2$NR$_{15}$R$_{16}$, OP(O)(OR$_7$)$_2$, substituted or unsubstituted aryl and substituted or unsubstituted heterocyclyl;

$R_{15}$ and $R_{16}$ are independently selected from H, substituted or unsubstituted substituted or unsubstituted C$_{1-4}$alkylOH, substituted or unsubstituted C$_{1-4}$alkylOC$_{1-4}$alkyl, COC$_{1-4}$alkyl and S(O)CH$_3$; or $R_{15}$ and $R_{16}$ together with the nitrogen to which they are attached form a 5 to 6 membered heterocyclyl which contains 1 to 2 heteroatoms selected from N, O and S which may be substituted with substituted or unsubstituted $C_{1-4}$ alkyl, OR$_9$ or NR$_9$R$_{10}$, salts, isomers and/or prodrugs thereof.

In a second aspect, there is provided a process for the preparation of the compound of formula I defined above wherein X is an amide or sulphonamide which comprises coupling a compound of formula II

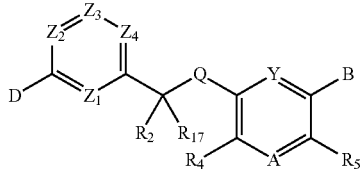

Formula II wherein

D is NH$_2$, NHR or CO$_2$H;

R is $C_{1-4}$alkyl;

B is a leaving group; and $Z_1$, $Z_2$, $Z_3$, $Z_4$, $R_2$, $R_4$, $R_5$, $R_{17}$, Q, Y and A are as defined above; with WR' wherein W is as defined above and R' is NH$_2$, NHR, CO$_2$H, COCl, SO$_2$Cl, COR or CHO, so that R' and D condense to form X as defined above.

The compounds of formula I are kinase inhibitors, in particular inhibitors of members of the class III PTK receptor family such as FMS (CSF-1R), c-KIT, PDGFRβ, PDGFRα or FLT3 and KDR, SRC, EphA2, EphA3, EphA8, FLT1, FLT4, HCK, LCK, PTK5 (FRK), RET, SYK, DDR1 or DDR2.

These compounds are useful in the treatment of a kinase associated disease, preferably a disease associated with members of the class III PTK-receptor family such as FMS (CSF-1R), c-KIT, PDGFRβ, PDGFRα or FLT3 and KDR, SRC, EphA2, EphA3, EphA8, FLT1, FLT4, HCK, LCK, PTK5 (FRK), RET, SYK, DDR1 or DDR2 associated diseases such as immunological and inflammatory diseases; hyperproliferative diseases including cancer and diseases involving neo-angiogenesis; renal and kidney diseases; bone remodeling diseases; metabolic diseases; and vascular diseases.

In a third aspect, there is provided a kinase inhibitor comprising the compound formula I defined above.

There is also provided use of the compound of formula I defined above as a kinase inhibitor.

There is further provided the compound of formula I defined above for use as a kinase inhibitor.

In one embodiment the compounds of formula I act as inhibitors of members of the class III PTK family such as FMS (CSF-1R), c-KIT, PDGFRβ, PDGFRα or FLT3 and KDR, SRC, EphA2, EphA3, EphA8, FLT1, FLT4, HCK, LCK, PTK5 (FRK), RET, SYK, DDR1 or DDR2.

The compound of formula I may also be administered in the form of a pharmaceutical composition together with a pharmaceutically acceptable carrier.

In a fourth aspect, there is provided a pharmaceutical composition comprising the compound of formula I defined above and a pharmaceutically acceptable carrier.

In one embodiment, the pharmaceutical composition also comprises one or more additional therapeutic agents.

In a fifth aspect, there is provided an implant which comprises the compound of formula I defined above.

In a sixth aspect, there is provided a method for the treatment of a kinase associated disease including immunological and inflammatory diseases; hyperproliferative diseases including cancer and diseases involving neo-angiogenesis; renal and kidney diseases; bone remodeling diseases; metabolic diseases; and vascular diseases which comprises administering a therapeutically effective amount of the compound of formula I or a pharmaceutical composition defined above to a subject in need thereof.

There is also provided use of the compound of formula I or a pharmaceutical composition as defined above in the manufacture of a medicament for the treatment of a kinase associated disease including immunological and inflammatory diseases; hyperproliferative diseases including cancer and diseases involving neo-angiogenesis; renal and kidney diseases; bone remodeling diseases; metabolic diseases; and vascular diseases.

There is further provided use of the compound of formula I or a pharmaceutical composition as defined above in the treatment of a kinase associated disease including immunological and inflammatory diseases; hyperproliferative diseases including cancer and diseases involving neo-angiogenesis; renal and kidney diseases; bone remodeling diseases; metabolic diseases; and vascular diseases.

There is still further provided the compound of formula I or a pharmaceutical composition defined above for use in the treatment of a kinase associated disease including as immunological and inflammatory diseases; hyperproliferative diseases including cancer and diseases involving neo-angiogenesis; renal and kidney diseases; bone remodeling diseases; metabolic diseases; and vascular diseases.

In a seventh aspect, there is provided a method of inhibiting a kinase in a cell comprising contacting the cell with the compound of formula I defined above.

In an eighth aspect there is provided a method of control of macrophage populations comprising contacting the macrophage population with the compound of formula I defined above.

DETAILED DESCRIPTION OF THE INVENTION

The present invention relates to compounds of formula I that inhibit kinases, in particular members of the class PTKIII receptor family such as FMS (CSF-1R), c-KIT, PDGFRβ, PDGFRα or FLT3 and KDR, SRC, EphA2, EphA3, EphA8, FLT1, FLT4, HCK, LCK, PTK5 (FRK), RET, SYK, DDR1 or DDR2 and are useful in the treatment of kinase associated diseases including immunological and inflammatory diseases; hyperproliferative diseases including cancer and diseases involving neo-angiogenesis; renal and kidney diseases; bone remodeling diseases; metabolic diseases; and vascular diseases.

In a first aspect, the present invention provides a compound of formula I:

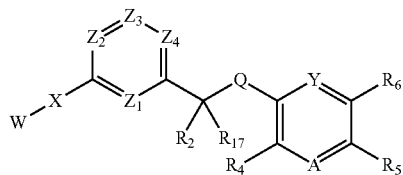

wherein
Q is $NR^3$, O or S;
W is H, 3 to 8 membered cycloalkyl, 5 to 7 membered aryl or heterocyclyl having from 1 to 3 heteroatoms selected from N, O, S, S(O) and S(O)$_2$, wherein the cycloalkyl, aryl or heterocyclyl may be substituted with 1 to 3 substituents independently selected from $R_{17}$, substituted or unsubstituted $C_{1-4}$ alkyl, OH, $NO_2$, $NR_7RE$, halogen, $CF_3$, $OCF_3$, CN, $SO_2C_{1-4}$ alkyl, $OC_{1-4}$ alkyl, $C_{1-4}$ alkyl OH, $C_{1-4}$ alkylOC$_{1-4}$alkyl, $C_{1-4}$ alkyl $NR_7R_8$, $CONR_7R_8$, $COR_9$, $CO_2R_9$, $C_{3-8}$ cycloalkyl, aryl or heterocyclyl, wherein the cycloalkyl, aryl or heterocyclyl may be substituted 1 or 2 times with substituted or unsubstituted $C_{1-4}$alkyl;
X is absent or selected from O, $NR_9$, S, SO, $SO_2$, NHCO, CONH, NHCONH, NHCH(CH$_3$), NHCH(CF$_3$), NHCH$_2$, N(CH$_3$)CO, N(CH$_2$CH$_3$)CO, N(CH$_3$)CH$_2$, NHSO$_2$, N(CH$_3$)CH(CF$_3$) and NHC$_{1-6}$ alkylene wherein up to 3 carbon atoms of the alkylene are optionally replaced with $NR_3$, S or O;

each of $Z_1$ to $Z_4$ is independently selected from N and $CR_1$ provided that no more than two of $Z_1$ to $Z_4$ are N;
each $R_1$ is independently selected from H, halogen, $CF_3$, $OCF_3$, substituted or unsubstituted $C_{1-4}$ alkyl and substituted or unsubstituted $OC_{1-4}$ alkyl;
$R_2$ and $R_{17}$ are independently selected from H, substituted or unsubstituted $C_{1-4}$ alkyl, $CF_3$, substituted or unsubstituted $C_{1-4}$ alkylOH and substituted or unsubstituted $C_{1-4}$ alkylOC$_{1-4}$ alkyl; or
$R_2$ and $R_{17}$ together with the carbon atom to which they are attached form a substituted or unsubstituted $C_{3-8}$cycloalkyl or substituted or unsubstituted 3 to 8 membered saturated heterocyclyl;
$R_3$ is selected from H and substituted or unsubstituted $C_{1-4}$ alkyl;
A and Y are independently selected from $CR_3$ and N;
$R_4$ and $R_5$ are independently selected from H, substituted or unsubstituted $C_{1-4}$ alkyl, $CF_3$, halogen and $NR_9R_{10}$;
$R_6$ is selected from H, halogen, $OR_{11}$, $NR_{12}R_{13}$, substituted or unsubstituted $C_{1-4}$alkyl, substituted or unsubstituted $C_{1-4}$ alkylOH, $CO_2R_9$, and $CONR_7R_8$, $S(O)_nR_{14}$ and aryl or 5 to 7 membered heterocyclyl having from 1 to 3 heteroatoms selected from N, O, S, SO and $SO_2$, wherein the aryl or heterocyclyl may be substituted with 1 to 3 substituents independently selected from substituted or unsubstituted $C_{1-4}$ alkyl, OH, $NR_{15}R_{16}$, halogen, $CF_3$, $OCF_3$, CN, substituted or unsubstituted $OC_{1-4}$alkyl, substituted or unsubstituted $OC_{2-4}$ alkyleneOH, $OC_{2-4}$alkyleneNR$_7$R$_8$, substituted or unsubstituted $C_{1-4}$ alkyleneOH, substituted or unsubstituted $C_{1-4}$ alkyleneOC$_{1-4}$ alkyl, substituted or unsubstituted $C_{1-4}$ alkyleneNR$_7$R$_8$, $CONR_7R_8$, $CO_2R_9$, $NR_7COR_9$, $NR_7SO_2C_{1-4}$ alkyl, $N(SO_2C_{1-4}$ alkyl)$_2$, $NR_7CONR_8C_{1-4}$ alkyl, $SO_2NR_9R_{10}$, $OP(O)(OR_7)_2$, $SO_2C_{1-4}$ alkyl, substituted or unsubstituted aryl or substituted or unsubstituted heterocyclyl;
n is 0 to 2;
$R_7$ and $R_8$ are independently selected from H, substituted or unsubstituted $C_{1-4}$ alkyl, substituted or unsubstituted $C_{1-4}$ alkyleneOH, $C_{1-4}$ alkylene $OC_{1-4}$alkyl, $C_{1-4}$alkylene $NR_{15}R_{16}$, $COC_{1-4}$alkyl and substituted or unsubstituted aryl; or
$R_7$ and $R_8$ together with the nitrogen to which they are attached form a 5 to 7 membered heterocyclyl which contains 1 to 2 heteroatoms selected from N, O, S, SO and $SO_2$ which may be substituted with H, $C_{1-4}$ alkyl, $OR_9$ or $NR_9R_{10}$;
$R_9$ and $R_{10}$ are independently selected from H and substituted or unsubstituted $C_{1-4}$ alkyl;
$R_{11}$ is independently selected from H, substituted or unsubstituted $C_{1-4}$ alkyl, substituted or unsubstituted $C_{2-4}$ alkyleneOH and substituted or unsubstituted $C_{2-4}$ alkylene $NR_7R_8$;
$R_{12}$ and $R_{13}$ are independently selected from H, substituted or unsubstituted $C_{1-4}$ alkyl, substituted or unsubstituted aryl, substituted or unsubstituted $C_{2-4}$ alkyleneOH, $COC_{1-4}$ alkyl, COaryl and COheterocyclyl; or
$R_{12}$ and $R_{13}$ together with the nitrogen to which they are attached form a 5 to 7 membered heterocyclyl which contains 1 or 2 heteroatoms selected from N, O, S, SO and $SO_2$ and may be substituted with substituted or unsubstituted $C_{1-4}$ alkyl, $OR_9$ or $NR_9R_{10}$;
$R_{14}$ is selected from aryl or a 5 to 7 membered heterocyclyl having from 1 to 3 heteroatoms selected from N, O, S, SO and SO$_2$, wherein the aryl or heterocyclyl may be substituted with 1 to 3 substituents selected from substituted or unsubstituted C$_{1-4}$ alkyl, OH, NR$_{15}$R$_{16}$, halogen, CF$_3$, OCF$_3$, CN, OC$_{1-4}$alkyl, OC$_{2-4}$ alkyleneOH, C$_{1-4}$ alkylene OH, C$_{1-4}$ alkyleneOC$_{1-4}$ alkyl, C$_{1-4}$ alkyleneNR$_{15}$R$_{16}$, CONR$_{15}$R$_{16}$, CO$_2$R$_9$, NR$_7$SO$_2$CH$_3$, N(SO$_2$CH$_3$)$_2$, NR$_7$CONR$_8$C$_{1-4}$ alkyl, SO$_2$NR$_{15}$R$_{16}$, OP(O)(OR$_7$)$_2$, substituted or unsubstituted aryl and substituted or unsubstituted heterocyclyl;

R$_{15}$ and R$_{16}$ are independently selected from H, substituted or unsubstituted C$_{1-4}$alkyl, substituted or unsubstituted C$_{1-4}$alkylOH, substituted or unsubstituted C$_{1-4}$alkyl OC$_{1-4}$alkyl, COC$_{1-4}$alkyl and S(O)CH$_3$; or R$_{15}$ and R$_{16}$ together with the nitrogen to which they are attached form a 5 to 6 membered heterocyclyl which contains 1 to 2 heteroatoms selected from N, O and S which may be substituted with substituted or unsubstituted C$_{1-4}$ alkyl, OR$_9$ or NR$_9$R$_{10}$, salts, isomers and/or prodrugs thereof.

In one embodiment, the compounds of formula I have the formula Ia

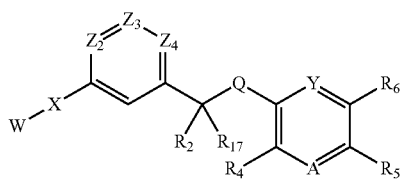

Ia wherein
A, Q, W, Y, X, Z$_1$, Z$_2$, Z$_3$, R$_2$, R$_4$, R$_6$ and R$_{17}$ are as defined above.

Preferably Q is O or NR$_3$ wherein R$_3$ is H or C$_{1-4}$alkyl.

Preferably one of R$_2$ and R$_{18}$ is H and the other is H or C$_{1-4}$alkyl.

Preferably both R$_4$ and R$_5$ are hydrogen,

Preferably both Z$_2$ and Z$_3$ are CH and Z$_4$ is CH or C(CH$_3$) or one of Z$_2$ and Z$_3$ are N and Z$_4$ is CH.

Preferably X is NHCO, NHCH$_2$, NH(CH$_3$)CO, N(CH$_2$CH$_3$)CO, NHSO$_2$, NHCH(CH$_3$), NHCONH, N(CH$_3$)CH(CF$_2$) or NR$_9$ wherein R$_9$ is as defined above.

Preferably W is cyclopropyl, phenyl, a saturated or unsaturated 5 or 6 membered heterocyclyl containing 1 to 2 heteroatoms selected from N, O and S such as pyridinyl, pyrazinyl, piperidinyl, furanyl or pyrazolyl or an unsaturated condensed heterocyclyl containing a nitrogen atom such as indolyl or benzimidazolyl, wherein the cyclopropyl, phenyl or heterocyclyl may be substituted with 1 to 2 substituents independently selected from substituted or unsubstituted C$_{1-4}$alkyl, OH, NO$_2$, NR$_7$R$_8$, halogen, CF$_3$, CO$_2$R$_9$, OC$_{1-4}$alkyl, COR$_9$, SO$_2$ C$_{1-4}$alkyl and a saturated or unsaturated 5 or 6 membered heterocyclyl containing 1 to 2 heteroatoms selected from N, O and S such as piperidinyl, pyrazolyl, piperazinyl, morpholinyl, thiophenyl or imidazolyl, wherein R$_2$, R$_7$, R$_8$ and R$_9$ are as defined above.

In a preferred embodiment, the compounds of formula I and Ia have the formula Ib

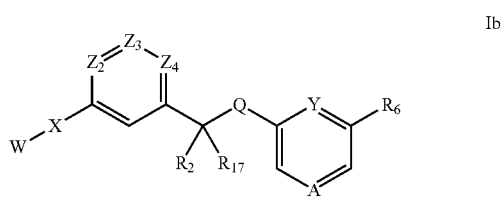

Ib wherein A, Q, W, Y, X, Z$_2$, Z$_3$, Z$_4$, R$_2$, R$_6$ and R$_{17}$ are as defined above.

Preferably one of Y and A is N and the other is NR$_3$ wherein R$_3$ is as defined above or both are N.

Preferably R$_6$ is H, halogen, CO$_2$R$_9$, CONR$_7$R$_8$ or phenyl, saturated or unsaturated 5 or 6 membered heterocyclyl containing 1 to 2 heteroatoms selected from N, O and S such as pyridinyl, pyrazolyl, thiophenyl, morpholinyl, piperidinyl, piperazinyl or imidazolyl or a condensed heterocyclyl containing 1 to 2 oxygen atoms such as 1,3-benzodioxolyl, wherein the phenyl or heterocyclyl may be substituted with 1 to 2 substitutents independently selected from OC$_{1-4}$alkyl, OH, NR$_7$CONR$_8$, NR$_{15}$R$_{16}$, SO$_2$NR$_9$R$_{10}$, OP(O)(OH)$_2$, CO$_2$R$_9$, C$_{1-4}$alkyleneNR$_{15}$R$_{16}$ or substituted or unsubstituted 6 membered heterocyclyl containing 1 to 2 heteroatoms selected from N and O such as piperazinyl, piperidinyl and morpholinyl.

Preferably, when W is substituted, one of the substituents is meta to the atom attached to X.

Preferably, the methylene substituted with R$_2$ and R$_{17}$ is of S chirality.

Table 1 provides non limiting examples of compounds according to the present invention.

TABLE 1

| Compound Number | Structure | $^1$H nmr data (in CDCl$_3$ unless otherwise stated) | Mass spectral data | Synthetic Method |
|---|---|---|---|---|
| 1 | 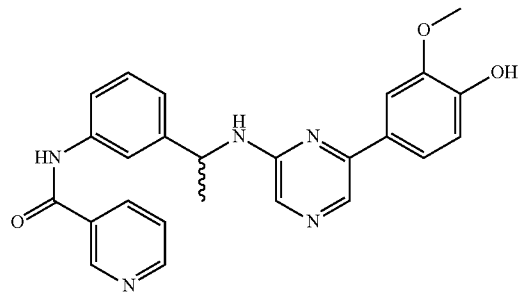 [SMILES: COc1cc(-c2cncc(NC(C)c3cccc(NC(=O)c4cccnc4)c3)n2)ccc1O] | δ 1.60 (d, J 6.8 Hz, 3H), 3.90 (s, 3H), 4.94-5.03 (m, 1H), 5.14 (brd, J 6.2 Hz, 1H), 6.93 (d, J 8.4 Hz, 1H), 7.19-7.54 (m, 6H), 7.65 (s, 1H), 7.73 (brs, 1H), 8.12-8.22 (m, 3H), 8.71 (dd, J 4.8, 1.7 Hz, 1H), 9.06 (d, J 1.8 Hz, 1H) | m/z (ESI) 442 (M$^+$ + 1) | Example 1, 2 |
| 2 | 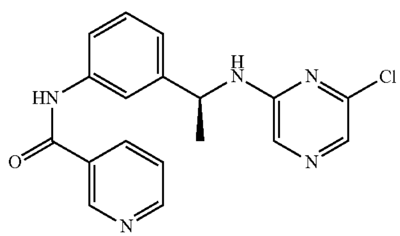 [SMILES: C[C@H](Nc1cncc(Cl)n1)c1cccc(NC(=O)c2cccnc2)c1] | δ 1.58 (d, J 6.9 Hz, 3H), 4.87-4.96 (m, 1H), 5.28 (brd, J 6.9 Hz, 1H), 7.18 (d, J 7.8 Hz, 1H), 7.35 (t, J 7.8 Hz, 1H), 7.40-7.45 (m, 1H), 7.49-7.53 (m, 1H), 7.63 (d, J 0.3 Hz, 1H), 7.72-7.73 (m, 1H), 7.78 (d, J 0.3 Hz, 1H), 8.15 (brs, 1H), 8.17-8.21 (m, 1H), 8.76 (dd, J 5.0, 1.8 Hz, 1H), 9.08-9.09 (m, 1H) | m/z (EI) 353 (M$^+$) | Example 1 |
| 3 | 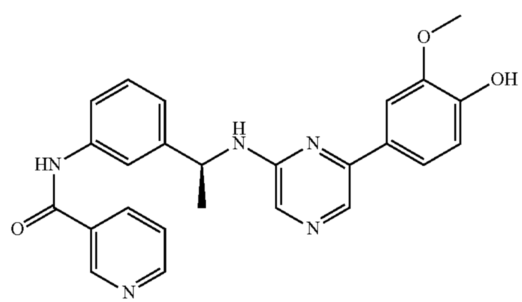 | δ 1.63 (d, J 6.9 Hz, 3H), 3.91 (s, 3H), 4.94-5.03 (m, 1H), 5.14 (brd, J 6.3 Hz, 1H), 6.14 (brs, 1H), 6.94 (d, J 8.4 Hz, 1H), 7.22 (brd, J 7.8 Hz, 1H), 7.31-7.45 (m, 4H), 7.51-7.54 (m, 1H), 7.67 (s, 1H), 7.74 (brs, 1H), 8.14-8.18 (m, 1H), 8.19 (s, 1H), 8.22 (brs, 1H), 8.73 (dd, J 4.8, 1.8 Hz, 1H), 9.07 (d, J 1.8 Hz, 1H) | m/z (EI) 441 (M$^+$) | Example 2 |

TABLE 1-continued

| Compound Number | Structure | ¹H nmr data (in CDCl₃ unless otherwise stated) | Mass spectral data | Synthetic Method |
|---|---|---|---|---|
| 4 | 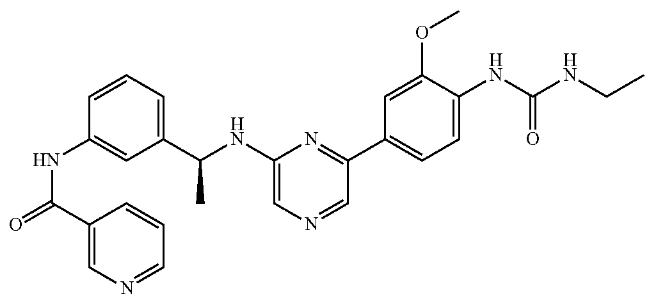 [SMILES: CCNC(=O)Nc1ccc(-c2cncc(N[C@@H](C)c3cccc(NC(=O)c4cccnc4)c3)n2)cc1OC] | δ 1.04 (t, J 7.2 Hz, 3H), 1.51 (d, J 6.9 Hz, 3H), 3.05-3.14 (m, 2H), 3.84 (s, 3H), 6.87 (d, J 0.6 Hz, 1H), 7.21 (brd, J 7.8 Hz, 1H), 7.30 (t, J 7.8 Hz, 1H), 7.45-7.62 (m, 5H), 7.86-7.94 (m, 3H), 8.14 (d, J 9.0 Hz, 1H), 8.21 (s, 1H), 8.26-8.30 (m, 1H), 8.74 (dd, J 4.8, 1.8 Hz, 1H), 9.08 (dd, J 2.1, 0.9 Hz, 1H), 10.38 (s, 1H) | m/z (EI) 511 (M⁺) | Example 2 |
| 5 | 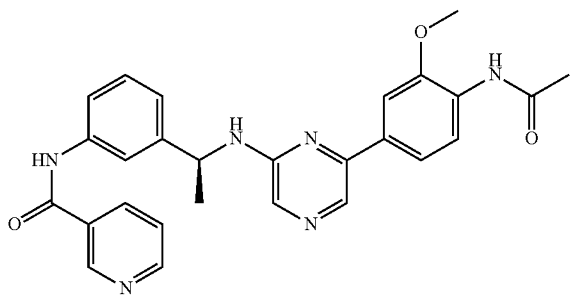 [SMILES: COc1cc(-c2cncc(N[C@@H](C)c3cccc(NC(=O)c4cccnc4)c3)n2)ccc1NC(C)=O] | d6 DMSO δ 1.61 (d, J 6.9 Hz, 3H), 2.19 (s, 3H), 3.90 (s, 3H), 4.94-5.03 (m, 1H), 5.21 (brd, J 6.0 Hz, 1H), 7.21 (brd, J 8.4 Hz, 1H), 7.30-7.45 (m, 4H), 7.53-7.56 (m, 1H), 7.70 (s, 1H), 7.74 (brs, 1H), 7.82 (brs, 1H), 8.14-8.18 (m, 1H), 8.20 (s, 1H), 8.37 (brd, J 8.7 Hz, 1H), 8.44 (brs, 1H), 8.71 (dd, J 4.8, 1.8 Hz, 1H), 9.07 (d, J 2.4 Hz, 1H) | m/z (EI) 482 (M⁺) | Example 2 |
| 6 | 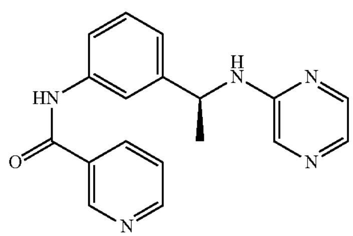 [SMILES: C[C@H](Nc1cnccn1)c1cccc(NC(=O)c2cccnc2)c1] | δ 1.58 (d, J 6.9 Hz, 3H), 4.89-4.98 (m, 1H), 5.10 (d, J 6.3 Hz, 1H), 7.18 (brd, J 7.5 Hz, 1H), 7.34 (t, J 7.8 Hz, 1H), 7.39-7.44 (m, 1H), 7.51-7.55 (m, 1H), 7.69 (brs, 1H), 7.77-7.95 (m, 2H), 7.94-7.95 (m, 1H,), 8.16-8.24 (m, 2H), 8.75 (dd, J 4.8, 1.5 Hz, 1H), 9.07 (d, J 2.4 Hz, 1H) | m/z (EI) 319 (M⁺) | Example 2 (byproduct) |

TABLE 1-continued

| Compound Number | Structure | $^1$H nmr data (in CDCl$_3$ unless otherwise stated) | Mass spectral data | Synthetic Method |
|---|---|---|---|---|
| 7 | (structure) | δ 1.61 (d, J 6.6 Hz, 3H), 3.89 (s, 3H), 3.99 (brs, 2H), 4.95-5.02 (m, 1H), 5.07 (brd, J 6.0 Hz, 1H), 6.71 (d, J 8.1 Hz, 1H), 7.22-7.24 (m, 1H), 7.31-7.42 (m, 4H), 7.52-7.55 (m, 1H), 7.62 (s, 1H), 7.71 (brs, 1H), 8.14-8.18 (m, 2H), 8.19 (s, 1H), 8.74 (dd, J 4.8, 1.8 Hz, 1H) 9.07 (dd, J 2.1, 0.6 Hz, 1H) | m/z (EI) 440 (M$^+$) | Example 2 |
| 8 | (structure) | δ 1.63 (d, J 6.9 Hz, 3H), 3.42 & 3.43 (both s, 3H), 3.91 (s, 3H, ), 4.98-5.07 (m, 1H) 5.19 (brd, J 6.0 Hz, 1H), 7.20-7.53 (m, 7H), 7.78 (brs, 1H), 7.82 (s, 1H), 8.06 (s, 1H, ), 8.14-8.18 (m, 1H), 8.24 (s, 1H, ), 8.73-8.75 (dd, J 4.8, 1.5 Hz, 1H), 9.06 (d, J 1.8 Hz, 1H) | m/z (EI) 596 (M$^+$) | Example 3 |
| 9 | (structure) | δ 1.63 (d, J 6.6 Hz, 3H), 2.97 (s, 3H), 3.90 (s, 3H), 4.96-5.05 (m, 1H), 5.19 (d, J 5.4 Hz, 1H), 6.94 (s, 1H), 7.21-7.24 (m, 1H), 7.31-7.56 (m, 6H), 7.76 (s, 1H), 7.79 (brs, 1H), 8.15-8.18 (m, 2H), 8.22 (s, 1H), 8.74 (brd, J 4.8 Hz, 1H), 9.06 (d, J 2.1 Hz, 1H) | m/z (EI) 518 (M$^+$) | Example 3 |

TABLE 1-continued

| Compound Number | Structure | ¹H nmr data (in CDCl₃ unless otherwise stated) | Mass spectral data | Synthetic Method |
|---|---|---|---|---|
| 10 | 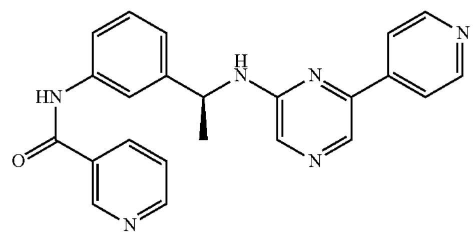 [SMILES: C[C@H](Nc1cncc(-c2ccncc2)n1)c1cccc(NC(=O)c2cccnc2)c1] | δ 1.64 (d, J 6.9 Hz, 3H), 5.02-5.12 (m, 1H), 5.35 (d, J 6.6 Hz, 1H), 7.24 (brd, J 7.5 Hz, 1H), 7.33-7.48 (m, 3H), 7.76 (d, J 6.3 Hz, 2H), 7.86 (brs, 2H), 8.16-8.20 (m, 1H), 8.30 (s, 1H), 8.37 (brs, 1H), 8.65 (d, J 6.3 Hz, 2H), 8.74 (dd, J 4.8, 1.5 Hz, 1H), 9.08 (d, J 1.5 Hz, 1H) | m/z (EI) 396 (M⁺) | Example 2 |
| 11 | 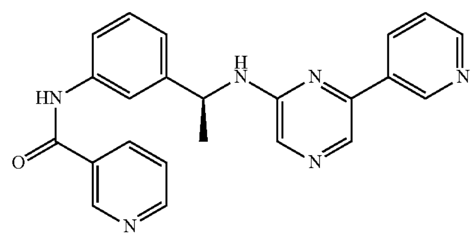 [SMILES: C[C@H](Nc1cncc(-c2cccnc2)n1)c1cccc(NC(=O)c2cccnc2)c1] | δ 1.62 (d, J 6.9 Hz, 3H), 5.01-5.10 (m, 1H), 5.36 (d, J 6.3 Hz, 1H), 7.22 (brd, J 7.8 Hz, 1H), 7.32-7.41 (m, 3H), 7.50-7.53 (m, 1H), 7.79 (brs, 1H), 7.81 (s, 1H), 8.13-8.21 (m, 2H), 8.23 (s, 1H), 8.51 (brs, 1H), 8.60 (dd, J 4.8, 1.5 Hz, 1H), 8.72 (dd, J 4.8, 1.8 Hz, 1H), 9.06 (d, J 1.8 Hz, 1H), 9.10 (s, 1H) | m/z (EI) 396 (M⁺) | Example 2 |
| 12 | 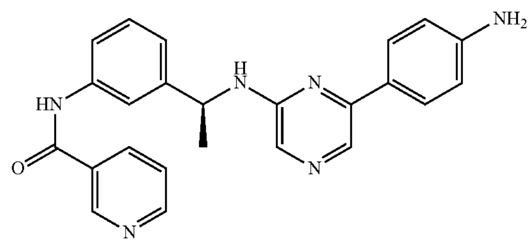 [SMILES: C[C@H](Nc1cncc(-c2ccc(N)cc2)n1)c1cccc(NC(=O)c2cccnc2)c1] | δ 1.60 (d, J 6.6 Hz, 3H), 3.86 (brs, 2H), 4.94-5.03 (m, 1H), 5.08 (d, J 6.3 Hz, 1H), 6.70 (d, J 8.7 Hz, 2H), 7.22 (brd, J 7.5 Hz, 1H), 7.31-7.40 (m, 2H), 7.53-7.56 (m, 1H), 7.59 (s, 1H), 7.69 (brs, 1H), 7.73 (d, J 8.7 Hz, 2H), 8.14-8.17 (m, 1H), 8.16 (s, 1H), 8.28 (brs, 1H), 8.73 (dd, J 4.8, 1.8 Hz, 1H), 9.06 (d, J 1.8 Hz, 1H) | m/z (EI) 410 (M⁺) | Example 2 |
| 13 | 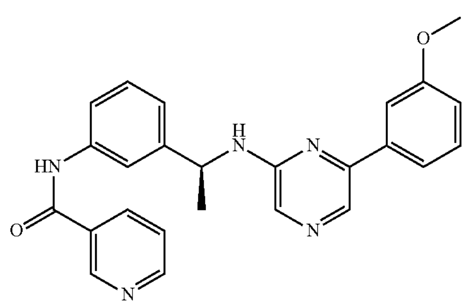 [SMILES: COc1cccc(-c2cncc(N[C@@H](C)c3cccc(NC(=O)c4cccnc4)c3)n2)c1] | δ 1.61 (d, J 6.9 Hz, 3H), 3.83 (s, 3H), 4.97-5.06 (m, 1H), 5.20 (brd, J 6.3 Hz, 1H), 6.92 (ddd, J 8.3, 2.5, 0.9 Hz, 1H), 7.21-7.25 (m, 1H), 7.30-7.41 (m, 3H), 7.41-7.44 (m, 2H), 7.52-7.56 (m, 1H), 7.73 (brs, 2H), 8.14-8.18 (m, 1H), 8.24 (s, 1H), 8.25 (brs, 1H), 8.73 (dd, J 4.8, 1.5 Hz, 1H), 9.07 (d, J 1.8 Hz, 1H) | m/z (EI) 425 (M⁺) | Example 2 |

TABLE 1-continued

| Compound Number | Structure | 1H nmr data (in CDCl3 unless otherwise stated) | Mass spectral data | Synthetic Method |
|---|---|---|---|---|
| 14 | 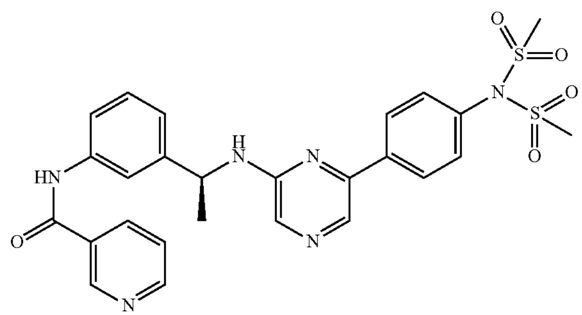 [SMILES: C[C@H](Nc1cncc(-c2ccc(N(S(C)(=O)=O)S(C)(=O)=O)cc2)n1)c1cccc(NC(=O)c2cccnc2)c1] | δ 1.64 (d, J 6.6 Hz, 3H), 3.41 (s, 6H), 5.01-5.10 (m, 1H), 5.13 (d, J 6.3 Hz, 1H), 7.23 (brd, J 7.8 Hz, 1H), 7.34-7.49 (m, 5H), 7.80 (m, 2H), 7.95-7.98 (m, 3H), 8.16-8.20 (m, 1H), 8.26 (s, 1H), 8.76 (brd, J 3.9 Hz, 1H), 9.08 (brs, 1H) | m/z (EI) 566 (M+) | Example 3 |
| 15 | 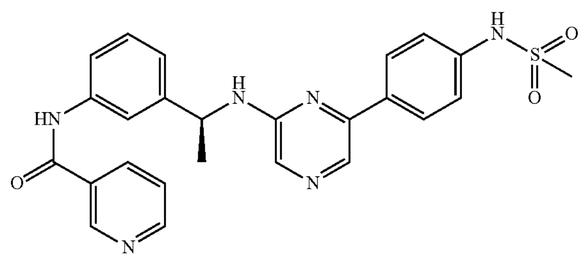 [SMILES: C[C@H](Nc1cncc(-c2ccc(NS(C)(=O)=O)cc2)n1)c1cccc(NC(=O)c2cccnc2)c1] | CDCl3 + CD3OD δ 1.62 (d, J 6.9 Hz, 3H), 3.00 (s, 3H), 5.01-5.08 (m, 1H), 7.21-7.37 (m, 4H), 7.42-7.47 (m, 1H), 7.54-7.57 (m, 1H), 7.73 (s, 1H), 7.80 (brs, 1H), 7.85 (d, J 8.7 Hz, 2H), 8.15 (s, 1H), 8.24-8.28 (m, 1H), 8.71 (brd, J 4.8 Hz, 1H), 9.06 (brs, 1H) | m/z (EI) 488 (M+) | Example 3 |
| 16 | 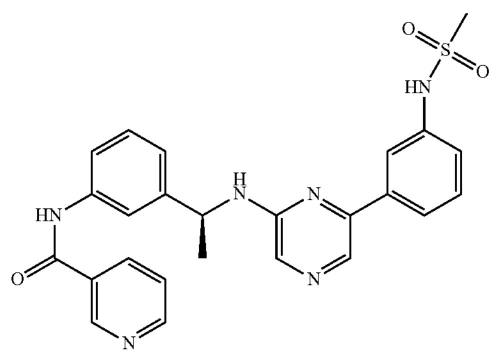 [SMILES: C[C@H](Nc1cncc(-c2cccc(NS(C)(=O)=O)c2)n1)c1cccc(NC(=O)c2cccnc2)c1] | δ 1.58 (d, J 6.9 Hz, 3H), 2.97 (s, 3H), 5.15-5.22 (m, 1H), 5.24 (d, J 6.9 Hz, 1H), 7.20 (brd, J 7.8 Hz, 1H), 7.29-7.44 (m, 5H), 7.61-7.64 (m, 1H), 7.83 (s, 1H), 7.94 (brs, 1H), 8.05 (brs, 1H), 8.24 (s, 1H), 8.31 (brs, 1H), 8.33-8.37 (m, 1H), 8.63 (brs, 1H), 8.71 (dd, J 4.8, 1.5 Hz, 1H), 9.11 (d, J 1.8 Hz, 1H) | m/z (EI) 488 (M+) | Example 2 |

TABLE 1-continued

| Compound Number | Structure | ¹H nmr data (in CDCl₃ unless otherwise stated) | Mass spectral data | Synthetic Method |
|---|---|---|---|---|
| 17 | 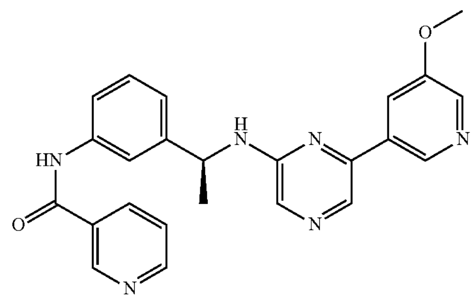 [SMILES: COc1cncc(-c2cncc(N[C@@H](C)c3cccc(NC(=O)c4cccnc4)c3)n2)c1] | δ 1.61 (d, J 6.9 Hz, 3H), 3.87 (s, 3H), 4.98-5.07 (m, 1H), 5.31 (d, J 6.0 Hz, 1H), 7.22 (d, J 7.8 Hz, 1H), 7.31-7.41 (m, 2H), 7.52 (brd, J 7.8 Hz, 1H), 7.65 (m, 1H), 7.77 (brs, 1H), 7.81 (s, 1H), 8.16-8.20 (m, 1H), 8.23 (s, 1H), 8.29 (d, J 2.7 Hz, 1H), 8.39 (brs, 1H), 8.68 (d, J 1.5 Hz, 1H), 8.73 (dd, J 4.8, 1.5 Hz, 1H), 9.08 (d, J 1.8 Hz, 1H) | m/z (EI) 426 (M⁺) | Example 2 |
| 18 | 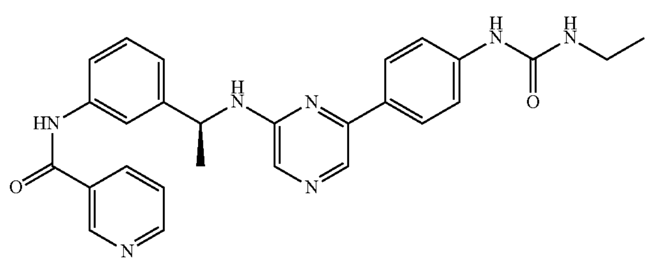 [SMILES: CCNC(=O)Nc1ccc(-c2cncc(N[C@@H](C)c3cccc(NC(=O)c4cccnc4)c3)n2)cc1] | CDCl₃ + CD₃OD δ 1.06 (t, J 7.2 Hz, 3H), 1.52 (d, J 6.9 Hz, 3H), 3.17 (m, 2H), 4.89-4.95 (m, 1H), 7.12 (brd, J 7.5 Hz, 1H), 7.22-7.38 (m, 5H) 7.49-7.52 (m, 1H), 7.56 (s, 1H), 7.65-7.69 (m, 3H), 8.01 (s, 1H), 8.15-8.19 (m, 1H), 8.60 (dd, J 4.9, 1.5 Hz, 1H), 8.97 (d, J 2.1 Hz, 1H) | m/z (ESI) 482 (M⁺ + 1) | Example 2 |
| 19 | 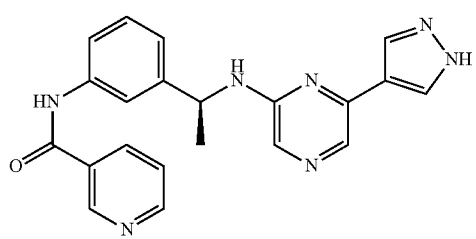 [SMILES: C[C@H](Nc1cncc(-c2cn[nH]c2)n1)c1cccc(NC(=O)c2cccnc2)c1] | CD₃OD δ 1.59 (d, J 6.9 Hz, 3H), 5.06-5.13 (m, 1H), 7.25-7.28 (m, 1H), 7.34 (t, J 7.8 Hz, 1H), 7.50-7.59 (m, 2H), 7.67 (s, 1H), 7.85 (brs, 1H), 7.92 (s, 1H), 8.04 (brs, 2H), 8.32-8.36 (m, 1H), 8.71 (dd, J 4.8, 1.5 Hz, 1H), 9.07 (d, J 1.8 Hz, 1H) | m/z (EI) 385 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 20 | 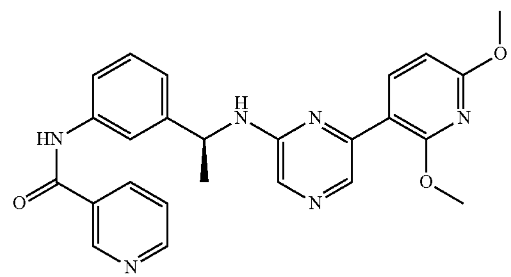 [SMILES: COc1ccc(-c2cncc(N[C@@H](C)c3cccc(NC(=O)c4cccnc4)c3)n2)c(OC)n1] | δ 1.59 (d, J 6.3 Hz, 3H), 3.94 (s, 3H), 3.99 (s, 3H,), 4.90-4.99 (m, 2H), 6.38 (d, J 8.4 Hz, 1H), 7.18-7.21 (m, 1H), 7.33 (t, J 7.8 Hz, 1H) 7.36-7.41 (m, 1H), 7.49-7.53 (m, 1H), 7.62 (s, 1H), 7.69 (m, 1H), 8.03 (brs, 1H), 8.13 (d, J 8.4 Hz, 1H), 8.13-8.17 (m, 1H), 8.53 (s, 1H), 8.73 (dd, J 4.8, 1.8 Hz, 1H), 9.06 (dd, J 2.3, 0.9 Hz, 1H) | m/z (EI) 456 (M⁺) | Example 2 |
| 21 | 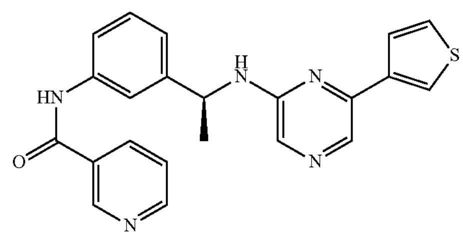 [SMILES: C[C@H](Nc1cncc(-c2ccsc2)n1)c1cccc(NC(=O)c2cccnc2)c1] | δ 1.63 (d, J 6.6 Hz, 3H), 4.99-5.08 (m, 2H), 7.22-7.26 (m, 1H), 7.34-7.44 (m, 3H), 7.49-7.53 (m, 1H), 7.55 (dd, J 5.1, 1.2 Hz, 1H), 7.68 (s, 1H), 7.77 (m, 1H), 7.85 (dd, J 3.0, 1.2 Hz, 1H), 8.00 (brs, 1H), 8.16 (s, 1H), 8.17-8.21 (m, 1H), 8.76 (dd, J 4.8, 1.5 Hz, 1H), 9.08 (dd, J 2.2, 0.9 Hz, 1H) | m/z (EI) 401 (M⁺) | Example 2 |
| 22 | 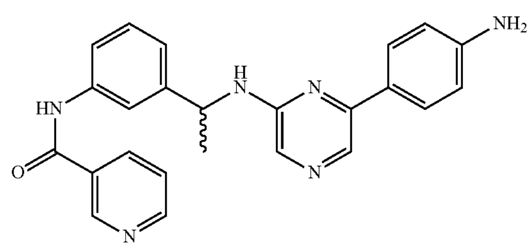 [SMILES: CC(Nc1cncc(-c2ccc(N)cc2)n1)c1cccc(NC(=O)c2cccnc2)c1] | Racemic version of Compound 12 Same spectral data | | Example 2 |

TABLE 1-continued

| Compound Number | Structure | ¹H nmr data (in CDCl₃ unless otherwise stated) | Mass spectral data | Synthetic Method |
|---|---|---|---|---|
| 23 | (structure: morpholine–phenyl–pyrazine–NH–CH(CH₃)–phenyl–NHC(O)–pyridin-3-yl) | δ 1.60 (d, J 6.6 Hz, 3H), 3.21 (t, J 1.8 Hz, 4H), 4.95-5.04 (m, 1H), 5.12 (d, J 6.3 Hz, 1H), 6.92 (d, J 9.0 Hz, 2H), 7.22 (brd, J 7.8 Hz, 1H), 7.31-7.39 (m, 2H), 7.52-7.56 (m, 1H), 7.62 (s, 1H), 7.73 (brs, 1H), 7.83 (d, J 9.0 Hz, 2H), 8.14-8.18 (m, 1H), 8.19 (s, 1H), 8.33 (brs, 1H), 8.72 (d, J 5.7 Hz, 1H), 9.07 (d, J 1.8 Hz, 1H) | m/z (EI) 480 (M⁺) | Example 2 |
| 24 | (structure: 3-methoxyphenyl–pyrazine–NH–CH(CH₃)–phenyl–NHC(O)–5-methylpyridin-3-yl) | δ 1.63 (d, J 6.6 Hz, 3H), 2.40 (s, 3H), 3.84 (s, 3H), 4.98-5.07 (m, 1H), 5.16 (d, J 6.3 Hz, 1H), 6.94 (ddd, J 8.1, 2.4, 1.2 Hz, 1H), 7.22-7.25 (m, 1H), 7.31-7.38 (m, 2H), 7.45-7.49 (m, 2H), 7.53-7.57 (m, 1H), 7.73 (brt, J 1.8 Hz, 1H), 7.75 (s, 1H), 7.95-8.00 (m, 1H), 8.06 (brs, 1H), 8.26 (s, 1H), 8.58 (d, J 1.5 Hz, 1H), 8.87 (d, J 1.8 Hz, 1H) | m/z (EI) 439 (M⁺) | Example 2 |
| 25 | (structure: 3-methoxyphenyl–pyrazine–NH–CH(CH₃)–phenyl–NHC(O)–pyridin-2-yl) | δ 1.66 (d, J 6.6 Hz, 3H), 3.85 (s, 3H), 5.03-5.08 (m, 2H), 6.93-6.97 (m, 1H), 7.20-7.24 (m, 1H), 7.32-7.39 (m, 2H), 7.47-7.52 (m, 3H), 7.65-7.69 (m, 1H), 7.78 (s, 1H), 7.89-7.95 (m, 2H), 8.28 (d, J 0.3 Hz, 1H), 8.29-8.32 (m, 1H), 8.62 (ddd, J 4.8, 1.8, 0.9 Hz, 1H), 10.05 (brs, 1H) | m/z (EI) 425 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 26 | 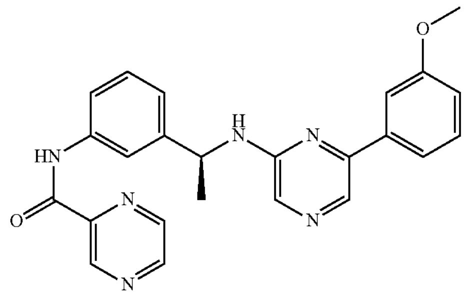 [SMILES: COc1cccc(-c2cncc(N[C@@H](C)c3cccc(NC(=O)c4cnccn4)c3)n2)c1] | δ 1.65 (d, J 6.6 Hz, 3H), 3.84 (s, 3H), 5.02-5.10 (m, 2H), 6.92-6.96 (m, 1H), 7.23-7.26 (m, 1H), 7.31-7.40 (m, 2H), 7.47-7.50 (m, 2H), 7.62-7.66 (m, 1H), 7.76 (s, 1H), 7.87 (brt, J 1.8 Hz, 1H), 8.27 (s, 1H), 8.57 (dd, J 2.4, 1.5 Hz, 1H), 8.80 (d, J 2.4 Hz, 1H), 9.51 (d, J 1.5 Hz, 1H), 9.67 (brs, 1H) | m/z (EI) 426 (M⁺) | Example 2 |
| 27 | 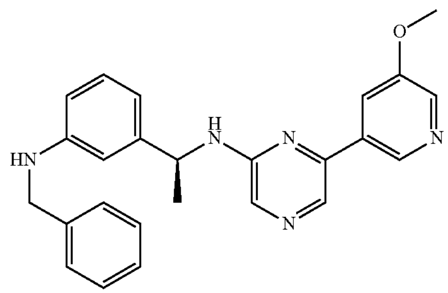 [SMILES: COc1cncc(-c2cncc(N[C@@H](C)c3cccc(NCc4ccccc4)c3)n2)c1] | δ 1.57 (d, J 6.6 Hz, 3H), 3.88 (s, 3H), 4.29 (s, 2H), 4.84-4.93 (m, 1H), 5.08 (d, J 6.3 Hz, 1H), 6.52 (ddd, J 7.8, 2.4, 0.9 Hz, 1H), 6.66 (brt, J 1.8 Hz, 1H), 6.74 (brd, J 7.8 Hz, 1H), 7.13 (t, J 7.8 Hz, 1H), 7.23-7.31 (m, 5H), 7.67-7.71 (m, 1H), 7.77 (s, 1H), 8.26 (s, 1H), 8.32 (d, J 2.7 Hz, 1H), 8.74 (d, J 1.5 Hz, 1H) | m/z (EI) 411 (M⁺) | Example 2, 4 |
| 28 | 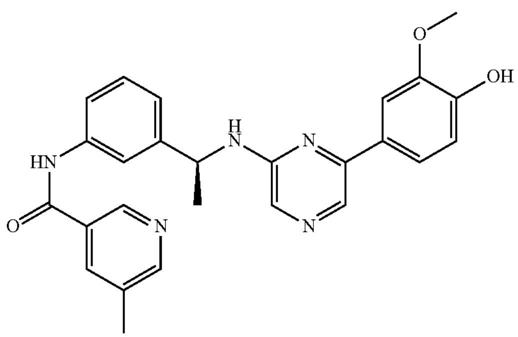 [SMILES: COc1cc(-c2cncc(N[C@@H](C)c3cccc(NC(=O)c4cncc(C)c4)c3)n2)ccc1O] | δ 1.63 (d, J 6.9 Hz, 3H), 2.40 (s, 3H), 3.92 (s, 3H), 4.94-5.03 (m, 1H), 5.12 (d, J 6.0 Hz, 1H), 6.01 (s, 1H), 6.95 (d, J 8.1 Hz, 1H), 7.23 (brd, J 7.8 Hz, 1H), 7.35 (t, J 7.8 Hz, 1H), 7.40-7.45 (m, 2H), 7.51-7.54 (m, 1H), 7.68 (s, 1H), 7.74 (brs, 1H), 7.98 (brs, 1H), 8.07 (s, 1H), 8.21 (s, 1H), 8.57 (d, J 1.5 Hz, 1H), 8.86 (d, J 1.8 Hz, 1H) | m/z (EI) 455 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 29 | 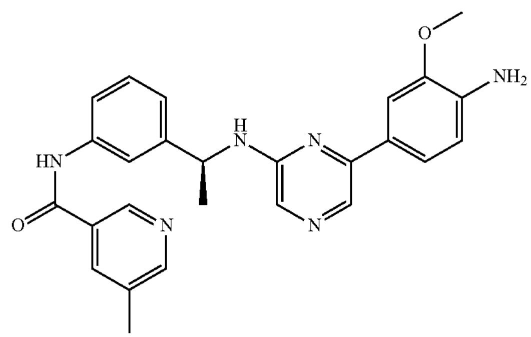 [SMILES: COc1cc(-c2cncc(N[C@@H](C)c3cccc(NC(=O)c4cncc(C)c4)c3)n2)ccc1N] | δ 1.63 (d, J 6.6 Hz, 3H), 2.41 (s, 3H), 3.90 (s, 3H), 4.93-5.02 (m, 1H), 5.06 (d, J 6.0 Hz, 1H), 6.72 (d, J 8.1 Hz, 1H), 7.23 (brd, J 7.5 Hz, 1H), 7.32-7.26 (m, 3H), 7.53-7.56 (m, 1H), 7.63 (s, 1H), 7.71 (brs, 1H), 7.98 (brs, 2H), 8.20 (s, 1H), 8.58 (d, J 2.1 Hz, 1H), 8.87 (d, J 2.1 Hz, 1H) | m/z (EI) 454 (M⁺) | Example 2 |
| 30 | 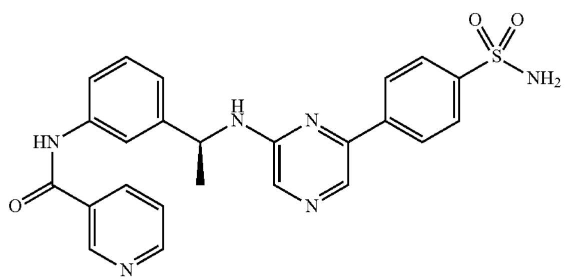 [SMILES: C[C@H](Nc1cncc(-c2ccc(S(N)(=O)=O)cc2)n1)c1cccc(NC(=O)c2cccnc2)c1] | CD₃OD δ 1.60 (d, J 6.9 Hz, 3H), 5.08-5.15 (m, 1H), 7.25-7.36 (m, 2H), 7.44-7.76 (m, 2H), 7.86-7.93 (m, 4H), 8.02-8.08 (m, 2H), 8.17 (s, 1H), 8.31-8.35 (m, 1H), 8.70 (dd, J 4.8, 1.5 Hz, 1H), 9.06 (d, J 2.1 Hz, 1H) | m/z (EI) 474 (M⁺) | Example 2 |
| 31 | 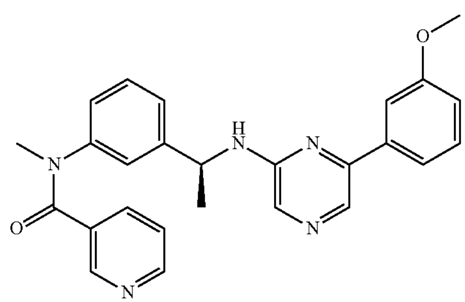 [SMILES: COc1cccc(-c2cncc(N[C@@H](C)c3cccc(N(C)C(=O)c4cccnc4)c3)n2)c1] | δ 1.41 (d, J 6.6 Hz, 3H), 3.49 (s, 3H), 3.85 (s, 3H), 4.82-4.91 (m, 1H), 4.95 (d, J 6.0 Hz, 1H), 6.90 (ddd, J 7.8, 4.8, 0.9 Hz, 1H), 6.96 (ddd, J 8.1, 2.7, 1.2 Hz, 1H), 6.98-7.02 (m, 2H), 7.21-7.26 (m, 2H), 7.33-7.35 (m, 1H), 7.42-7.47 (m, 3H), 7.62 (s, 1H), 8.29 (d, J 0.3 Hz, 1H) 8.33 (dd, J 4.8, 1.8 Hz, 1H), 8.46 (dd, J 2.7, 0.9 Hz, 1H) | m/z (EI) 439 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 32 | 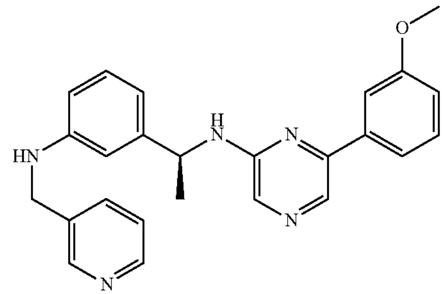 [SMILES: COc1cccc(-c2cncc(N[C@@H](C)c3cccc(NCc4cccnc4)c3)n2)c1] | δ 1.58 (d, J 6.6 Hz, 3H), 3.85 (s, 3H), 4.33 (s, 2H), 4.85-4.94 (m, 1H), 5.07 (d, J 6.3 Hz, 1H), 6.51 (ddd, J 8.1, 2.4, 0.9 Hz, 1H), 6.68-6.70 (m, 1H), 6.79 (brd, J 7.5 Hz, 1H), 6.94-6.97 (m, 1H), 7.15 (t, J 7.8 Hz, 1H), 7.21 (ddd, J 7.8, 4.8, 0.9 Hz, 1H), 7.35 (t, J 8.1 Hz, 1H), 7.48 (m, 2H), 7.62-7.66 (m, 1H), 7.70 (s, 1H), 8.26 (s, 1H), 8.50 (dd, J 4.8, 1.8 Hz, 1H), 8.60 (d, J 2.4 Hz, 1H) | m/z (EI) 411 (M⁺) | Example 2, 4 |
| 33 | 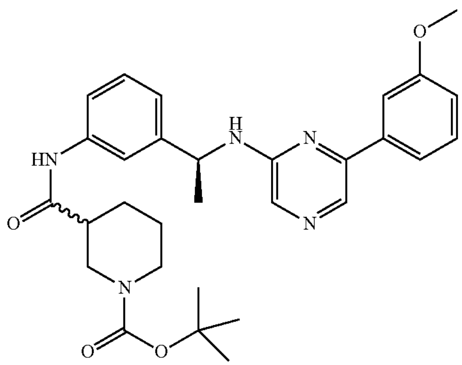 [SMILES: COc1cccc(-c2cncc(N[C@@H](C)c3cccc(NC(=O)C4CCCN(C(=O)OC(C)(C)C)C4)c3)n2)c1] | δ 1.43 & 1.44 (2 x s, 9H), 1.56 (d, J 6.9 Hz, 3H), 1.57-1.70 (brs, 1H), 1.84-2.00 (brs, 2H), 2.26-2.54 (m, 2H), 2.94-3.17 (brs, 1H), 3.25-3.46 (brs, 1H), 3.64-3.78 (brs, 1H), 3.84 (s, 3H), 3.87-4.00 (brs, 1H), 4.92-5.01 (m, 1H), 5.23 (brs, 1H), 6.94 (ddd, J 8.1, 2.4, 0.9 Hz, 1H), 7.13 (brd, J 7.5 Hz, 1H), 7.23 (t, J 7.8 Hz, 1H), 7.33 (t, J 8.1 Hz, 1H), 7.42-7.71 (m, 4H), 7.72 (s, 1H), 8.24 (s, 1H), 8.49 (brs, 1H) | m/z (EI) 531 (M⁺) | Example 2 |
| 34 | 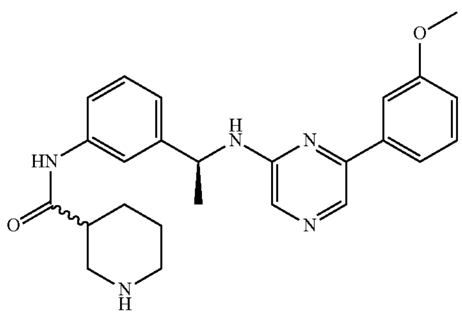 [SMILES: COc1cccc(-c2cncc(N[C@@H](C)c3cccc(NC(=O)C4CCCNC4)c3)n2)c1] | δ 1.53-1.59 (m, 1H), 1.62 (d, J 6.9 Hz, 3H), 1.71-1.82 (m, 2H), 2.08 (brs, 1H), 2.52-2.54 (m, 1H), 2.70-2.78 (m, 1H), 2.90-2.95 (m, 1H), 3.05-3.08 (m, 1H), 3.23-3.27 (m, 1H), 3.87 (s, 3H), 4.95-5.04 (m, 1H), 5.09 (d, J 6.3 Hz, 1H), 6.96 (ddd, J 8.1, 2.4, 0.9 Hz, 1H), 7.14 (brd, J 7.8 Hz, 1H), 7.28 (t, J 7.8 Hz, 1H), 7.35 (t, J 8.1 Hz, 1H), 7.40-7.46 (m, 1H), 7.49-7.51 (m, 2H), 7.71 (dt, J 7.2, 1.8 Hz, 1H), 7.75 (s, 1H), 8.26 (d, J 0.3 Hz, 1H), 10.50 (brs, 1H) | m/z (EI) 431 (M⁺) | Example 5 |

TABLE 1-continued

| Compound Number | Structure | ¹H nmr data (in CDCl₃ unless otherwise stated) | Mass spectral data | Synthetic Method |
|---|---|---|---|---|
| 35 | 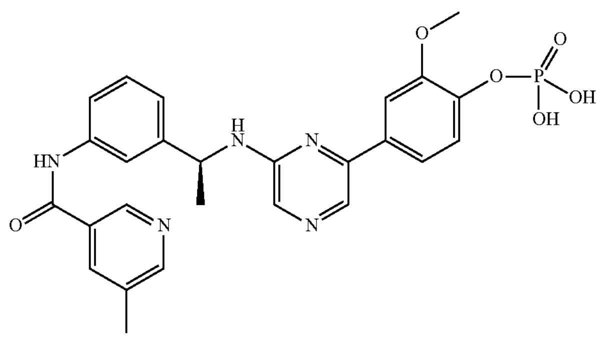 [SMILES: COc1cc(-c2cncc(N[C@@H](C)c3cccc(NC(=O)c4cncc(C)c4)c3)n2)ccc1OP(=O)(O)O] | CD₃OD δ 1.60 (d, J 6.9 Hz, 3H), 2.45 (s, 3H), 3.80 (s, 3H), 5.08-5.15 (m, 1H), 7.25-7.35 (m, 2H), 7.38-7.45 (m, 2H), 7.54-7.57 (m, 1H), 7.65 (d, J 8.4 Hz, 1H), 7.76 (s, 1H), 7.80 (s, 1H), 8.08 (s, 1H), 8.16 (s, 1H), 8.56 (s, 1H), 8.86 (s, 1H) | m/z (ESI, −ve) 534 (M⁺ − 1) | Example 6 |
| 36 | 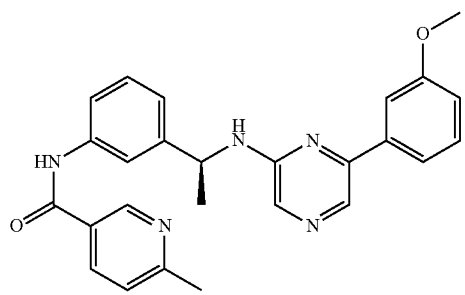 [SMILES: COc1cccc(-c2cncc(N[C@@H](C)c3cccc(NC(=O)c4ccc(C)nc4)c3)n2)c1] | δ 1.60 (d, J 6.9 Hz, 3H), 2.60 (s, 3H), 3.83 (s, 3H), 4.96-5.05 (m, 1H), 5.21 (brs, 1H), 6.93 (dd, J 8.1, 2.4 Hz, 1H), 7.21 (d, J 7.8 Hz, 2H), 7.30-7.36 (m, 2H), 7.45-7.47 (m, 2H), 7.52 (d, J 7.2 Hz, 1H), 7.72 (s, 1H), 7.73 (s, 1H), 8.05 (dd, J 8.1, 2.4 Hz, 1H), 8.23 (s, 1H), 8.26 (brs, 1H), 8.96 (d, J 2.1 Hz, 1H) | m/z (EI) 439 (M⁺) | Example 2 |
| 37 | 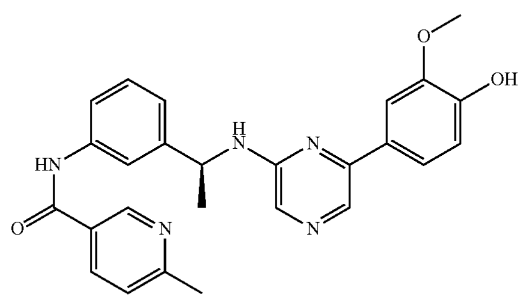 [SMILES: COc1cc(-c2cncc(N[C@@H](C)c3cccc(NC(=O)c4ccc(C)nc4)c3)n2)ccc1O] | δ 1.63 (d, J 6.6 Hz, 3H), 2.63 (s, 3H), 3.93 (s, 3H), 4.97-5.02 (m, 1H), 5.08 (d, J 6.0 Hz, 1H), 6.96 (d, J 8.1 Hz, 1H), 7.21-7.28 (m, 2H), 7.32-7.52 (m, 6H), 7.68 (s, 1H), 7.75 (t, J 1.8 Hz, 1H), 7.93 (s, 1H), 8.07 (dd, J 8.1, 2.4 Hz, 1H), 8.21 (s, 1H), 8.95 (d, J 2.1 Hz, 1H) | m/z (EI) 455 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 38 | 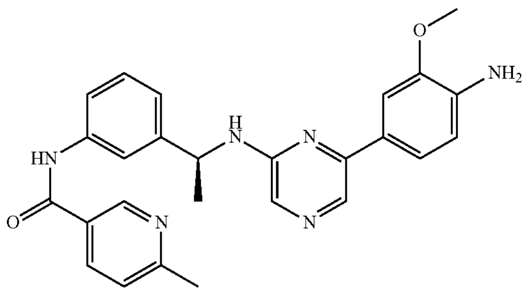 [SMILES: COc1cc(-c2cncc(N[C@@H](C)c3cccc(NC(=O)c4ccc(C)nc4)c3)n2)ccc1N] | δ 1.62 (d, J 6.6 Hz, 3H), 2.63 (s, 3H), 3.90 (s, 3H), 4.93-5.04 (m, 2H), 6.72 (d, J 8.1 Hz, 1H), 7.21-7.24 (m, 2H), 7.31-7.38 (m, 2H), 7.41 (d, J 1.8 Hz, 1H), 7.50-7.53 (m, 2H), 7.63 (brs, 1H), 7.72 (t, J 1.8 Hz, 1H), 7.94 (s, 1H), 8.06 (dd, J 8.1, 2.4 Hz, 1H), 8.20 (s, 1H), 8.96 (d, J 2.1 Hz, 1H) | m/z (EI) 454 (M⁺) | Example 2 |
| 39 | 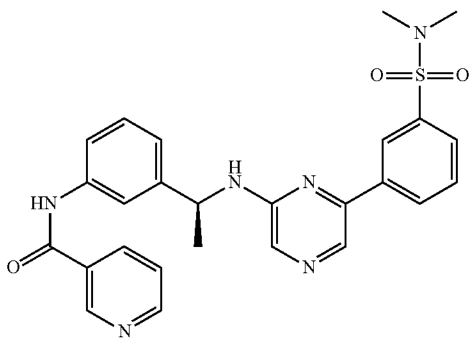 [SMILES: C[C@H](Nc1cncc(-c2cccc(S(=O)(=O)N(C)C)c2)n1)c1cccc(NC(=O)c2cccnc2)c1] | δ 1.60 (d, J 6.9 Hz, 3H), 2.69 (s, 6H), 5.00-5.09 (m, 1H), 5.42 (d, J 6.0 Hz, 1H), 7.20 (d, J 7.8 Hz, 1H), 7.34 (t, J 7.8 Hz, 1H), 7.41 (ddd, J 8.1, 4.8, 0.9 Hz, 1H), 7.55-7.60 (m, 2H), 7.71-7.75 (m, 1H), 7.81-7.84 (m, 1H), 7.90 (s, 1H), 8.04-8.08 (m, 1H), 8.26-8.30 (m, 2H), 8.53 (t, J 1.8 Hz, 1H), 8.74 (dd, J 4.8, 1.8 Hz, 1H), 8.48 (brs, 1H), 9.19 (dd, J 2.4, 0.9 Hz, 1H) | m/z (EI) 502 (M⁺) | Example 7 |
| 40 | 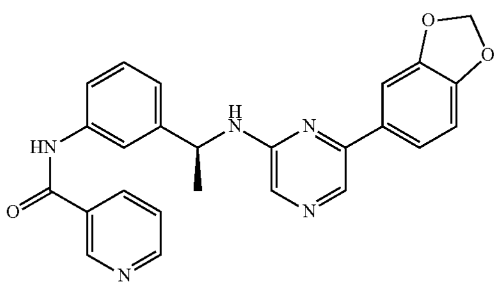 [SMILES: C[C@H](Nc1cncc(-c2ccc3c(c2)OCO3)n1)c1cccc(NC(=O)c2cccnc2)c1] | δ 1.60 (d, J 6.9 Hz, 3H), 4.95-5.03 (m, 1H), 5.18 (d, J 6.3 Hz, 1H), 5.96 (s, 2H), 6.84 (dd, J 7.8, 0.6 Hz, 1H), 7.22 (d, J 7.8 Hz, 1H), 7.31-7.41 (m, 4H), 7.53-7.56 (m, 1H), 7.67 (s, 1H), 7.72 (s, 1H), 8.14 (s, 1H), 8.15-8.19 (m, 1H), 8.33 (brs, 1H), 8.72 (dd, J 4.8, 1.8 Hz, 1H), 9.07 (dd, J 2.4, 0.9 Hz, 1H) | m/z (EI) 439 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 41 | (structure: 3-methylpyridine carboxamide linked via CH(CH₃)NH to pyrazine) | δ 1.58 (d, J 6.9 Hz, 3H), 2.40 (s, 3H), 4.88-4.97 (m, 1H), 5.16 (d, J 6.6 Hz, 1H), 7.18 (d, J 7.5 Hz, 1H), 7.34 (t, J 7.8 Hz, 1H), 7.52-7.56 (m, 1H), 7.69 (t, J 1.8 Hz, 1H), 7.77-7.79 (m, 2H), 7.94 (dd, J 2.7, 1.5 Hz, 1H), 7.98-8.00 (m, 1H), 8.18 (brs, 1H), 8.57 (d, J 2.1 Hz, 1H), 8.87 (d, J 1.8 Hz, 1H) | m/z (EI) 333 (M⁺) | Example 2 (byproduct) |
| 42 | (structure: 3-methylpyridine carboxamide linked via CH(CH₃)NH to 6-chloropyrazine) | δ 1.61 (d, J 6.6 Hz, 3H), 2.44 (s, 3H), 4.88-4.97 (m, 1H), 5.17 (d, J 7.2 Hz, 1H), 7.19 (brd, J 8.1 Hz, 1H), 7.37 (t, J 7.8 Hz, 1H), 7.50-7.53 (m, 1H), 7.65 (s, 1H, ), 7.73 (brs, 1H), 7.80 (s, 1H), 7.89 (brs, 1H), 8.01 (brs, 1H), 8.62 (brs, 1H), 8.89 (brs, 1H) | m/z (EI) 367 (M⁺) | Example 1 |
| 43 | (structure: 6-methylpyridine carboxamide linked via CH(CH₃)NH to 6-chloropyrazine) | δ 1.58 (d, J 6.9 Hz, 3H), 2.63 (s, 3H), 4.86-4.95 (m, 1H), 5.29 (d, J 6.6 Hz, 1H), 7.16 (brd, J 7.5 Hz, 1H), 7.27 (d, J 8.1 Hz, 1H), 7.34 (t, J 7.8 Hz, 1H), 7.47-7.51 (m, 1H), 7.63 (s, 1H), 7.72 (t, J 1.8 Hz, 1H), 7.77 (s, 1H), 8.06-8.09 (m, 2H), 8.97 (d, J 2.4 Hz, 1H) | m/z (EI) 367 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 44 | [structure: 3-(N,N-dimethylsulfamoyl)phenyl-pyrazine linked via NH-CH(CH₃)- to phenyl with ortho-NHC(O)-(6-methylpyridin-3-yl)] | δ 1.60 (d, J 6.9 Hz, 3H), 2.45 (s, 3H), 2.69 (s, 6H), 5.01–5.10 (m, 1H), 5.26 (d, J 6.0 Hz, 1H), 7.20 (d, J 7.8 Hz, 1H), 7.35 (t, J 7.8 Hz, 1H), 7.53 (brs, 1H), 7.58 (t, J 7.8 Hz, 1H), 7.74 (d, J 8.1 Hz, 1H), 7.84 (d, J 9.0 Hz, 1H), 7.90 (s, 1H), 8.07 (d, J 7.8 Hz, 1H), 8.12 (brs, 1H), 8.31 (s, 1H), 8.55 (t, J 1.5 Hz, 1H), 8.59 (d, J 1.5 Hz, 1H), 8.70 (s, 1H), 9.00 (d, J 1.8 Hz, 1H) | m/z (EI) 516 (M⁺) | Example 2 |
| 45 | [structure: pyrazine linked via NH-CH(CH₃)- to phenyl with ortho-NHC(O)-(6-methylpyridin-3-yl)] | δ 1.56 (d, J 6.9 Hz, 3H), 2.61 (s, 3H), 4.86–4.95 (m, 1H), 5.19 (d, J 6.3 Hz, 1H), 7.15 (d, J 7.8 Hz, 1H), 7.24 (d, J 8.1 Hz, 1H), 7.30 (t, J 7.8 Hz, 1H), 7.51 (d, J 8.1 Hz, 1H), 7.68 (s, 1H), 7.75–7.77 (m, 2H), 7.92–7.93 (m, 1H), 8.06 (dd, J 8.4, 2.4 Hz, 1H), 8.20 (brs, 1H), 8.95 (d, J 2.1 Hz, 1H) | m/z (EI) 333 (M⁺) | Example 2 (byproduct) |
| 46 | [structure: 3-(N,N-dimethylsulfamoyl)phenyl-pyrazine linked via NH-CH(CH₃)- to phenyl with ortho-NHC(O)-(6-methylpyridin-3-yl)] | δ 1.61 (d, J 6.9 Hz, 3H), 2.64 (s, 3H), 2.69 (s, 6H), 5.01–5.10 (m, 1H), 5.20 (d, J 6.3 Hz, 1H), 7.17 (d, J 6.6 Hz, 1H), 7.21–7.30 (m, 1H), 7.35 (t, J 8.1 Hz, 1H), 7.56–7.61 (m, 2H), 7.73–7.76 (m, 1H), 7.79–7.82 (m, 1H), 7.90 (s, 1H), 8.06–8.09 (m, 1H), 8.18 (dd, J 8.1, 2.4 Hz, 1H), 8.31 (s, 1H), 8.52–8.55 (m, 2H), 9.08 (d, J 2.1 Hz, 1H) | m/z (EI) 516 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 47 | [structure: N-(3-((6-fluoropyridin-2-ylamino)methyl)phenyl)-5-methylnicotinamide] | δ 1.55 (d, J 6.9 Hz, 3H), 2.41 (s, 3H), 4.74-4.83 (m, 1H), 4.94 (brd, J 6.6 Hz, 1H), 6.06 (dd, J 8.1, 2.4 Hz, 1H), 6.11 (dd, J 7.8, 2.4 Hz, 1H), 7.16 (brd, J 7.8 Hz, 1H), 7.31-7.42 (m, 2H), 7.56-7.63 (m, 2H), 7.98 (brs, 2H), 8.58 (d, J 1.5 Hz, 1H), 8.87 (d, J 1.5 Hz, 1H) | m/z (EI) 350 (M⁺) | Example 1 |
| 48 | [structure: with 5-chloropyrazin-2-yl and 6-aminonicotinamide] | CD₃OD δ 1.55 (d, J 6.9 Hz, 3H), 5.03 (q, J 6.8 Hz, 1H), 7.20 (brd, J 7.8 Hz, 1H), 7.32 (t, J 8.1 Hz, 1H), 7.50 (dd, J 2.7, 2.1 Hz, 1H), 7.53-7.56 (m, 1H), 7.59 (s, 1H), 7.72 (t, J 1.8 Hz, 1H), 7.77 (s, 1H), 8.10 (d, J 2.7 Hz, 1H), 8.28 (d, J 1.8 Hz, 1H) | m/z (EI) 368 (M⁺) | Example 8 |
| 49 | [structure: with 6-chloropyrazin-2-yl and 6-aminonicotinamide] | CD₃OD δ 1.54 (d, J 6.9 Hz, 3H), 5.02 (q, J 6.9 Hz, 1H), 6.60 (d, J 9.0 Hz, 1H), 7.16 (d, J 8.4 Hz, 1H), 7.30 (t, J 7.8 Hz, 1H), 7.50-7.53 (m, 1H), 7.59 (s, 1H), 7.69 (t, J 1.8 Hz, 1H), 7.76 (s, 1H), 7.97 (ddd, J 8.7, 2.4, 0.3 Hz, 1H), 8.54 (d, J 2.1 Hz, 1H) | m/z (EI) 368 (M⁺) | Example 8 |

TABLE 1-continued

| Compound Number | Structure | ¹H nmr data (in CDCl₃ unless otherwise stated) | Mass spectral data | Synthetic Method |
|---|---|---|---|---|
| 50 | 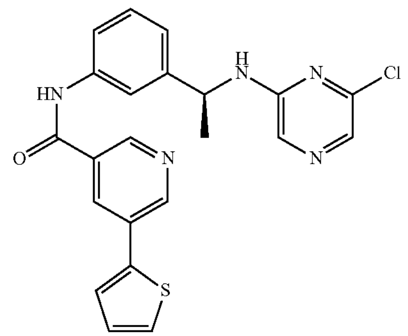 [SMILES: C[C@H](Nc1cncc(Cl)n1)c1cccc(NC(=O)c2cncc(-c3cccs3)c2)c1] | CD₃OD δ 1.56 (d, J 6.9 Hz, 3H), 5.05 (q, J 6.9 Hz, 1H), 7.18-7.24 (m, 2H), 7.35 (t, J 7.8 Hz, 1H), 7.55-7.64 (m, 4H), 7.78 (brs, 2H), 8.54 (t, J 2.1 Hz, 1H), 8.95 (d, J 2.1 Hz, 1H), 8.98 (d, J 2.1 Hz, 1H) | m/z (EI) 435 (M⁺) | Example 1 |
| 51 | 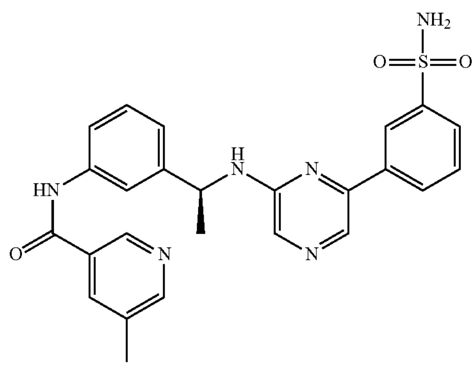 [SMILES: Cc1cncc(C(=O)Nc2cccc([C@H](C)Nc3cncc(-c4cccc(S(N)(=O)=O)c4)n3)c2)c1] | CD₃OD δ 1.59 (d, J 6.9 Hz, 3H), 2.45 (s, 3H), 5.14 (q, J 7.2 Hz, 1H), 7.27-7.36 (m, 2H), 7.53-7.58 (m, 2H), 7.80 (brs, 1H), 7.88-7.91 (m, 2H), 8.08 (dd, 7.8, 1.2, Hz, 1H), 8.17-8.19 (m, 2H), 8.54-8.56 (m, 2H), 8.87 (brs, 1H) | m/z (ESI) 489 (M⁺ + 1) | Example 2 |
| 52 | 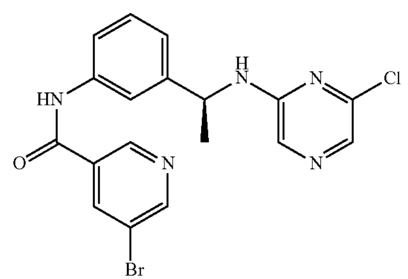 [SMILES: C[C@H](Nc1cncc(Cl)n1)c1cccc(NC(=O)c2cncc(Br)c2)c1] | δ 1.56 (d, 6.9 Hz, 3H), 4.85-4.94 (m, 1H), 5.32 (d, J 6.6 Hz, 1H), 7.17 (d, J 7.8 Hz, 1H), 7.33 (t, J 7.8 Hz, 1H), 7.47-7.50 (m, 1H), 7.61 (s, 1H), 7.66 (s, 1H), 7.76 (s, 1H), 8.27 (s, 1H), 8.30 (t, J 2.1 Hz, 1H), 8.80 (d, J 2.1 Hz, 1H), 8.96 (d, J 1.2 Hz, 1H) | m/z (EI) 433, 431 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 53 | 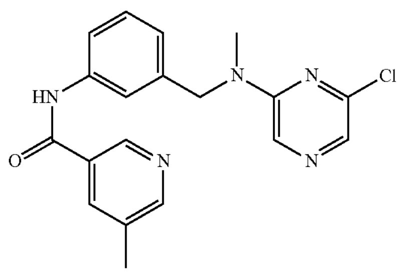 [SMILES: Cc1cncc(C(=O)Nc2cccc(CN(C)c3cncc(Cl)n3)c2)c1] | δ 2.42 (s, 3H), 3.14 (s, 3H), 4.79 (s, 2H), 7.04 (d, J 7.8 Hz, 1H), 7.35 (t, J 7.8 Hz, 1H), 7.53 (brs, 1H), 7.58 (brd, J 8.1 Hz, 1H), 7.80 (s, 1H), 7.87 (s, 1H), 7.99 (brs, 2H), 8.58 (brs, 1H), 8.87 (brs, 1H) | m/z (EI) 367 (M⁺) | Example 1 |
| 54 | 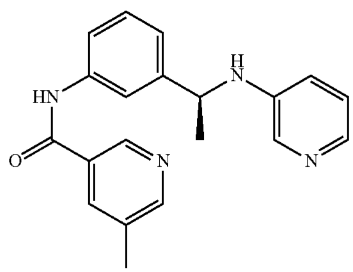 | δ 1.54 (d, J 6.9 Hz, 3H), 2.37 (s, 3H), 4.23 (brs, 1H), 4.46 (q, J 6.6 Hz, 1H), 6.69-6.73 (m, 1H), 6.94 (dd, J 8.4, 4.8 Hz, 1H), 7.14 (d, J 7.8 Hz, 1H), 7.32 (t, J 7.8 Hz, 1H), 7.57 (d, J 7.8 Hz, 1H), 7.65 (brs, 1H), 7.84 (d, J 4.5 Hz, 1H), 7.94 (d, J 2.4 Hz, 1H), 7.98 (brs, 1H), 8.54 (brs, 2H), 8.86 (d, J 1.5 Hz, 1H) | m/z (EI) 322 (M⁺) | Example 1 |
| 55 | 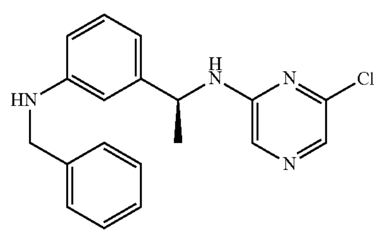 [SMILES: C[C@H](Nc1cncc(Cl)n1)c1cccc(NCc2ccccc2)c1] | δ 1.54 (d, J 6.9 Hz, 3H), 4.32 (s, 2H) 4.71-4.80 (m, 1H), 5.03 (d, J 6.3 Hz, 1H), 6.53-6.57 (m, 1H), 6.60-6.61 (m, 1H), 6.68-6.71 (m, 1H), 7.15 (t, J 7.5 Hz, 1H), 7.33-7.35 (m, 4H), 7.59 (s, 1H), 7.80 (s,1H) | m/z (EI) 338 (M⁺) | Example 4 |
| 56 | 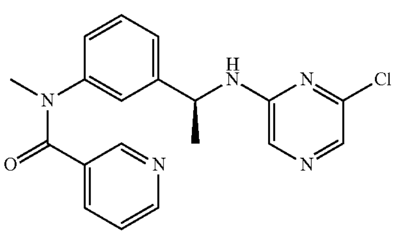 [SMILES: C[C@H](Nc1cncc(Cl)n1)c1cccc(N(C)C(=O)c2cccnc2)c1] | δ 1.36 (d, J 6.9 Hz, 3H), 3.49 (s, 3H), 4.70-4.79 (m, 1H), 5.43 (brs, 1H), 6.94 (m, 1H), 7.00-7.06 (m, 1H), 7.15 7.17 (m, 1H), 7.25 (t, J 7.8 Hz, 1H), 7.49-7.53 (m, 2H), 7.76 (s, 1H), 8.38 (brs, 1H), 8.43 (brs, 1H) | m/z (EI) 366 (M⁺) | Example 1 |

TABLE 1-continued

| Compound Number | Structure | $^1$H nmr data (in CDCl$_3$ unless otherwise stated) | Mass spectral data | Synthetic Method |
|---|---|---|---|---|
| 57 | 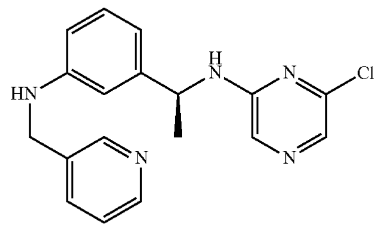 [SMILES: C[C@H](Nc1cncc(Cl)n1)c1cccc(NCc2cccnc2)c1] | δ 1.51 (d, J 6.9 Hz, 3H), 4.24 (brs, 1H), 4.32 (s, 2H), 4.71-4.80 (m, 1H), 5.35 (d, J 6.6 Hz, 1H), 6.51 (ddd, J 8.1, 2.4, 0.9 Hz, 1H), 6.52 (m, 1H), 6.70 (brd, J 7.8 Hz, 1H), 7.13 (t, J 7.8 Hz, 1H), 7.22 (dd, J 7.8, 4.8 Hz, 1H), 7.58 (s, 1H), 7.63-7.66 (m, 1H), 7.75 (s, 1H), 8.49 (d, J 3.9 Hz, 1H), 8.58 (s, 1H) | m/z (EI) 339 (M$^+$) | Example 4 |
| 58 | 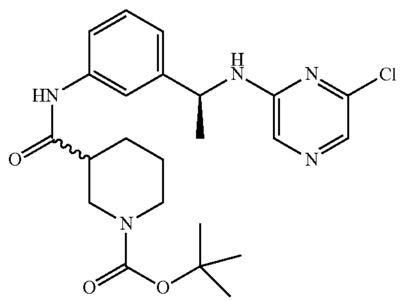 [SMILES: C[C@H](Nc1cncc(Cl)n1)c1cccc(NC(=O)C2CCCN(C(=O)OC(C)(C)C)C2)c1] | δ 1.46 & 1.47 (2xs, 9H), 1.56 (d, J 6.9 Hz, 3H), 1.63 (brs, 2H), 1.91 (brs, 1H), 2.50 (brs, 1H), 3.14-3.88 (m, 4H), 4.81-4.90 (m, 1H), 5.17 (d, J 6.9 Hz, 1H), 7.09 (d, J 7.8 Hz, 1H), 7.27 (t, J 7.8 Hz, 1H), 7.42 (brd, J 8.1 Hz, 1H), 7.62 (brs, 1H), 7.69 (brd, J 1.5 Hz, 1H), 7.78 (s, 1H) | m/z (EI) 459 (M$^+$) | Example 1 |
| 59 | 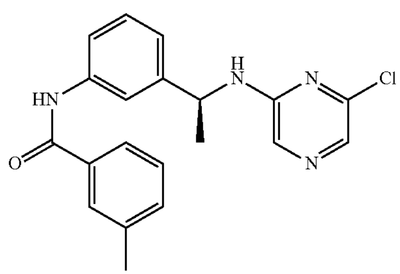 | δ 1.58 (d, J 6.6 Hz, 3H), 2.42 (s, 3H), 4.85-4.94 (m, 1H), 5.16 (d, J 6.6 Hz, 1H), 7.13 (d, J 7.8 Hz, 1H), 7.31-7.37 (m, 3H), 7.49-7.52 (m, 1H), 7.63-7.67 (m, 3H), 7.73 (brs, 1H), 7.78 (s, 1H), 7.86 (brs, 1H) | m/z (EI) 366 (M$^+$) | Example 1 |

TABLE 1-continued

| Compound Number | Structure | ¹H nmr data (in CDCl₃ unless otherwise stated) | Mass spectral data | Synthetic Method |
|---|---|---|---|---|
| 60 | (structure) | δ 1.59 (d, J 6.9 Hz, 3H), 2.40 (s, 3H), 3.96 (s, 3H), 4.84-4.94 (m, 1H), 5.49 (d, J 6.6 Hz, 1H), 7.17 (d, J 7.8 Hz, 1H), 7.33 (t, J 7.8 Hz, 1H), 7.60 (d, J 8.1 Hz, 1H), 7.71 (s, 1H), 7.89 (s, 1H), 8.28 (s, 1H), 8.50 (s, 1H), 8.57 (s, 1H), 8.91 (s, 1H), 8.00 (s, 1H) | m/z (EI) 391 (M⁺) | Example 9 |
| 61 | (structure) | δ 1.51 (d, J 6.9 Hz, 3H), 2.38 (s, 3H), 4.58-4.67 (m, 1H), 5.10 (d, J 6.0 Hz, 1H), 6.06 (d, J 8.1 Hz, 1H), 6.67 (d, J 7.5 Hz, 1H), 7.09-7.14 (m, 2H), 7.32 (t, J 7.8 Hz, 1H), 7.57-7.61 (m, 2H), 7.97 (s, 1H), 8.10 (s, 1H), 8.55 (s, 1H), 8.86 (s, 1H) | m/z (EI) 412, 410 (M⁺) | Example 10 |
| 62 | (structure) | δ 1.56 (d, J 6.9 Hz, 3H), 2.41 (s, 3H), 4.29 (d, J 5.4 Hz, 1H), 4.42-4.51 (m, 1H), 6.87 (t, J 2.1 Hz, 1H), 7.14 (d, J 7.8 Hz, 1H), 7.35 (t, J 7.8 Hz, 1H), 7.51 (d, J 8.1 Hz, 1H), 7.69 (s, 1H) 7.86 (d, J 2.7 Hz, 1H), 7.92 (d, J 1.8 Hz, 1H), 7.98 (s, 1H), 8.09 (brs, 1H, ), 8.58 (d, J 1.5 Hz, 1H), 8.87 (d, J 1.8 Hz, 1H) | m/z (EI) 412, 410 (M⁺) | Example 10 |

TABLE 1-continued

| Compound Number | Structure | ¹H nmr data (in CDCl₃ unless otherwise stated) | Mass spectral data | Synthetic Method |
|---|---|---|---|---|
| 63 | 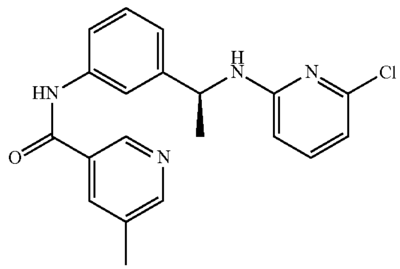 [SMILES: Cc1cncc(C(=O)Nc2cccc([C@H](C)Nc3cccc(Cl)n3)c2)c1] | δ 1.53 (d, J 6.9 Hz, 3H), 2.40 (s, 3H), 4.63-4.71 (m, 1H), 5.09 (d, J 6.0 Hz, 1H), 6.05 (d, J 8.1 Hz, 1H), 6.54 (d, J 7.8 Hz, 1H), 7.15 (d, J 7.8 Hz, 1H), 7.24 (t, J 7.8 Hz, 1H), 7.33 (t, J 7.8 Hz, 1H), 7.59-7.62 (m, 2H) 7.99 (s, 1H), 8.10 (brs, 1H), 8.57 (s, 1H), 8.88 (s, 1H) | m/z (EI) 366 (M⁺) | Example 10 |
| 64 | 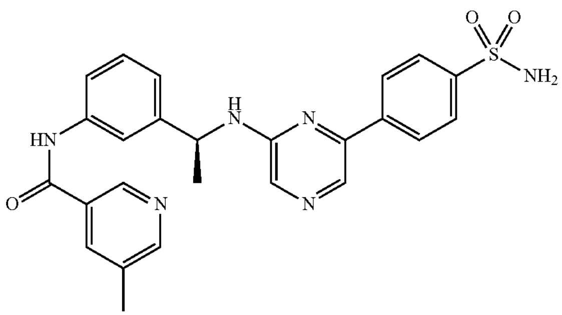 [SMILES: Cc1cncc(C(=O)Nc2cccc([C@H](C)Nc3cncc(-c4ccc(S(N)(=O)=O)cc4)n3)c2)c1] | CD₃OD δ 1.61 (d, J 6.9 Hz, 3H), 2.45 (s, 3H), 5.12 (q, J 6.6 Hz, 1H), 7.26-7.36 (m, 2H), 7.50 (d, J 7.8 Hz, 1H), 7.89-7.93 (m, 4H), 8.03 (s, 1H), 8.05 (brs, 1H), 8.17 (brs, 2H), 8.55 (s, 1H), 8.86 (s, 1H) | m/z (EI) 488 (M⁺) | Example 7 |
| 65 | 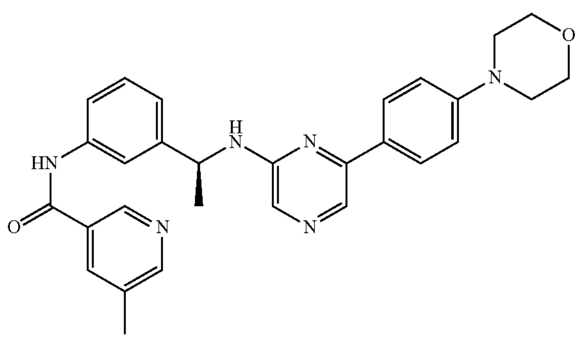 [SMILES: Cc1cncc(C(=O)Nc2cccc([C@H](C)Nc3cncc(-c4ccc(N5CCOCC5)cc4)n3)c2)c1] | δ 1.62 (d, J 6.9 Hz, 3H), 2.39 (s, 3H), 3.22 (t, J 4.8 Hz, 4H), 3.87 (t, J 4.8 Hz, 4H), 4.97-5.05 (m, 1H), 5.09 (d, J 6.3 Hz, 1H), 6.93 (d, J 9.0 Hz, 2H), 7.23 (d, J 7.8 Hz, 1H), 7.35 (d, J 7.8 Hz, 1H), 7.55 (d, J 8.4 Hz, 1H), 7.64 (s, 1H), 7.73 (s, 1H), 7.84 (d, J 9.0 Hz, 2H), 7.98 (s, 1H), 8.11 (s, 1H), 8.21 (s, 1H), 8.57 (d, J 1.5 Hz, 1H), 8.87 (d, J 1.5 Hz, 1H) | m/z (EI) 494 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 66 | [structure: 5-chloropyrazin-2-yl amino connected to CH(CH₃) with phenyl bearing thiazole-carboxamide] | d6 DMSO δ 1.47 (d, J 6.9 Hz, 3H), 4.90-4.99 (m, 1H), 7.15 (d, J 7.8 Hz, 1H), 7.32 (t, J 7.8 Hz, 1H), 7.60 (d, J 7.8 Hz, 1H), 7.67 (s, 1H), 7.69 (brs, 1H), 7.90 (s, 1H), 8.03 (d, J 7.5 Hz, 1H), 8.67 (s, 1H), 9.29 (s, 1H), 10.41 (brs, 1H) | m/z (EI) 359 (M⁺) | Example 1 |
| 67 | [structure: 5-chloropyrazin-2-yl amino connected to CH(CH₃) with phenyl bearing pyridine-3-sulfonamide] | 1.50 (d, J 6.9 Hz, 3H), 4.78-4.87 (m, 1H), 5.31 (d, J 6.3, 1H), 7.03 (ddd, J 7.8, 2.1, 1.2 Hz, 1H), 7.09 (t, J 1.8 Hz, 1H), 7.16-7.18 (m, 1H), 7.26 (t, J 7.8 Hz, 1H), 7.32 (ddd, J 8.1, 4.8, 0.3 Hz, 1H), 7.50 (brs, 1H), 7.58 (s, 1H), 7.80 (s, 1H), 7.89-7.93 (m, 1H), 8.73 (d, J 3.6 Hz, 1H), 8.94 (d, J 1.5 Hz, 1H) | m/z (EI) 389 (M⁺) | Example 11 |
| 68 | [structure: 5-chloropyrazin-2-yl amino connected to CH(CH₃) with phenyl bearing 5-methylpyridine amide] | 1.48 (d, J 6.6 Hz, 3H), 1.52 (d, J 6.9 Hz, 3H), 4.05 (brs, 1H), 4.44-4.52 (m, 1H), 4.64-4.75 (m, 1H), 4.99-5.11 (m, 1H), 6.36-6.40 (m, 1H), 6.45-6.50 (m, 1H), 6.64 (d, J 7.5 Hz, 1H), 7.06 (td, J 7.8, 1.5 Hz, 1H), 7.45-7.56 (m, 2H), 7.77 (brs, 1H), 8.30 (brs, 1H), 8.42 (brs, 1H) | m/z (EI) 367 (M⁺) | Example 12 |
| 69 | [structure: 5-chloropyrazin-2-yl amino connected to CH(CH₃) with phenyl bearing 5-methylpyridine amide] | δ 1.60 (d, J 6.9 Hz, 3H), 2.36 (s, 3H), 4.96-5.05 (m, 1H), 5.32 (d, J 6.9 Hz, 1H), 7.46 (t, J 7.8 Hz, 1H), 7.57 (brd, J 7.8 Hz, 1H), 7.66 (s, 1H), 7.75-7.78 (m, 1H), 7.78 (s, 1H), 7.95 (brs, 1H), 8.16-8.21 (m, 3H), 8.50 (brs, 1H) | m/z (EI) 367 (M⁺) | Example 13 |

TABLE 1-continued

| Compound Number | Structure | 1H nmr data (in CDCl3 unless otherwise stated) | Mass spectral data | Synthetic Method |
|---|---|---|---|---|
| 70 | 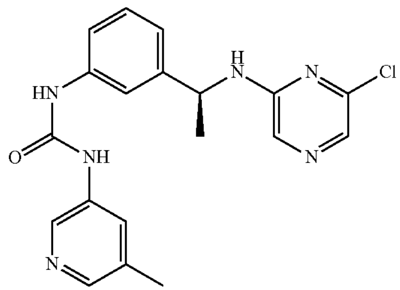 [SMILES: Cc1cncc(NC(=O)Nc2cccc([C@H](C)Nc3cncc(Cl)n3)c2)c1] | δ 1.47 (d, J 6.9 Hz, 3H), 2.18 (s, 3H), 4.80-4.92 (m, 1H), 5.92 (d, J 4.8 Hz, 1H), 7.01 (d, J 6.6 Hz, 1H), 7.14-7.22 (m, 2H), 7.37 (brs, 1H), 7.60 (brs, 1H), 7.69 (brs, 1H), 7.77 (brs, 1H), 7.90-8.25 (m, 4H) | m/z (EI) 382 (M+) | Example 14 |
| 71 | 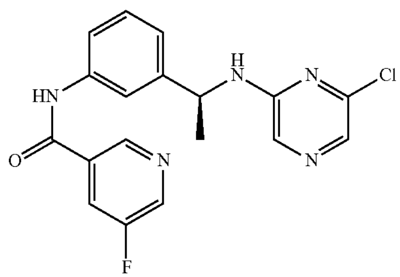 | δ 1.60 (d, J 6.9 Hz, 3H), 4.87-4.96 (m, 1H), 5.18 (d, J 6.6 Hz, 1H), 7.20 (brd, J 7.8 Hz, 1H), 7.38 (t, J 7.8 Hz, 1H), 7.49-7.53 (m, 1H), 7.64 (s, 1H), 7.71 (t, J 1.5 Hz, 1H), 7.80 (s, 1H) 7.92-7.96 (m, 2H), 8.65 (d, J 2.7 Hz, 1H), 8.89 (t, J 1.5 Hz, 1H) | m/z (EI) 371 (M+) | Example 1 |
| 72 | 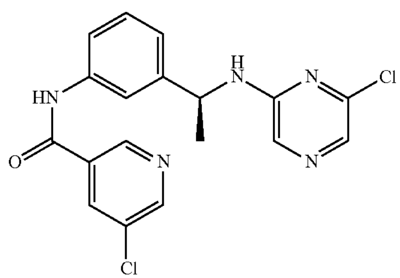 | δ 1.58 (d, J 6.9 Hz, 3H), 4.86-4.95 (m, 1H), 5.26 (d, J 6.9 Hz, 1H), 7.19 (d, J 7.5 Hz, 1H), 7.36 (t, J 7.8 Hz, 1H), 7.49-7.52 (m, 1H), 7.63 (s, 1H), 7.68 (brs, 1H), 7.78 (s, 1H), 8.11 (brs, 1H), 8.17 (t, J 1.8H, 1H), 8.72 (d, J 2.4 Hz, 1H), 8.93 (d, J 1.8 Hz, 1H) | m/z (EI) 388 (M+) | Example 1 |

TABLE 1-continued

| Compound Number | Structure | $^1$H nmr data (in CDCl$_3$ unless otherwise stated) | Mass spectral data | Synthetic Method |
|---|---|---|---|---|
| 73 | (structure: N-[3-((R)-1-{[6-morpholin-4-yl-pyrazin-2-yl]amino}ethyl)phenyl]-5-methylnicotinamide) | δ 1.55 (d, J 6.3 Hz, 3H), 2.39 (s, 3H), 3.33-3.46 (m, 4H), 3.72-3.75 (m, 2H), 4.80-4.91 (m, 2H), 7.13-7.16 (m, 2H), 7.28-7.33 (m, 2H), 7.49 (dd, J 7.8, 1.2 Hz, 1H), 7.70 (brs, 1H), 7.99 (brs, 1H), 8.24 (s, 1H), 8.56 (brs, 1H), 8.86 (brs, 1H) | m/z (EI) 418 (M$^+$) | Example 15 |
| 74 | (structure: with piperidine) | δ 1.46-1.65 (m, 9H), 2.40 (s, 3H), 3.37-3.44 (m, 4H), 4.74 (brs, 1H), 4.78-4.87 (m, 1H), 7.04 (s, 1H), 7.16 (d, J 7.5 Hz, 1H), 7.28-7.34 (m, 2H), 7.55-7.62 (m, 2H), 7.99 (s, 1H), 8.07-8.31 (brs, 1H), 8.56 (s, 1H), 8.87 (d, J 1.8 Hz, 1H) | m/z (EI) 416 (M$^+$) | Example 15 |
| 75 | (structure: with 4-methylpiperazine) | δ 1.55 (d, J 6.6 Hz, 3H), 2.30 (s, 3H), 2.40 (s, 3H), 2.42-2.45 (m, 4H), 3.41-3.48 (m, 4H), 4.78-4.86 (m, 2H), 7.11 (s, 1H), 7.15 (d, J 7.8 Hz, 1H), 7.29-7.34 (m, 2H), 7.51 (d, J 9.0 Hz, 1H), 7.66 (brs, 1H), 7.98 (s, 1H), 8.21 (brs, 1H), 8.57 (d, J 1.5 Hz, 1H), 8.87 (d, J 1.8 Hz, 1H) | m/z (EI) 431 (M$^+$) | Example 15 |

TABLE 1-continued

| Compound Number | Structure | ¹H nmr data (in CDCl₃ unless otherwise stated) | Mass spectral data | Synthetic Method |
|---|---|---|---|---|
| 76 | (structure) | δ 1.63 (d, J 6.6 Hz, 3H), 2.42 (s, 3H), 3.93 (s, 3H), 4.94-5.06 (m, 2H), 5.84 (brs, 1H), 6.95 (d, J 8.1 Hz, 1H) 7.19 (d, J 7.8 Hz, 1H), 7.30-7.36 (m, 3H), 7.41-7.47 (m, 2H), 7.48-7.52 (m, 1H), 7.61-7.64 (m, 1H), 7.67 (s, 1H), 7.69 (s, 1H), 7.77 (t, J 1.8 Hz, 1H), 7.83 (brs, 1H), 8.22 (s, 1H) | m/z (EI) 454 (M⁺) | Example 7 |
| 77 | (structure) | CD₃OD δ 1.61 (d, J 6.9 Hz, 3H), 2.43 (s, 3H), 5.13 (q, J 7.2 Hz, 1H), 7.24 (dt, J 7.8, 1.2 Hz, 1H), 7.33 (t, J 7.5 Hz, 1H), 7.38-7.43 (m, 2H), 7.48-7.52 (m, 1H), 7.55-7.94 (m, 7H), 8.07 (d, J 8.7 Hz, 2H), 8.20 (s, 1H) | m/z (EI) 487 (M⁺) | Example 7 |
| 78 | (structure) | δ 1.62 (d, J 6.3 Hz, 3H), 2.36 (s, 3H), 2.41 (s, 3H), 2.54 (t, J 5.1 Hz, 4H), 3.65 (t, J 5.1 Hz, 4H), 4.99-5.05 (m, 2H), 6.68 (d, J 9.0 Hz, 1H), 7.23 (d, J 7.8 Hz, 1H), 7.36 (t, J 7.8 Hz, 1H), 7.52-7.55 (m, 1H), 7.67 (s, 1H), 7.72 (t, J 1.8 Hz, 1H), 7.95-8.02 (m, 3H), 8.17 (s, 1H), 8.59 (d, J 1.5 Hz, 1H), 8.75 (d, J 2.1 Hz, 1H), 8.88 (d, J 2.1 Hz, 1H) | m/z (EI) 508 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 79 | 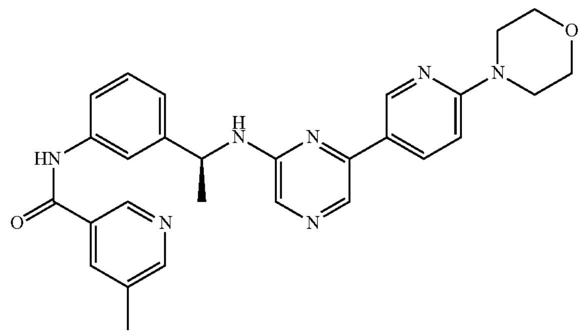 [SMILES: Cc1cncc(C(=O)Nc2cccc([C@H](C)Nc3cncc(-c4ccc(N5CCOCC5)nc4)n3)c2)c1] | δ 1.64 (d, J 6.3 Hz, 3H), 2.43 (s, 3H), 3.58 (t, J 4.8 Hz, 4H), 3.83 (t, J 4.8 Hz, 4H), 5.01-5.07 (m, 2H), 6.67 (d, J 9.0 Hz, 1H), 7.24 (d, J 7.8 Hz, 1H), 7.37 (t, J 7.8 Hz, 1H), 7.54 (d, J 9.0 Hz, 1H), 7.69 (s, 1H), 7.74 (s, 1H), 7.95-8.05 (m, 3H), 8.19 (s, 1H), 8.60 (s, 1H), 8.77 (dd, J 2.4, 0.6 Hz, 1H), 8.89 (s, 1H) | m/z (EI) 495 (M⁺) | Example 7 |
| 80 | 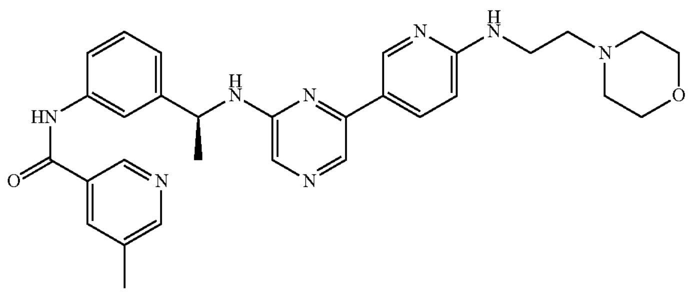 [SMILES: Cc1cncc(C(=O)Nc2cccc([C@H](C)Nc3cncc(-c4ccc(NCCN5CCOCC5)nc4)n3)c2)c1] | δ 1.61 (d, J 6.6 Hz, 3H), 2.40 (s, 3H), 2.50 (t, J 4.5 Hz, 4H), 2.63 (t, J 6.0 Hz, 2H), 3.37-3.43 (m, 2H), 3.72 (t, J 4.5 Hz, 4H), 4.96-5.05 (m, 1H), 5.09 (brd, J 5.7 Hz, 1H), 5.35 (t, J 4.8 Hz, 1H), 6.44 (d, J 8.7 Hz, 1H), 7.21 (d, J 7.8 Hz, 1H), 7.35 (t, J 7.8 Hz, 1H), 7.55 (d, J 8.7 Hz, 1H), 7.65 (s, 1H), 7.71 (brs, 1H), 7.94 (dd, J 8.7, 2.1 Hz, 1H), 7.99 (s, 1H), 8.14-8.24 (m, 2H), 8.57 (s, 1H), 8.66 (d, J 2.1 Hz, 1H), 8.89 (d, J 1.8 Hz, 1H) | m/z (EI) 539 (M⁺ + 1) | Example 7 |
| 81 | 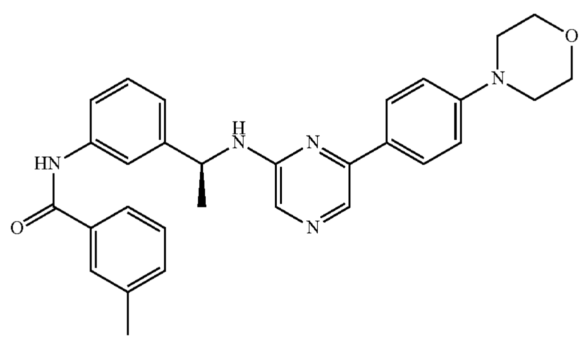 [SMILES: Cc1cccc(C(=O)Nc2cccc([C@H](C)Nc3cncc(-c4ccc(N5CCOCC5)cc4)n3)c2)c1] | δ 1.62 (d, J 6.6 Hz, 3H), 2.42 (s, 3H), 3.20 (t, J 4.8 Hz, 4H), 3.85 (t, J 4.8 Hz, 4H), 4.95-5.04 (m, 2H), 6.93 (d, J 9.0 Hz, 2H), 7.19 (dt, 7.8, 1.2 Hz, 1H), 7.33-7.36 (m, 3H), 7.52 (ddd, J 7.8, 2.1, 1.2 Hz, 1H), 7.62-7.65 (m, 2H), 7.68 (s, 1H), 7.77 (d, J 1.8 Hz, 1H), 7.85 (d, J 9.0 Hz, 2H), 7.87 (brs, 1H), 8.21 (s, 1H) | m/z (EI) 493 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 82 | 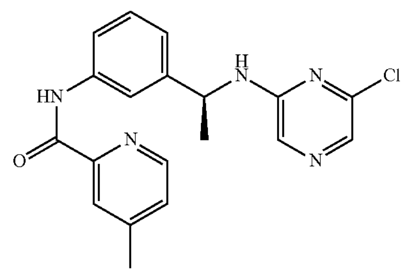 | δ 1.61 (d, J 6.6 Hz, 3H), 2.47 (s, 3H), 4.88-4.97 (m, 1H), 5.18 (d, J 6.6 Hz, 1H), 7.15 (d, J 9.0 Hz, 1H), 7.27-7.31 (m, 1H), 7.36 (t, J 7.8 Hz, 1H), 7.63-7.67 (m, 2H), 7.80 (s, 1H), 7.87 (t, J 2.1 Hz, 1H), 8.11 (brs, 1H), 8.46 (d, J 4.8 Hz, 1H), 10.07 (brs, 1H) | m/z (EI) 367 (M⁺) | Example 1 |
| 83 | 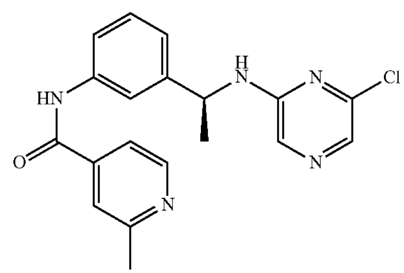 [SMILES: Cc1cc(C(=O)Nc2cccc([C@H](C)Nc3cncc(Cl)n3)c2)ccn1] | δ 1.59 (d, J 6.9 Hz, 3H), 2.65 (s, 3H), 4.86-4.95 (m, 1H), 5.17 (d, J 5.4 Hz, 1H), 7.19 (d, J 7.5 Hz, 1H), 7.36 (t, J 7.8 Hz, 1H), 7.47-7.57 (m, 3H), 7.63 (s, 1H), 7.70 (s, 1H), 7.80 (s, 1H), 7.99 (brs, 1H), 8.65 (brs, 1H) | m/z (EI) 367 (M⁺) | Example 1 |
| 84 | 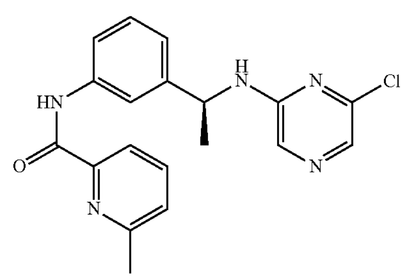 | δ 1.61 (d, J 6.2 Hz, 3H), 2.64 (s, 3H), 4.87-4.96 (m, 1H), 5.25 (brd, J 6.0 Hz, 1H), 7.14 (d, J 7.5 Hz, 1H), 7.32-7.38 (m, 2H), 7.64-7.67 (m, 2H), 7.76-7.81 (m, 2H), 7.88 (s, 1H), 8.09 (d, J 7.8 Hz, 1H), 10.11 (brs, 1H, ) | m/z (EI) 367 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 85 | 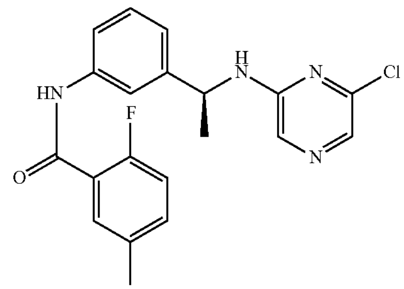 [SMILES: Cc1ccc(F)c(C(=O)Nc2cccc([C@H](C)Nc3cncc(Cl)n3)c2)c1] | δ 1.59 (d, J 6.6 Hz, 3H), 2.38 (s, 3H), 4.87-4.96 (m, 1H), 5.24 (brd, J 6.0 Hz, 1H), 7.05 (dd, J 12.0, 8.4 Hz, 1H), 7.15 (d, J 7.8 Hz, 1H), 7.28-7.36 (m, 2H), 7.50 (d, J 7.8 Hz, 1H), 7.65 (s, 1H), 7.77-7.79 (m, 2H), 7.93 (d, J 7.8 Hz, 1H), 8.48 (d, J 15.0 Hz, 1H) | m/z (EI) 384 (M⁺) | Example 1 |
| 86 | 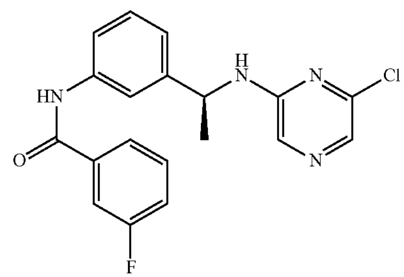 [SMILES: C[C@H](Nc1cncc(Cl)n1)c1cccc(NC(=O)c2cccc(F)c2)c1] | δ 1.56 (d, J 6.6 Hz, 3H), 4.84-4.93 (m, 1H), 5.25 (brs, 1H), 7.14 (d, J 7.8 Hz, 1H), 7.20-7.26 (m, 1H), 7.32 (d, J 7.8 Hz, 1H), 7.40-7.52 (m, 2H), 7.55-7.62 (m, 3H), 7.69 (s, 1H), 7.76 (s, 1H), 8.05 (brs, 1H) | m/z (EI) 370 (M⁺) | Example 1 |
| 87 | 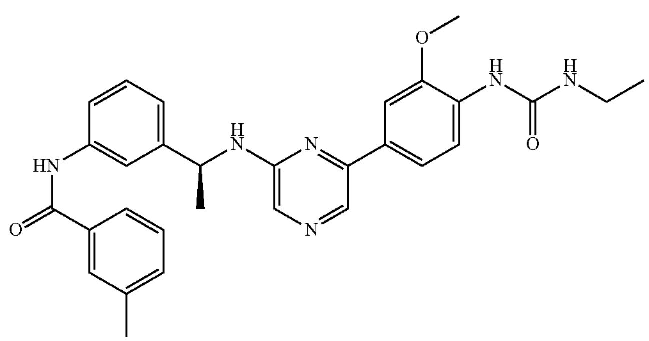 [SMILES: CCNC(=O)Nc1ccc(-c2cncc(N[C@@H](C)c3cccc(NC(=O)c4cccc(C)c4)c3)n2)cc1OC] | CD₃OD δ 1.14 (t, J 7.2 Hz, 3H), 1.59 (d, J 6.9 Hz, 3H), 2.42 (s, 3H), 3.21 (q, J 7.2 Hz, 2H), 3.84 (s, 3H), 5.05-5.13 (m, 1H), 7.23 (brd, J 6.6 Hz, 1H), 7.30 (t, J 7.8 Hz, 1H), 7.36-7.44 (m, 4H), 7.53 (ddd, J 7.8, 2.1, 1.2 Hz, 1H), 7.68-7.71 (m, 1H), 7.73 (brs, 1H), 7.77 (s, 1H), 7.82 (brt, J 11.5 Hz, 1H), 8.05 (d, J 9.0 Hz, 1H), 8.08 (s, 1H) | m/z (EI) 524 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 88 | 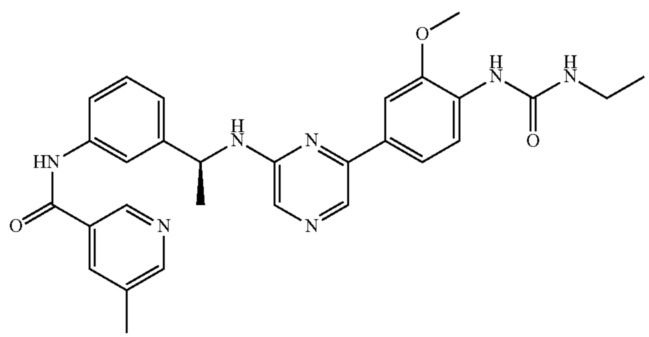 [SMILES: CCNC(=O)Nc1ccc(-c2cncc(N[C@@H](C)c3cccc(NC(=O)c4cncc(C)c4)c3)n2)cc1OC] | CD₃OD δ 1.15 (t, J 7.2 Hz, 3H), 1.60 (d, J 6.9 Hz, 3H), 2.44 (s, 3H), 3.21 (q, J 7.5 Hz, 2H), 3.85 (s, 3H), 5.02-5.13 (m, 1H), 7.26 (brd, J 7.5 Hz, 1H), 7.33 (t, J 7.6 Hz, 1H), 7.41-7.44 (m, 2H), 7.52-7.55 (m, 1H), 7.78 (s, 1H), 7.83 (s, 1H), 8.05 (d, J 9.0 Hz, 1H), 8.09 (s, 1H), 8.15 (s, 1H), 8.55 (s, 1H), 8.86 (s, 1H) | m/z (EI) 525 (M⁺) | Example 2 |
| 89 | 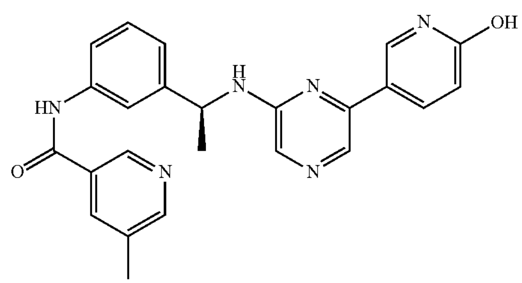 [SMILES: Cc1cncc(C(=O)Nc2cccc([C@H](C)Nc3cncc(-c4ccc(O)nc4)n3)c2)c1] | CD₃OD δ 1.58 (d, J 6.9 Hz, 3H), 2.45 (s, 3H), 5.05 (q, J 6.9 Hz, 1H), 6.55 (dd, J 9.6, 0.6 Hz, 1H), 7.24 (dt, J 7.8, 1.5 Hz, 1H), 7.34 (t, J 7.8 Hz, 1H), 7.46 (ddd, J 7.8, 2.1, 1.2 Hz, 1H), 7.80 (brs, 1H), 7.85 (brt, J 1.5 Hz, 1H), 7.97 (brs, 1H), 8.02 (dd, J 2.7, 0.6 Hz, 1H), 8.10 (dd, J 9.6, 2.7 Hz, 1H), 8.16 (brs, 1H), 8.55 (brs, 1H), 8.87 (brs, 1H) | m/z (EI) 426 (M⁺) | Example 2 |
| 90 | 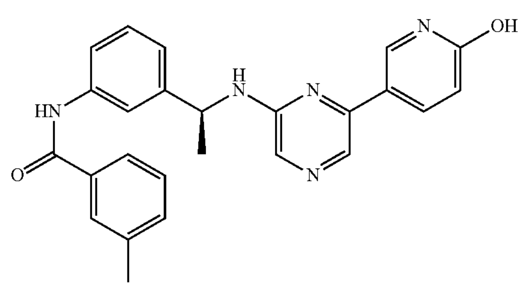 [SMILES: Cc1cccc(C(=O)Nc2cccc([C@H](C)Nc3cncc(-c4ccc(O)nc4)n3)c2)c1] | CD₃OD δ 1.57 (d, J 6.9 Hz, 3H), 2.41 (s, 3H), 5.04 (q, J 6.9 Hz, 1H), 6.54 (d, J 9.6 Hz, 1H), 7.21 (dt, J 7.8, 1.5 Hz, 1H), 7.32 (t, J 7.8 Hz, 1H), 7.36-7.38 (m, 2H), 7.44 (ddd, J 7.8, 2.1, 1.2 Hz, 1H), 7.69-7.72 (m, 1H), 7.74 (s, 1H), 7.79 (brs, 1H), 7.84 (t, J 1.5 Hz, 1H), 7.96 (brs, 1H), 8.02 (d, J 2.4 Hz, 1H), 8.09 (dd, J 9.6, 2.4 Hz, 1H) | m/z (EI) 425 (M⁺) | Example 2 |

TABLE 1-continued

| Compound Number | Structure | ¹H nmr data (in CDCl₃ unless otherwise stated) | Mass spectral data | Synthetic Method |
|---|---|---|---|---|
| 91 | [structure: 5-chloropyrazin-2-yl amino group on chiral methine attached to phenyl with ortho NHC(O)-phenyl-CH₂-N-methylpiperazine] | δ 1.58 (d, J 6.9 Hz, 3H), 2.29 (s, 3H), 2.47 (brs, 8H), 3.56 (s, 2H), 4.85-4.94 (m, 1H), 5.22 (d, J 6.6 Hz, 1H), 7.13 (brd, J 7.8 Hz, 1H), 7.33 (t, J 7.8 Hz, 1H), 7.45 (d, J 8.4 Hz, 2H), 7.49 (ddd, J 8.1, 2.1, 0.9 Hz, 1H), 7.63 (s, 1H), 7.74 (t, J 1.8 Hz, 1H), 7.78 (s, 1H), 7.81 (d, J 8.4 Hz, 2H), 7.93 (brs, 1H) | m/z (EI) 465 (M⁺) | Example 1 |
| 92 | [structure: 5-chloropyrazin-2-yl amino on chiral methine attached to phenyl with ortho NHC(O)-phenyl] | δ 1.56 (d, J 6.9 Hz, 3H), 4.84-4.93 (m, 1H), 5.26 (d, J 6.6 Hz, 1H), 7.12-7.15 (m, 1H), 7.32 (t, J 7.8 Hz, 1H), 7.44-7.57 (m, 4H), 7.62 (s, 1H), 7.72 (t, J 1.8 Hz, 1H), 7.77 (s, 1H), 7.84-7.88 (m, 2H), 8.01 (brs, 1H) | m/z (EI) 352 (M⁺) | Example 1 |
| 93 | [structure: 5-chloropyrazin-2-yl amino on chiral methine attached to phenyl with ortho NHC(O)-4-methylphenyl] | δ 1.58 (d, J 6.9 Hz, 3H), 2.43 (s, 3H), 4.85-4.94 (m, 1H), 5.18 (d, J 6.6 Hz, 1H), 7.13 (brd, J 7.8 Hz, 1H), 7.27-7.36 (m, 3H), 7.49 (ddd, J 7.8, 2.1, 1.2 Hz, 1H), 7.63 (brs, 1H), 7.73-7.79 (m, 4H), 7.88 (brs, 1H) | m/z (EI) 366 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 94 | 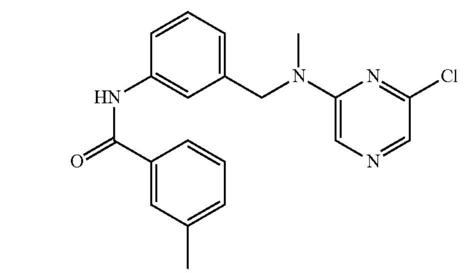 [SMILES: Cc1cccc(C(=O)Nc2cccc(CN(C)c3cncc(Cl)n3)c2)c1] | δ 2.40 (s, 3H), 3.12 (s, 3H), 4.75 (s, 2H), 6.99 (d, J 6.0 Hz, 1H), 7.27-7.35 (m, 3H) 7.54-7.67 (m, 4H), 7.79 (brs, 1H), 7.85 (brs, 1H ), 8.01 (brs, 1H) | m/z (EI) 366 (M⁺) | Example 1 |
| 95 | 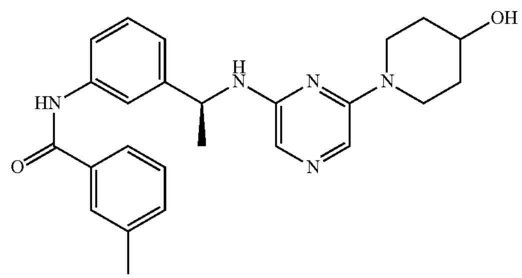 [SMILES: Cc1cccc(C(=O)Nc2cccc([C@H](C)Nc3cncc(N4CCC(O)CC4)n3)c2)c1] | δ 1.54 (d, J 6.3 Hz, 3H), 1.83-1.91 (m, 4H), 2.41 (s, 3H), 2.99-3.09 (m, 2H), 3.80-4.01 (m, 3H), 4.77-4.88 (m, 2H), 7.09-7.14 (m, 2H), 7.26-7.35 (m, 4H), 7.49 (ddd, J 8.1, 2.1, 0.9 Hz, 1H), 7.62-7.67 (m, 3H), 8.02 (brs, 1H) | m/z (EI) 431 (M⁺) | Example 16 |
| 96 | 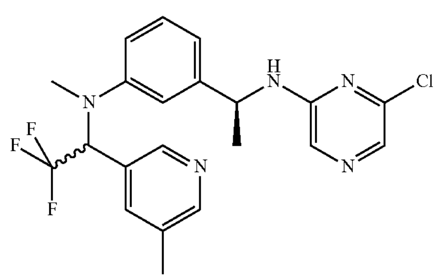 [SMILES: Cc1cncc(C(N(C)c2cccc([C@H](C)Nc3cncc(Cl)n3)c2)C(F)(F)F)c1] | | m/z (EI) 435 (M⁺) | Example 17 |

TABLE 1-continued

| Compound Number | Structure | ¹H nmr data (in CDCl₃ unless otherwise stated) | Mass spectral data | Synthetic Method |
|---|---|---|---|---|
| 97 | 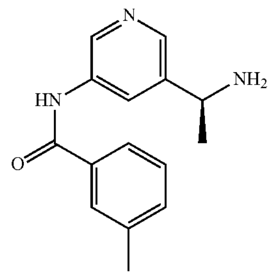 [SMILES: Cc1cccc(C(=O)Nc2cncc([C@H](C)N)c2)c1] | δ 1.42 (d, J 6.6 Hz, 3H), 2.42 (s, 3H), 4.19 (q, J 6.6 Hz, 1H), 7.37 (m, 2H), 7.65-7.7 (m, 2H), 8.25 (brs, 1H), 8.29 (t, J 2.1 Hz, 1H), 8.35 (d, J 1.8 Hz, 1H), 8.61 (d, J 2.4 Hz, 1H) | m/z (EI) 255 (M⁺) | Example 18 |
| 98 | 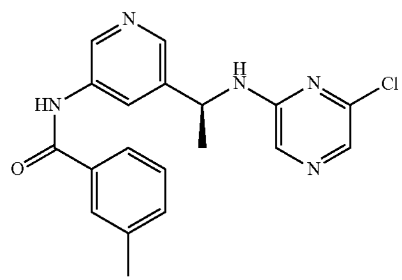 [SMILES: Cc1cccc(C(=O)Nc2cncc([C@H](C)Nc3cncc(Cl)n3)c2)c1] | δ 1.65 (d, J 6.6 Hz, 3H), 2.45 (s, 3H), 5.03-5.12 (m, 1H), 5.20 (d, J 6.6 Hz, 1H), 7.39-7.41 (m, 2H), 7.64-7.72 (m, 3H), 7.82 (s, 1H), 7.93 (s, 1H), 8.40 (s, 1H), 8.45 (brs, 1H), 8.58 (brs, 1H) | m/z (EI) 367 (M⁺) | Example 18 |
| 99 | 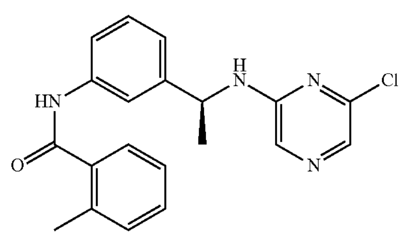 [SMILES: Cc1ccccc1C(=O)Nc1cccc([C@H](C)Nc2cncc(Cl)n2)c1] | δ 1.60 (d, J 6.9 Hz, 3H), 2.51 (s, 3H), 4.86-4.95 (m, 1H), 5.17 (d, J 6.3 Hz, 1H), 7.15 (d, J 8.1 Hz, 1H), 7.23-7.40 (m, 4H), 7.46-7.54 (m, 3H), 7.64 (brs, 1H), 7.73 (brs, 1H), 7.79 (s, 1H) | m/z (EI) 366 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 100 | (structure) | δ 1.63 (d, J 7.2 Hz, 3H), 2.43 (s, 3H), 3.84 (s, 3H,), 4.98-5.06 (m, 1H), 5.10 (d, J 6.3 Hz, 1H), 6.93-6.97 (m, 1H), 7.21 (brd, J 7.5 Hz, 1H), 7.32-7.37 (m, 4H), 7.47-7.50 (m, 2H), 7.52-7.56 (m, 1H), 7.62-7.66 (m, 1H), 7.68 (brs, 1H), 7.75 (s, 2H), 7.88 (brs, 1H), 8.27 (s, 1H) | m/z (EI) 438 (M⁺) | Example 7 |
| 101 | (structure) | | m/z (EI) 432 (M⁺) | Example 16 |
| 102 | (structure) | δ 1.56 (d, J 6.3 Hz, 3H), 1.63-1.81 (m, 2H), 1.83-1.97 (m, 2H), 2.42 (s, 3H), 3.23-3.37 (m, 2H), 3.62-3.78 (m, 2H), 4.73-4.87 (m, 3H), 7.11-7.38 (m, 16H), 7.45 (d, J 8.7 Hz, 1H), 7.64-7.72 (m, 3H), 7.92 (brs, 1H) | m/z (EI) 413 (M⁺ − H − OP(O)(OPh)₂) | Example 19 |

TABLE 1-continued

| Compound Number | Structure | $^1$H nmr data (in CDCl$_3$ unless otherwise stated) | Mass spectral data | Synthetic Method |
|---|---|---|---|---|
| 103 | 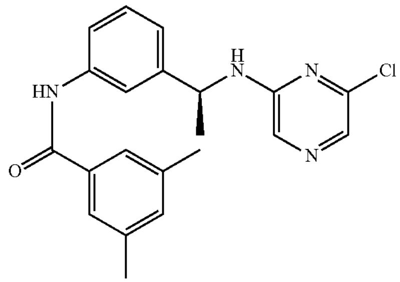 [SMILES: Cc1cc(C)cc(C(=O)Nc2cccc([C@H](C)Nc3cncc(Cl)n3)c2)c1] | δ 1.58 (d, J 6.6 Hz, 3H), 2.38 (s, 6H), 4.85-4.94 (m, 1H), 5.22 (d, J 6.6 Hz, 1H), 7.13 (d, J 7.8 Hz, 1H), 7.18 (s, 1H), 7.33 (t, J 7.8 Hz, 1H), 7.46 (s, 2H), 7.50-7.54 (m, 1H), 7.63 (s, 1H), 7.72 (t, J 1.8 Hz, 1H), 7.78 (s, 1H), 7.91 (brs, 1H) | m/z (EI) 380 (M$^+$) | Example 1 |
| 104 | 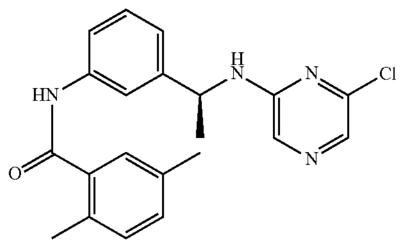 [SMILES: Cc1ccc(C)c(C(=O)Nc2cccc([C@H](C)Nc3cncc(Cl)n3)c2)c1] | δ 1.60 (d, J 6.9 Hz, 3H), 2.36 (s, 3H), 2.46 (s, 3H), 4.86-4.95 (m, 1H), 5.16 (d, J 6.6 Hz, 1H), 7.13-7.20 (m, 3H), 7.29 (s, 1H), 7.34 (t, J 7.8 Hz, 1H), 7.46-7.50 (m, 2H), 7.64 (s, 1H) 7.72 (brs, 1H), 7.79 (s, 1H) | m/z (EI) 380 (M$^+$) | Example 1 |
| 105 | 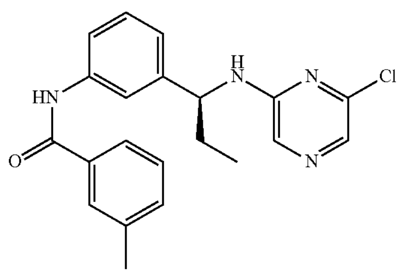 [SMILES: CC[C@H](Nc1cncc(Cl)n1)c1cccc(NC(=O)c2cccc(C)c2)c1] | δ 0.98 (t, J 7.5 Hz, 3H), 1.86-1.96 (m, 2H), 2.43 (s, 3H), 4.58-4.65 (m, 1H), 5.17 (d, J 7.5 Hz, 1H), 7.11 (brd, J 7.8 Hz, 1H), 7.31-7.38 (m, 3H), 7.48-7.52 (m, 1H), 7.63-7.71 (m, 4H), 7.78 (s, 1H), 7.82 (brs, 1H) | m/z (EI) 380 (M$^+$) | Example 1 |

TABLE 1-continued

| Compound Number | Structure | ¹H nmr data (in CDCl₃ unless otherwise stated) | Mass spectral data | Synthetic Method |
|---|---|---|---|---|
| 106 | 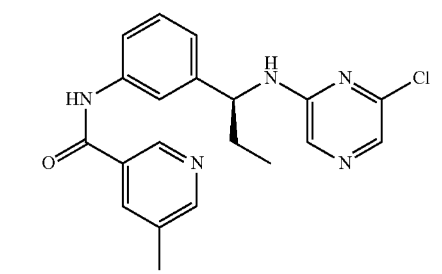 | δ 0.98 (t, J 7.8 Hz, 3H), 1.86-1.96 (m, 2H), 2.41 (s, 3H), 4.59-4.66 (m, 1H), 5.30 (d, J 6.9 Hz, 1H), 7.14 (d, J 7.8 Hz, 1H), 7.34 (t, J 7.8 Hz, 1H), 7.50-7.53 (m, 1H), 7.63 (s, 1H), 7.69 (t, J 1.8 Hz, 1H), 7.77 (s, 1H), 7.99 (brs, 1H), 8.01 (brs, 1H), 8.59 (brs, 1H), 8.88 (brs, 1H) | m/z (EI) 381 (M⁺) | Example 1 |
| 107 | 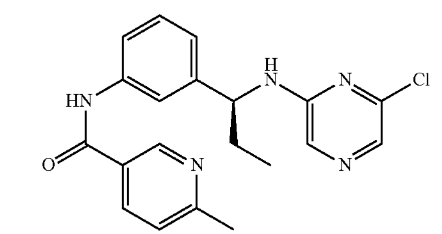 [SMILES: CC[C@H](Nc1cncc(Cl)n1)c1cccc(NC(=O)c2ccc(C)nc2)c1] | δ 0.99 (t, J 7.2 Hz, 3H), 1.87-1.97 (m, 2H), 2.65 (s, 3H), 4.59-4.66 (m, 1H), 5.19 (d, J 6.9 Hz, 1H), 7.15 (d, J 7.8 Hz, 1H), 7.30 (t, J 8.1 Hz, 1H), 7.36 (t, J 7.8 Hz, 1H), 7.48-7.51 (m, 1H), 7.64 (s, 1H), 7.71 (t, J 7.8 Hz, 1H), 7.79 (s, 1H), 7.84 (brs, 1H), 8.09 (dd, J 8.1, 2.1 Hz, 1H), 8.98 (d, J 2.1 Hz, 1H) | m/z (EI) 381 (M⁺) | Example 1 |
| 108 | 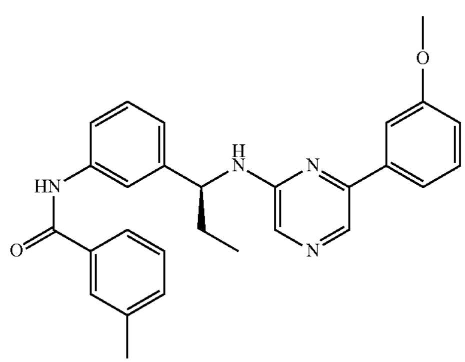 [SMILES: CC[C@H](Nc1cncc(-c2cccc(OC)c2)n1)c1cccc(NC(=O)c2cccc(C)c2)c1] | δ 1.00 (t, J 7.2 Hz, 3H), 1.86-2.02 (m, 2H), 2.41 (s, 3H), 3.83 (s, 3H), 4.71-4.78 (m, 1H), 5.14 (d, J 6.3 Hz, 1H), 6.92-6.96 (m, 1H), 7.16 (d, J 7.2 Hz, 1H), 7.29-7.36 (m, 4H), 7.45-7.48 (m, 2H), 7.51-7.55 (m, 1H), 7.61-7.67 (m, 2H), 7.72 (t, J 1.8 Hz, 1H), 7.74 (s, 1H), 7.90 (brs, 1H), 8.24 (s, 1H) | m/z (EI) 452 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 109 | 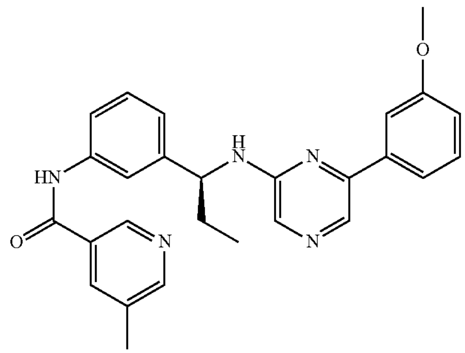 [SMILES: CC[C@H](Nc1cncc(-c2cccc(OC)c2)n1)c1cccc(NC(=O)c2cncc(C)c2)c1] | δ 1.00 (t, J 7.5 Hz, 3H), 1.84-2.01 (m, 2H), 2.34 (s, 3H), 3.83 (s, 3H), 4.71-4.78 (m, 1H), 5.35 (d, J 6.9 Hz, 1H), 6.91-6.95 (m, 1H), 7.19 (d, J 7.8 Hz, 1H), 7.29-7.35 (m, 2H), 7.43-7.46 (m, 2H), 7.53-7.56 (m, 1H), 7.70 (t, J 1.5 Hz, 1H), 7.72 (s, 1H), 7.95 (brs, 1H), 8.20 (s, 1H), 8.43 (brs, 1H), 8.53 (d, J 2.4 Hz, 1H), 8.86 (d, J 2.1 Hz, 1H) | m/z (EI) 453 (M⁺) | Example 7 |
| 110 | 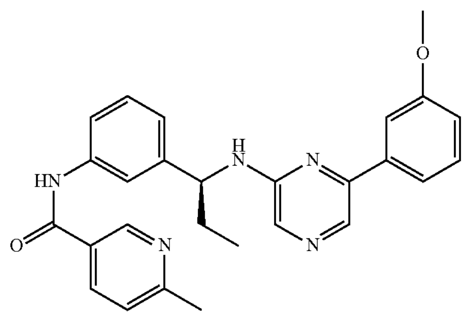 [SMILES: CC[C@H](Nc1cncc(-c2cccc(OC)c2)n1)c1cccc(NC(=O)c2ccc(C)nc2)c1] | δ 0.97 (t, J 7.2 Hz, 3H), 1.81-1.97 (m, 2H), 2.56 (s, 3H), 3.82 (s, 3H), 4.69-4.76 (m, 1H), 5.37 (d, J 6.6 Hz, 1H), 6.91-6.94 (m, 1H), 7.15 (s, 1H), 7.18 (s, 1H), 7.25-7.34 (m, 2H), 7.42-7.45 (m, 2H), 7.50 (d, J 9.0 Hz, 1H), 7.69 (brs, 1H), 7.70 (m, 1H), 8.01 (dd, J 8.4, 2.1 Hz, 1H), 8.19 (s, 1H), 8.50 (brs, 1H), 8.95 (d, J 1.8 Hz, 1H) | m/z (EI) 453 (M⁺) | Example 7 |
| 111 | 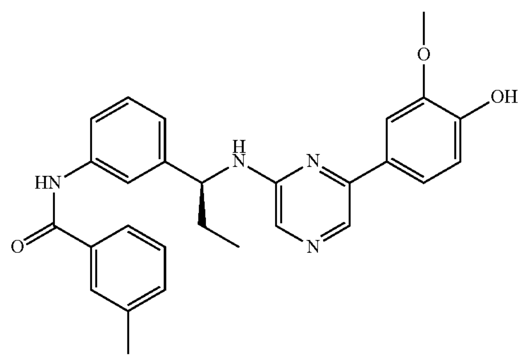 [SMILES: CC[C@H](Nc1cncc(-c2ccc(O)c(OC)c2)n1)c1cccc(NC(=O)c2cccc(C)c2)c1] | δ 1.00 (t, J 7.2 Hz, 3H), 1.87-1.99 (m, 2H), 2.40 (s, 3H), 3.92 (s, 3H), 4.67-4.74 (m, 1H), 5.16 (d, J 6.3 Hz, 1H), 6.06 (brs, 1H), 6.95 (d, J 8.4 Hz, 1H), 7.16 (d, J 7.8 Hz, 1H), 7.28-7.34 (m, 3H), 7.41 (dd, J 8.1, 2.4 Hz, 1H), 7.46-7.52 (m, 2H), 7.61-7.67 (m, 3H), 7.74 (s, 1H), 7.96 (s, 1H), 8.19 (s, 1H) | m/z (EI) 468 (M⁺) | Example 7 |

TABLE 1-continued

| Compound Number | Structure | ¹H nmr data (in CDCl₃ unless otherwise stated) | Mass spectral data | Synthetic Method |
|---|---|---|---|---|
| 112 | 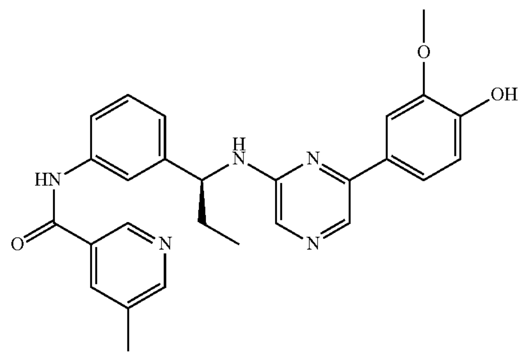 [SMILES: CC[C@H](Nc1cncc(-c2ccc(O)c(OC)c2)n1)c1cccc(NC(=O)c2cncc(C)c2)c1] | δ 1.00 (t, J 7.5 Hz, 3H), 1.84-2.00 (m, 2H), 2.35 (s, 3H), 3.90 (s, 3H), 4.68-4.74 (m, 1H), 5.26 (d, J 6.6 Hz, 1H), 6.37 (brs, 1H), 6.93 (d, J 8.1 Hz, 1H), 7.18 (d, J 7.2 Hz, 1H), 7.31 (t, J 7.8 Hz, 1H), 7.38 (dd, J 8.1, 1.8 Hz, 1H), 7.44 (d, J 1.8 Hz, 1H), 7.53 (d, J 7.5 Hz, 1H), 7.66 (s, 1H), 7.72 (s, 1H), 7.96 (s, 1H), 8.16 (s, 1H), 8.42 (brs, 1H), 8.52 (d, J 1.2 Hz, 1H), 8.86 (d, J 1.8 Hz, 1H) | m/z (ESI) 470 [M + H]⁺ | Example 7 |
| 113 | 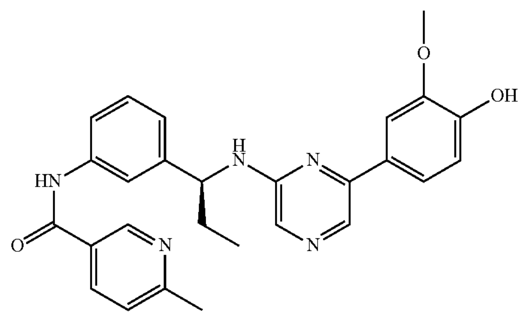 [SMILES: CC[C@H](Nc1cncc(-c2ccc(O)c(OC)c2)n1)c1cccc(NC(=O)c2ccc(C)nc2)c1] | δ 0.97 (t, J 7.2 Hz, 3H), 1.80-1.96 (m, 2H), 2.55 (s, 3H), 3.86 (s, 3H), 4.65-4.71 (m, 1H), 5.29 (d, J 6.3 Hz, 1H), 6.74 (brs, 1H), 6.90 (d, J 8.4 Hz, 1H), 7.14-7.18 (m, 2H), 7.27 (t, J 7.8 Hz, 1H), 7.35 (dd, J 8.4, 1.8 Hz, 1H), 7.41 (d, J 2.4 Hz, 1H), 7.48-7.51 (m, H), 7.62 (s, 1H), 7.69 (s, 1H), 8.02 (dd, J 8.4, 2.4 Hz, 1H), 8.12 (s, 1H), 8.51 (s, 1H), 8.95 (d, J 1.8 Hz, 1H) | m/z (ESI) 470 [M + H]⁺ | Example 7 |
| 114 | 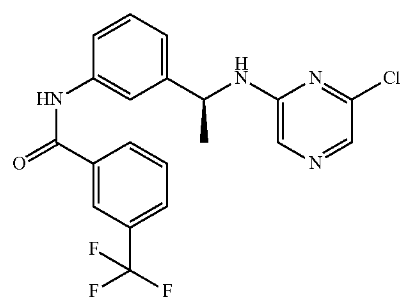 [SMILES: C[C@H](Nc1cncc(Cl)n1)c1cccc(NC(=O)c2cccc(C(F)(F)F)c2)c1] | δ 1.60 (d, J 6.3 Hz, 3H), 4.87-4.95 (m, 1H), 5.13 (d, J 7.2 Hz, 1H), 7.19 (d, J 7.8 Hz, 1H), 7.37 (t, J 7.8 Hz, 1H), 7.52-7.55 (m, 1H), 7.62-7.67 (m, 2H), 7.72 (m, 1H), 7.80-7.88 (m, 3H), 8.06 (d, J 7.8 Hz, 1H), 8.13 (brs, 1H) | m/z (ESI) 421 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 115 | 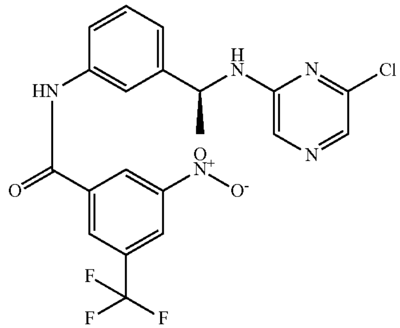 | CD₃OD δ 1.56 (d, J 6.6 Hz, 3H), 5.05 (q, J 6.6 Hz, 1H), 7.24 (d, J 9.0 Hz, 1H), 7.36 (t, J 7.8 Hz, 1H), 7.60 (s, 1H), 7.61-7.64 (m, 1H), 7.79 (brs, 2H), 8.66 (s, 1H), 8.71 (brs, 1H), 9.06 (brs, 1H) | m/z (EI) 465 (M⁺) | Example 1 |
| 116 | 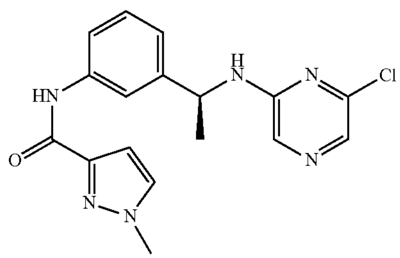 [SMILES: C[C@H](Nc1cncc(Cl)n1)c1cccc(NC(=O)c2ccn(C)n2)c1] | δ 1.60 (d, J 6.9 Hz, 3H), 3.97 (s, 3H), 4.86-4.94 (m, 1H), 5.14 (d, J 6.9 Hz, 1H), 6.87 (d, J 2.7 Hz, 1H), 7.11 (d, J 7.8 Hz, 1H), 7.33 (t, J 7.8 Hz, 1H), 7.41 (d, J 2.1 Hz, 1H), 7.54-7.57 (m, 1H), 7.65 (s, 1H), 7.80 (brs, 2H), 8.70 (brs, 1H) | m/z (EI) 356 (M⁺) | Example 1 |
| 117 | 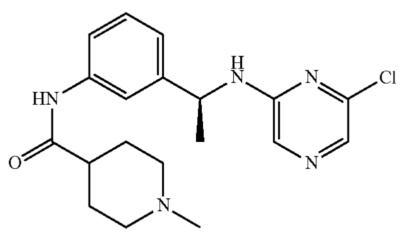 [SMILES: C[C@H](Nc1cncc(Cl)n1)c1cccc(NC(=O)C2CCN(C)CC2)c1] | δ 1.56 (d, J 6.9 Hz, 3H), 1.85-2.07 (m, 6H), 2.16-2.26 (m, 1H), 2.30 (s, 3H), 2.92-2.97 (m, 2H), 4.81-4.90 (m, 1H), 5.09 (d, J 7.2 Hz, 1H), 7.08-7.11 (m, 1H), 7.19 (brs, 1H), 7.25-7.35 (m, 2H), 7.61 (s, 1H), 7.65 (brs, 1H), 7.79 (s, 1H) | m/z (EI) 373 (M⁺) | Example 1 |

TABLE 1-continued

| Compound Number | Structure | ¹H nmr data (in CDCl₃ unless otherwise stated) | Mass spectral data | Synthetic Method |
|---|---|---|---|---|
| 118 | [structure: 6-chloropyrazin-2-yl amino-CH(CH₃)-phenyl with NH-C(O)-N-methylpiperidin-3-yl] | δ 1.51 (d, J 6.9 Hz, 3H), 1.87-1.97 (m, 5H), 2.18-2.26 (m, 1H), 2.27 (s, 3H), 2.74 (s, 1H), 2.90 (m, 2H), 4.80-4.91 (m, 1H), 5.57 (d, J 6.9 Hz, 1H), 7.07 (d, J 7.8 Hz, 1H), 7.22-7.27 (t, J 7.8 Hz, 1H), 7.37 (d, J 8.7 Hz, 1H), 7.60 (s, 1H), 7.62 (brs, 1H), 7.73 (s, 1H), 7.89 (brs, 1H) | m/z (EI) 373 (M⁺) | Example 1 |
| 119 | [structure: 6-chloropyrazin-2-yl amino-CH(CH₃)-phenyl with NH-C(O)-3-bromophenyl] | δ 1.56 (d, J 6.9 Hz, 3H), 4.84-4.93 (m, 1H), 5.20 (d, J 6.9 Hz, 1H), 7.14 (d, J 7.5 Hz, 1H), 7.30-7.36 (m, 2H), 7.48-7.52 (m, 1H), 7.61 (s, 1H), 7.64-7.69 (m, 2H), 7.75-7.78 (m, 2H), 7.97-7.99 (m, 2H) | m/z (ESI) 431, 433, 435 [M + H]⁺ | Example 1 |
| 120 | [structure: pyridin-4-yl-CH(NH₂)- with pyridin-2-yl NH-C(O)-3-methylphenyl] | δ 1.43 (d, J 6.9 Hz, 3H), 2.44 (s, 3H), 4.16 (q, J 7.2 Hz, 1H), 7.10-7.12 (m, 1H), 7.38-7.40 (m, 2H), 7.70-7.75 (m, 2H), 8.24 (d, J 6.0 Hz, 1H), 8.39 (brs, 1H), 8.60 (brs, 1H) | m/z (ESI) 256 [M + H]⁺ | |

TABLE 1-continued

| Compound Number | Structure | ¹H nmr data (in CDCl₃ unless otherwise stated) | Mass spectral data | Synthetic Method |
|---|---|---|---|---|
| 121 | 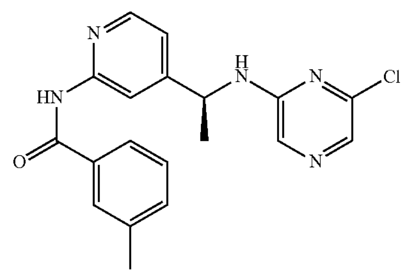 | δ 1.62 (d, J 6.9 Hz, 3H), 2.43 (s, 3H), 4.94-5.03 (m, 1H), 5.18 (d, J 6.6 Hz, 1H), 7.07 (dd, J 4.8, 1.2 Hz, 1H), 7.38-7.40 (m, 2H), 7.70-7.73 (m, 3H), 7.82 (s, 1H), 8.25 (d, J 5.1 Hz, 1H), 8.44 (brs, 1H), 8.65 (brs, 1H) | m/z (ESI) 368 [M + H]⁺ | Example 18 |
| 122 | 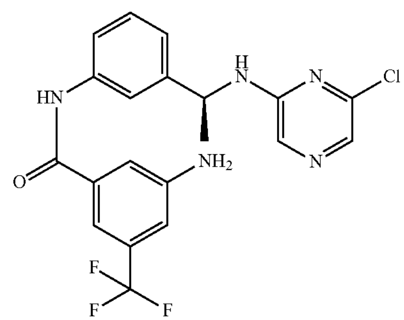 | δ 1.59 (d, J 6.9 Hz, 3H), 4.07 (s, 2H), 4.85-4.93 (m, 1H), 5.14 (d, J 6.9 Hz, 1H), 7.04 (s, 1H), 7.16 (d, J 7.5 Hz, 1H), 7.33-7.38 (m, 3H), 7.49-7.53 (m, 1H), 7.63 (s, 1H), 7.70 (t, J 1.5 Hz, 1H), 7.80 (s, 1H), 7.81 (brs, 1H) | m/z (ESI) 436 [M + H]+ | Example 20 |
| 123 | 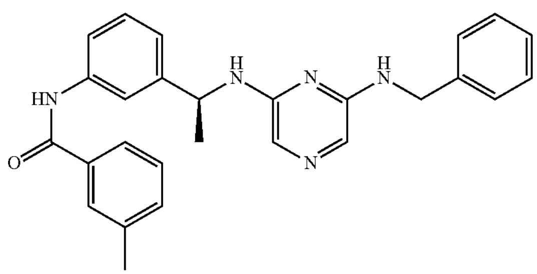 [SMILES: Cc1cccc(C(=O)Nc2cccc([C@H](C)Nc3cncc(NCc4ccccc4)n3)c2)c1] | δ 1.55 (d, J 6.9 Hz, 3H), 2.44 (s, 3H), 4.39-4.53 (m, 2H), 4.62 (t, J 4.6 Hz, 1H), 4.69 (d, J 6.6 Hz, 1H), 4.80-4.89 (m, 1H), 7.11 (s, 1H), 7.13 (d, J 7.5 Hz, 1H), 7.18 (s, 1H), 7.26-7.40 (m, 8H), 7.53-7.57 (m, 1H), 7.62-7.65 (m, 2H), 7.67 (brs, 1H), 7.80 (brs, 1H) | m/z (ESI) 438 [M + H]+ | Example 21 |

TABLE 1-continued

| Compound Number | Structure | 1H nmr data (in CDCl3 unless otherwise stated) | Mass spectral data | Synthetic Method |
|---|---|---|---|---|
| 124 | 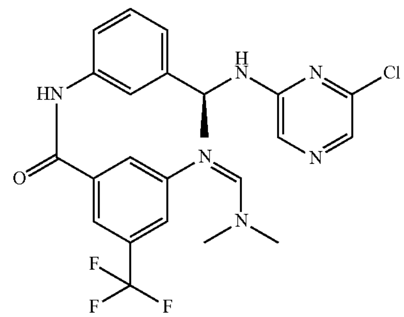 [SMILES: C[C@H](Nc1cncc(Cl)n1)c1cccc(NC(=O)c2cc(/N=C\N(C)C)cc(C(F)(F)F)c2)c1] | δ 1.61 (d, J 6.6 Hz, 3H), 3.09 (brs, 6H), 4.87-4.96 (m, 1H), 5.12 (d, J 6.6 Hz, 1H), 7.17 (brd, J 7.5 Hz, 1H), 7.34-7.39 (m, 2H), 7.50-7.54 (m, 1H), 7.59 (brs, 1H), 7.64 (s, 1H), 7.65 (s, 1H), 7.71 (brs, 1H), 7.74 (brs, 1H), 7.81 (s, 1H), 7.86 (brs, 1H) | m/z (ESI) 491 [M + H]+ | Example 22 |
| 125 | 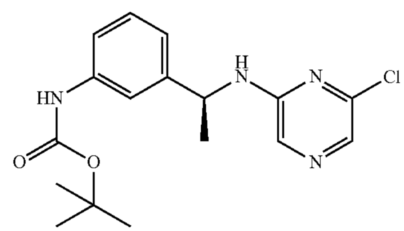 [SMILES: C[C@H](Nc1cncc(Cl)n1)c1cccc(NC(=O)OC(C)(C)C)c1] | δ 1.52 (s, 9H), 1.57 (d, J 6.6 Hz, 3H), 4.80-4.89 (m, 1H), 5.09 (d, J 6.6 Hz, 1H), 6.49 (brs, 1H), 7.01-7.04 (m, 1H), 7.16-7.20 (m, 1H), 7.26 (t, J 7.8 Hz, 1H), 7.48 (brs, 1H), 7.62 (s, 1H), 7.80 (s, 1H) | m/z (ESI) 394 [M + 2Na]+, 371 [M + Na]+ | |
| 126 | 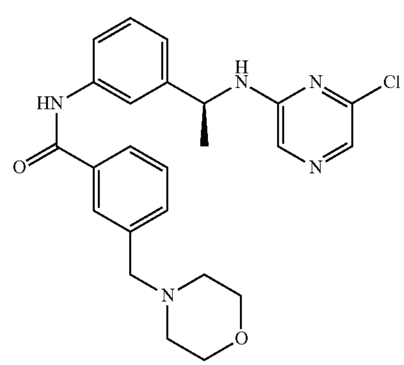 [SMILES: C[C@H](Nc1cncc(Cl)n1)c1cccc(NC(=O)c2cccc(CN3CCOCC3)c2)c1] | δ 1.57 (d, J 6.9 Hz, 3H), 2.45 (t, J 4.5 Hz, 4H), 3.54 (s, 2H), 3.70 (t, J 4.5 Hz, 4H), 4.85-4.94 (m, 1H), 5.29 (d, J 6.9 Hz, 1H), 7.13 (d, J 7.5 Hz, 1H), 7.32 (t, J 7.8 Hz, 1H), 7.42 (t, J 7.8 Hz, 1H), 7.50-7.54 (m, 2H), 7.62 (s, 1H), 7.73-7.75 (m, 2H), 7.76 (s, 1H), 7.84 (t, J 4.5 Hz, 1H), 8.09 (brs, 1H) | m/z (ESI) 452 [M + H]+ | Example 1 |

TABLE 1-continued

| Compound Number | Structure | ¹H nmr data (in CDCl₃ unless otherwise stated) | Mass spectral data | Synthetic Method |
|---|---|---|---|---|
| 127 | 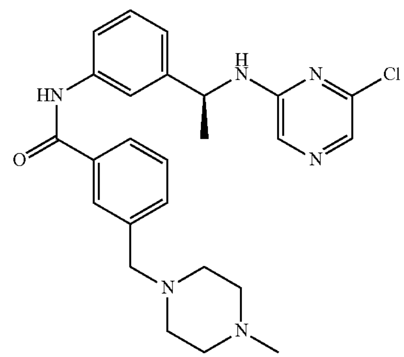 [SMILES: C[C@H](Nc1cncc(Cl)n1)c1cccc(NC(=O)c2cccc(CN3CCN(C)CC3)c2)c1] | δ 1.59 (d, J 6.5 Hz, 3H), 2.29 (s, 3H), 2.40-2.59 (m, 8H), 3.57 (s, 2H), 4.88-4.93 (m, 1H), 5.17 (d, J 7.0 Hz, 1H), 7.14 (d, J 8.0 Hz, 1H), 7.34 (t, J 8.0 Hz, 1H), 7.43 (t, J 8.0 Hz, 1H), 7.50-7.53 (m, 2H), 7.64 (s, 1H), 7.76-7.78 (m, 2H), 7.79 (s, 1H), 7.83 (s, 1H), 7.97 (brs, 1H) | m/z (ESI) 465 [M + H]⁺ | Example 1 |
| 128 | 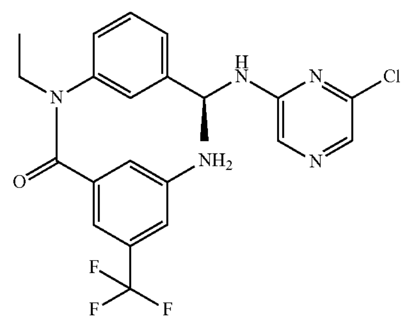 [SMILES: CCN(C(=O)c1cc(N)cc(C(F)(F)F)c1)c1cccc([C@H](C)Nc2cncc(Cl)n2)c1] | δ 1.22 (t, J 6.9 Hz, 3H), 1.43 (d, J 6.9 Hz, 3H), 3.86 (brs, 2H), 3.93-4.00 (m, 2H), 4.68-4.77 (m, 1H), 4.95 (d, J 6.0 Hz, 1H), 6.67 (brs, 1H), 6.72-6.74 (m, 2H), 6.95-7.00 (m, 2H), 7.15-7.19 (m, 1H), 7.26 (t, J 7.8 Hz, 1H), 7.47 (s, 1H), 7.82 (s, 1H) | m/z (ESI) 464 [M + H]⁺ | Example 23 |
| 129 | 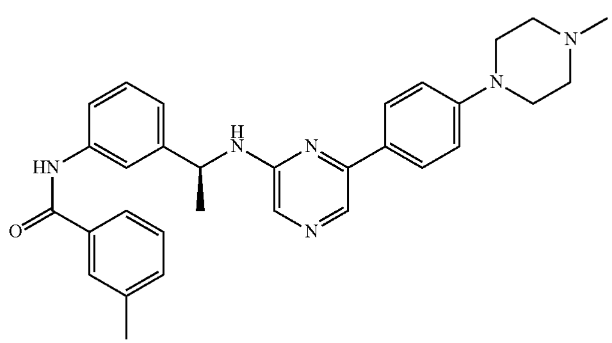 [SMILES: Cc1cccc(C(=O)Nc2cccc([C@H](C)Nc3cncc(-c4ccc(N5CCN(C)CC5)cc4)n3)c2)c1] | CDCl₃ + CD₃OD δ 1.60 (d, J 6.3 Hz, 3H), 2.34 (s, 3H), 2.81 (s, 3H), 2.95-3.06 (m, 3H), 3.47-3.53 (m, 4H), 3.67-3.77 (m, 1H), 5.07 (m, 1H), 6.84 (brd, J 8.7 Hz, 2H), 7.14 (d, J 7.8 Hz, 1H), 7.28-7.30 (m, 2H), 7.60-7.73 (m, 7H), 7.82 (brs, 1H), 7.87 (brs, 1H) | m/z (ESI) 507 [M + H]⁺ | Example 2 |

TABLE 1-continued

| Compound Number | Structure | ¹H nmr data (in CDCl₃ unless otherwise stated) | Mass spectral data | Synthetic Method |
|---|---|---|---|---|
| 130 | 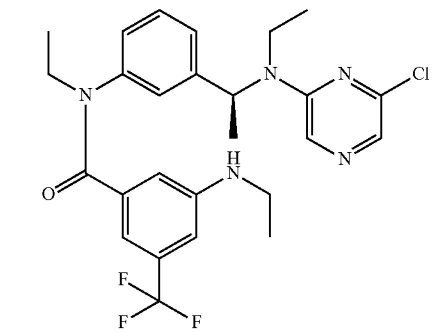 [SMILES: CCNc1cc(C(=O)N(CC)c2cccc([C@H](C)N(CC)c3cncc(Cl)n3)c2)cc(C(F)(F)F)c1] | δ 0.96 (t, J 6.9 Hz, 3H), 1.20 (t, J 6.9 Hz, 3H), 1.21 (t, J 6.9 Hz, 3H), 1.45 (d, J 7.2 Hz, 3H), 2.84-3.07 (m, 4H), 3.76 (brs, 1H), 3.96 (q, J 6.9 Hz, 2H), 5.82 (q, J 6.9 Hz, 1H), 6.59 (s, 1H), 6.66 (s, 1H), 6.68 (d, J 1.8 Hz, 1H), 6.80 (s, 1H), 7.05-7.12 (m, 2H), 7.27 (t, J 8.1 Hz, 1H), 7.69 (s, 1H), 7.77 (s, 1H) | m/z (ESI) 520 [M + H]⁺ | Example 23 |
| 131 | 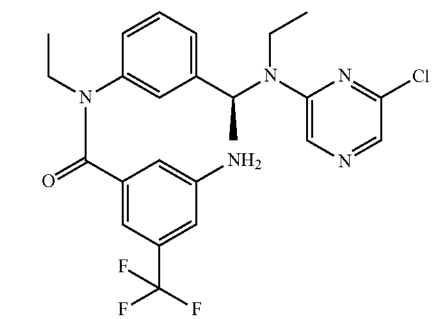 [SMILES: CCN(C(=O)c1cc(N)cc(C(F)(F)F)c1)c1cccc([C@H](C)N(CC)c2cncc(Cl)n2)c1] | δ 0.99 (t, J 7.2 Hz, 3H), 1.20 (t, J 7.2 Hz, 3H), 1.48 (d, J 6.6 Hz, 3H), 2.83-3.12 (m, 2H), 3.85 (brs, 2H), 3.94 (q, J 7.2 Hz, 3H), 5.81 (q, J 6.6 Hz, 1H), 6.70 (t, J 2.1 Hz, 2H), 6.78 (s, 1H), 6.82 (s, 1H), 7.03-7.13 (m, 2H), 7.27 (t, J 7.8 Hz, 1H), 7.70 (s, 1H), 7.78 (s, 1H) | m/z (ESI) 492 [M + H]⁺ | Example 23 |
| 132 | 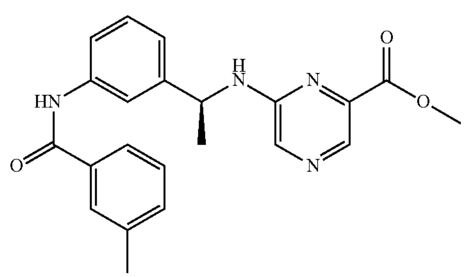 [SMILES: COC(=O)c1cncc(N[C@@H](C)c2cccc(NC(=O)c3cccc(C)c3)c2)n1] | δ 1.59 (d, J 6.9 Hz, 3H), 2.41 (s, 3H), 3.96 (s, 3H), 4.82-4.91 (m, 1H), 5.39 (d, J 6.6 Hz, 1H), 7.14 (d, J 7.8 Hz, 1H), 7.29-7.36 (m, 3H), 7.54-7.58 (m, 1H), 7.62-7.66 (m, 1H), 7.68 (s, 1H), 7.72 (t, J 1.8 Hz, 1H), 7.88 (s, 1H), 7.96 (brs, 1H), 8.51 (s, 1H) | m/z (ESI) 391 [M + H]⁺ | Example 24 |

TABLE 1-continued

| Compound Number | Structure | ¹H nmr data (in CDCl₃ unless otherwise stated) | Mass spectral data | Synthetic Method |
|---|---|---|---|---|
| 133 | 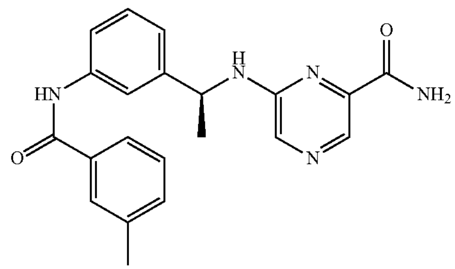 [SMILES: Cc1cccc(C(=O)Nc2cccc([C@H](C)Nc3cncc(C(N)=O)n3)c2)c1] | δ 1.62 (d, J 6.9 Hz, 3H), 2.43 (s, 3H), 4.88-4.97 (m, 1H), 5.21 (d, J 6.0 Hz, 1H), 5.50 (brs, 1H), 7.14 (d, J 6.6 Hz, 1H), 7.29-7.37 (m, 5H), 7.61-7.65 (m, 1H), 7.67 (s, 1H), 7.87 (s, 1H), 7.96 (s, 1H), 8.04 (s, 1H), 8.58 (s, 1H) | m/z (ESI) 376 [M + H]⁺ | Example 24 |
| 134 | 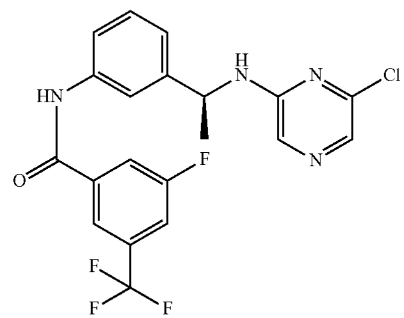 [SMILES: C[C@H](Nc1cncc(Cl)n1)c1cccc(NC(=O)c2cc(F)cc(C(F)(F)F)c2)c1] | δ 1.60 (d, J 6.9 Hz, 3H), 4.86-4.95 (m, 1H), 5.13 (d, J 6.6 Hz, 1H), 7.20 (d, J 7.8 Hz, 1H), 7.38 (t, J 7.8 Hz, 1H), 7.52 (s, 1H), 7.55 (s, 1H), 7.63 (s, 1H), 7.69 (s, 1H), 7.77-7.80 (m, 2H), 7.88 (s, 1H), 7.90 (s, 1H) | m/z (ESI) 439 [M + H]⁺ | Example 1 |
| 135 | 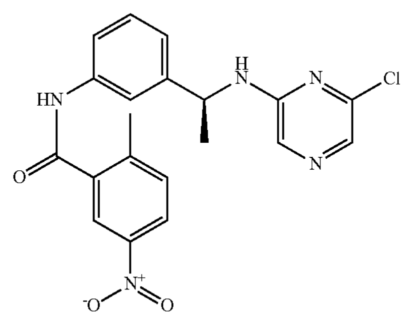 | δ 1.59 (d, J 7.2 Hz, 3H), 2.60 (s, 3H), 4.86-4.95 (m, 1H), 5.21 (d, J 6.6 Hz, 1H), 7.19 (d, J 7.8 Hz, 1H), 7.36 (d, J 7.9 Hz, 1H), 7.44 (d, J 8.7 Hz, 1H), 7.53 (d, J 7.5 Hz, 1H), 7.63 (s, 1H), 7.69 (s, 1H), 7.76 (s, 1H), 7.88 (s, 1H), 8.18 (s, J 8.4 Hz, 1H), 8.32 (s, 1H) | m/z (ESI) 412 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 136 | [Structure: 3-methoxy-N-[3-(1-((5-chloropyrazin-2-yl)amino)ethyl)phenyl]benzamide] | δ 1.59 (d, J 6.9 Hz, 3H), 3.87 (s, 3H), 4.88-4.94 (m, 1H), 5.17 (d, J 6.6 Hz, 1H), 7.07-7.11 (m, 1H), 7.15 (d, J 7.8 Hz, 1H), 7.34 (t, J 7.7 Hz, 1H), 7.39 (d, J 4.8 Hz, 2H), 7.43-7.44 (m, 1H), 7.48-7.51 (m, 1H), 7.64 (s, 1H), 7.64-7.75 (m, 1H), 7.79 (s, 1H), 7.90 (s, 1H) | m/z (ESI) 383 [M + H]⁺ | Example 1 |
| 137 | [Structure: 5-amino-2-methyl-N-[3-(1-((5-chloropyrazin-2-yl)amino)ethyl)phenyl]benzamide] | δ 1.60 (d, J 6.6 Hz, 3H), 2.37 (s, 3H), 3.75 (brs, 2H), 4.86-4.94 (m, 1H), 5.18 (d, 6.3 Hz, 1H), 6.70 (dd, J 7.8, 2.7 Hz, 1H), 6.81 (d, 2.1 Hz, 1H), 7.04 (d, 8.1 Hz, 1H), 7.14 (d, 8.1 Hz, 1H), 7.33 (t, 7.8 Hz, 1H), 7.43-7.49 (m, 2H), 7.64 (s, 1H), 7.72 (s, 1H) | m/z (ESI) 382 [M + H]⁺ | Example 20 |
| 138 | [Structure: N¹-(1-(3-aminophenyl)ethyl)-5-chloropyrazin-2-amine] | δ 1.54 (d, J 6.3 Hz, 3H), 3.68 (brs, 2H), 4.70-4.79 (m, 1H), 5.05 (brd, J 6.3 Hz, 1H), 6.56-6.60 (m, 1H), 6.65 (t, J 1.8 Hz, 1H), 6.73 (d, J 7.8 Hz, 1H), 7.12 (t, J 7.8 Hz, 1H), 7.61 (s, 1H), 7.79 (s, 1H) | m/z (ESI) 249 [M + H]⁺ | Example 1 |
| 139 | [Structure: N-[3-(1-((5-chloropyrazin-2-yl)amino)ethyl)phenyl]furan-2-carboxamide] | δ 1.60 (d, J 6.3 Hz, 3H), 4.86-4.95 (m, 1H), 5.16 (d, J 6.6 Hz, 1H), 6.57 (dd, J 3.8, 1.7 Hz, 1H), 7.15 (d, J 7.8 Hz, 1H), 7.24 (d, J 3.6 Hz, 1H), 7.27 (s, 1H), 7.34 (t, J 7.8 Hz, 1H), 7.50-7.52 (m, 2H), 7.75 (s, 1H), 7.80 (s, 1H), 8.10 (s, 1H) | m/z (ESI) 343 [M + H]⁺ | Example 1 |

TABLE 1-continued

| Compound Number | Structure | $^1$H nmr data (in CDCl$_3$ unless otherwise stated) | Mass spectral data | Synthetic Method |
|---|---|---|---|---|
| 140 | 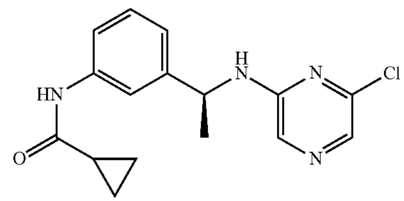 [SMILES: C[C@H](Nc1cncc(Cl)n1)c1cccc(NC(=O)C2CC2)c1] | CD$_3$OD δ 0.74-0.81 (m, 4H), 1.43 (d, J 7.2 Hz, 3H), 1.71-1.80 (m, 1H), 4.84-4.93 (m, 1H), 7.03 (d, J 7.8 Hz, 1H), 7.22 (t, J 7.8 Hz, 1H), 7.45 (d, J 8.4 Hz, 1H), 7.58 (s, 1H), 7.66 (s, 1H), 7.87 (s, 1H), 8.00 (d, J 7.2 Hz, 1H) | m/z (ESI) 317 [M + H]$^+$ | Example 1 |
| 141 | 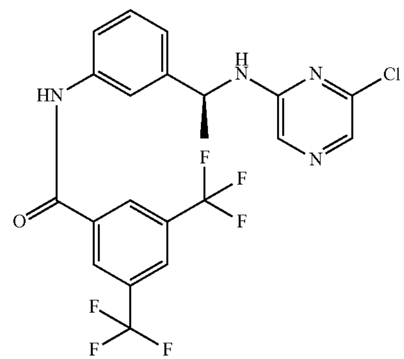 [SMILES: C[C@H](Nc1cncc(Cl)n1)c1cccc(NC(=O)c2cc(C(F)(F)F)cc(C(F)(F)F)c2)c1] | δ 1.59 (d, J 6.3 Hz, 3H), 4.85-4.94 (m, 1H), 5.13 (d, J 6.6 Hz, 1H), 7.20 (d, J 7.2 Hz, 1H), 7.37 (t, J 7.7 Hz, 1H), 7.52-7.55 (m, 1H), 7.62 (s, 1H), 7.68 (s, 1H), 7.79 (s, 1H), 7.98 (s, 1H), 8.06 (s, 1H), 8.31 (s, 2H) | m/z (ESI) 489 [M + H]$^+$ | Example 1 |
| 142 | 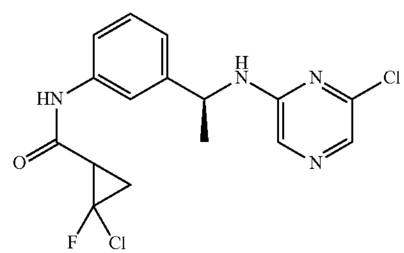 [SMILES: C[C@H](Nc1cncc(Cl)n1)c1cccc(NC(=O)C2CC2(F)Cl)c1] | δ 2.56 (d, J 6.3 Hz, 3H), 2.67-2.98 (m, 1H), 3.26-3.56 (m, 2H), 5.82-5.91 (m, 1H), 6.12 (d, J 6 Hz, 1H), 8.13 (d, J 7.2 Hz, 1H), 8.30-8.37 (m, 2H), 8.61-8.62 (m, 2H), 8.79 (s, 1H) | m/z (ESI) 369 [M + H]$^+$ | Example 1 |

TABLE 1-continued

| Compound Number | Structure | ¹H nmr data (in CDCl₃ unless otherwise stated) | Mass spectral data | Synthetic Method |
|---|---|---|---|---|
| 143 | [structure: N-[3-((1S)-1-{[6-(1H-imidazol-1-yl)pyrazin-2-yl]amino}ethyl)phenyl]-3-methylbenzamide] | δ 1.64 (d, J 6.9 Hz, 3H), 2.42 (s, 3H), 4.94-5.03 (m, 1H), 5.29 (d, J 6.3 Hz, 1H), 7.15-7.16 (m, 1H), 7.19 (t, J 1.5 Hz, 1H), 7.35-7.37 (m, 3H), 7.39-7.44 (m, 1H), 7.48-7.49 (m, 1H), 7.60-7.67 (m, 2H), 7.78 (s, 1H), 7.86 (t, J 1.8 Hz, 1H), 7.89 (s, 1H), 7.93 (s, 1H), 8.19 (s, 1H) | m/z (ESI) 399 [M + H]⁺ | Example 25 |
| 144 | [structure: N-[3-((1S)-1-{[6-chloropyrazin-2-yl]amino}ethyl)phenyl]-1H-benzimidazole-6-carboxamide] | CD₃OD δ 1.57 (d, J 6.9 Hz, 3H), 5.06 (q, J 6.9 Hz, 1H), 7.21 (d, J 9.0 Hz, 1H), 7.35 (t, J 7.8 Hz, 1H), 7.57-7.61 (m, 2H), 7.76-7.82 (m, 3H), 7.96 (d, J 8.4 Hz, 1H), 8.31 (brs, 1H), 8.59 (brs, 1H) | m/z (ESI) 393 [M + H]⁺ | Example 26 |
| 145 | [structure: N-[3-((1S)-1-{[6-chloropyrazin-2-yl]amino}ethyl)phenyl]-3-hydroxy-5-(trifluoromethyl)benzamide] | δ 1.53 (d, J 6.9 Hz, 3H), 4.83-4.92 (m, 1H), 5.44 (d, J 7.2 Hz, 1H), 7.14 (d, J 7.2 Hz, 1H), 7.18 (s, 1H), 7.26-7.36 (m, 2H), 7.45 (s, 1H), 7.62-7.80 (m, 4H), 8.45 (brs, 1H), 8.52 (brs, 1H) | m/z (ESI) 437 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 146 | [structure: N-[2-[(R)-1-(6-chloropyrazin-2-ylamino)ethyl]phenyl]-3-bromo-5-(trifluoromethyl)benzamide] | δ 1.60 (d, J 6.9 Hz, 3H), 4.86-4.95 (m, 1H), 5.11 (d, J 6.1 Hz, 1H), 7.19 (d, J 7.5 Hz, 1H), 7.37 (t, J 7.8 Hz, 1H), 7.51-7.54 (m, 1H), 7.63 (s, 1H), 7.67 (t, J 1.8 Hz, 1H), 7.80 (s, 1H), 7.84 (brs, 1H), 7.94 (brs, 1H), 8.03 (brs, 1H), 8.18 (t, J 1.2 Hz, 1H) | m/z (ESI) 499/501/503 [M + H]⁺ | Example 1 |
| 147 | [structure: morpholine-substituted pyrazine aminoethylphenyl 3-methylbenzamide] | δ 1.63 (d, J 6.3 Hz, 3H), 2.43 (s, 3H), 3.19-3.22 (m, 4H), 3.87-3.90 (m, 4H), 4.96-5.04 (m, 1H), 5.08 (d, J 6.6 Hz, 1H), 6.94-6.98 (m, 1H), 7.19-7.22 (m, 1H), 7.31-7.41 (m, 5H), 7.47-7.48 (m, 1H), 7.51-7.54 (m, 1H), 7.62-7.66 (m, 1H), 7.68 (s, 1H), 7.75-7.77 (m, 2H), 7.84 (s, 1H), 8.26 (s, 1H) | m/z (ESI) 494 [M + H]⁺ | Example 2 |
| 148 | [structure: 4-methylpiperazine-substituted pyrazine aminoethylphenyl 3-(trifluoromethyl)benzamide] | δ 1.63 (brs, 3H), 2.36 (s, 3H), 2.55-2.59 (m, 4H), 3.26-3.30 (m, 4H), 4.99 (brs, 2H), 6.95 (d, J 9.3 Hz, 2H), 7.24 (d, J 7.8 Hz, 1H), 7.36 (t, J 7.8 Hz, 1H), 7.51-7.66 (m, 3H), 7.72 (s, 1H), 7.79 (s, 1H), 7.83 (d, J 6.9 Hz, 2H), 7.89 (s, 1H), 8.04 (d, J 7.5 Hz, 1H), 8.13 (s, 1H), 8.22 (s, 1H) | m/z (ESI) 561 [M + H]⁺ | Example 2 |

TABLE 1-continued

| Compound Number | Structure | ¹H nmr data (in CDCl₃ unless otherwise stated) | Mass spectral data | Synthetic Method |
|---|---|---|---|---|
| 149 | 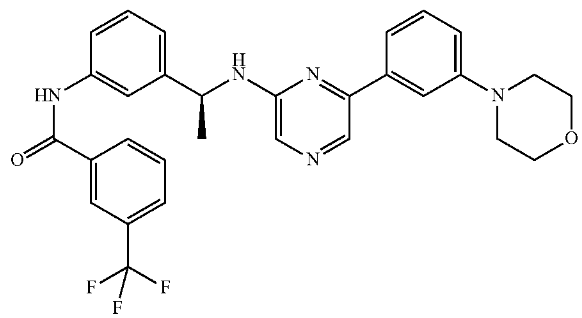 [SMILES: C[C@H](Nc1cncc(-c2cccc(N3CCOCC3)c2)n1)c1cccc(NC(=O)c2cccc(C(F)(F)F)c2)c1] | δ 1.64 (d, J 6.6 Hz, 3H), 3.18-3.21 (m, 4H), 3.86-3.89 (m, 4H), 4.95-5.07 (m, 2H), 6.93-6.99 (m, 1H), 7.30-7.39 (m, 4H), 7.45 (s, 1H), 7.51-7.55 (m, 1H), 7.60-7.65 (m, 1H), 7.74 (s, 2H), 7.79-7.85 (m, 2H), 8.03-8.05 (m, 1H), 8.11 (s, 1H), 8.26 (s, 1H) | m/z (ESI) 548 [M + H]⁺ | Example 2 |
| 150 | 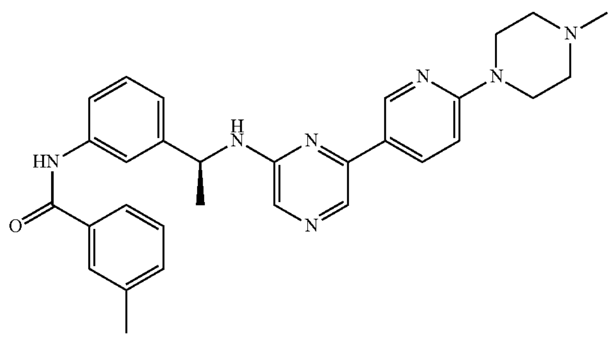 [SMILES: Cc1cccc(C(=O)Nc2cccc([C@H](C)Nc3cncc(-c4ccc(N5CCN(C)CC5)nc4)n3)c2)c1] | δ 1.62 (d, J 6.9 Hz, 3H), 2.35 (s, 3H), 2.43 (s, 3H), 2.50-2.53 (m, 4H), 3.61-3.65 (m, 4H), 4.96-5.04 (m, 2H), 6.67 (d, J 8.1 Hz, 1H), 7.18-7.21 (m, 1H), 7.31-7.37 (m, 3H), 7.50-7.53 (m, 1H), 7.61-7.70 (m, 3H), 7.75-7.77 (m, 1H), 7.83 (s, 1H), 8.01 (dd, J 9.2, 2.3 Hz, 1H), 8.18 (s, 1H), 8.75 (d, J 1.8 Hz, 1H) | m/z (ESI) 508 [M + H]⁺ | Example 2 |
| 151 | 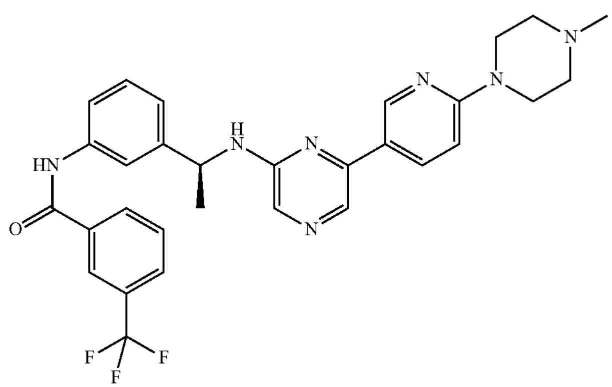 [SMILES: C[C@H](Nc1cncc(-c2ccc(N3CCN(C)CC3)nc2)n1)c1cccc(NC(=O)c2cccc(C(F)(F)F)c2)c1] | δ 1.63 (d, J 6.6 Hz, 3H), 2.35 (s, 3H), 2.50-2.53 (m, 4H), 3.62-3.65 (m, 4H), 4.95-5.07 (m, 2H), 6.68 (d, J 9.3 Hz, 1H), 7.22-7.24 (m, 1H), 7.36 (t, J 7.8 Hz, 1H), 7.52-7.56 (m, 1H), 7.60-7.67 (m, 2H), 7.73 (s, 1H), 7.80-7.82 (m, 1H), 7.89 (s, 1H), 7.98-8.02 (m, 1H), 8.05 (d, J 7.5 Hz, 1H), 8.13 (s, 1H), 8.18 (s, 1H), 8.75 (m, 1H) | m/z (ESI) 562 [M + H]⁺ | Example 2 |

TABLE 1-continued

| Compound Number | Structure | ¹H nmr data (in CDCl₃ unless otherwise stated) | Mass spectral data | Synthetic Method |
|---|---|---|---|---|
| 152 | (structure with chloropyrazine-NH, CF₃, and piperidine-Boc groups) | δ 1.49 (s, 9H), 1.60 (d, J 6.9 Hz, 4H), 1.60-1.70 (m, 2H), 1.82-1.86 (m, 2H), 2.56 (m, 1H), 2.75-2.86 (m, 2H), 4.25-4.29 (m, 2H), 4.85-4.94 (m, 1H), 5.14 (d, J 6.6 Hz, 1H), 7.18 (d, J 7.8 Hz, 1H), 7.36 (t, J 8 Hz, 1H), 7.53-7.57 (m, 1H), 7.63 (s, 2H), 7.71 (m, 1H) 7.79 (s, 1H), 7.91-7.92 (m, 2H), 8.02-8.04 (m, 1H) | m/z (ESI) 604 [M + H]⁺ | Example 1 |
| 153 | (structure with chloropyrazine-NH, CF₃, and piperidine groups) | δ 1.60 (d, J 6.9 Hz, 3H), 1.85-1.99 (m, 3H), 2.05 (s, 1H), 2.80-2.90 (m, 3H), 3.33-3.37 (m, 2H), 4.85-4.95 (m, 1H), 5.22 (d, J 6.6 Hz, 1H), 7.18 (d, J 7.8 Hz, 1H), 7.36 (t, J 8 Hz, 1H), 7.59 (d, J 8 Hz, 1H), 7.65 (s, 2H), 7.74-7.78 (m, 2H), 8.00-8.01 (m, 2H), 8.15 (s, 1H) | m/z (ESI) 504 [M + H]⁺ | Example 1 then 5 |

TABLE 1-continued
| Compound Number | Structure | ¹H nmr data (in CDCl₃ unless otherwise stated) | Mass spectral data | Synthetic Method |
|---|---|---|---|---|
| 154 | 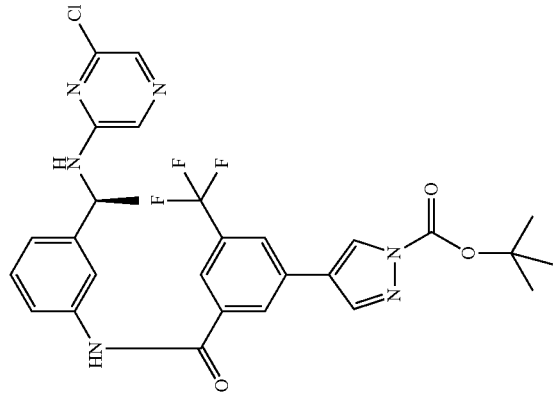 | δ 1.60 (d, J 6.9 Hz, 3H), 1.69 (s, 9H), 4.85-4.96 (m, 1H), 5.16 (d, J 6.6 Hz, 1H), 7.19 (d, J 7.8 Hz, 1H), 7.43 (t, J 8 Hz, 1H), 7.56-7.58 (m, 1H), 7.64 (s, 1H), 7.73 (s, 1H), 7.79 (s, 1H), 7.91 (s, 1H), 7.97 (s, 1H), 8.05-8.07 (m, 2H), 8.22 (s, 1H), 8.44 (s, 1H). | m/z (ESI) 587 [M + H]⁺ | Example 1 |
| 155 | 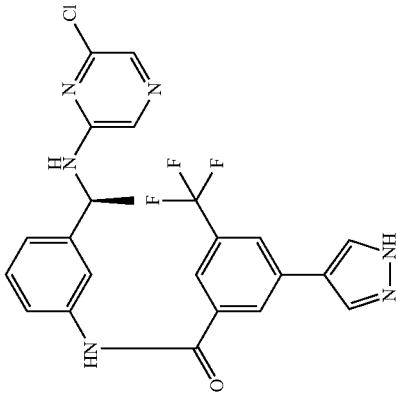 | CD₃OD δ 1.57 (d, J 7.5 Hz, 3H), 5.02-5.09 (m, 1H), 7.22 (d, J 7.8 Hz, 1H), 7.35 (t, J 7.8 Hz, 1H), 7.60-7.63 (m, 2H), 7.78 (s, 2H), 8.08 (s, 2H), 8.18 (brs, 2H), 8.42 (s, 1H). | m/z (ESI) 487 [M + H]⁺ | Example 1 then 5 |

TABLE 1-continued

| Compound Number | Structure | ¹H nmr data (in CDCl₃ unless otherwise stated) | Mass spectral data | Synthetic Method |
|---|---|---|---|---|
| 156 | 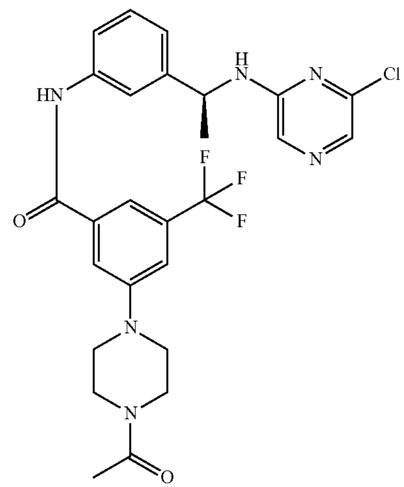 [SMILES: CC(=O)N1CCN(c2cc(C(=O)Nc3cccc([C@H](C)Nc4cncc(Cl)n4)c3)cc(C(F)(F)F)c2)CC1] | δ 1.59 (d, J 6.9 Hz, 3H), 2.14 (s, 3H), 3.22-3.32 (m, 4H), 3.63 (t, J 5.1 Hz, 2H), 3.76 (t, J 5.1 Hz, 2H), 4.85-4.94 (m, 1H), 5.24 (d, J 6.6 Hz, 1H), 7.17 (d, J 7.8 Hz, 1H), 7.23 (s, 1H), 7.35 (t, J 7.8 Hz, 1H), 7.47 (s, 1H), 7.56 (brd, J 7.8 Hz, 1H), 7.59 (s, 1H), 7.63 (s, 1H), 7.73 (s, 1H), 7.77 (s, 1H), 8.19 (brs, 1H) | m/z (ESI) 547 [M + H]⁺ | Example 1 |
| 157 | 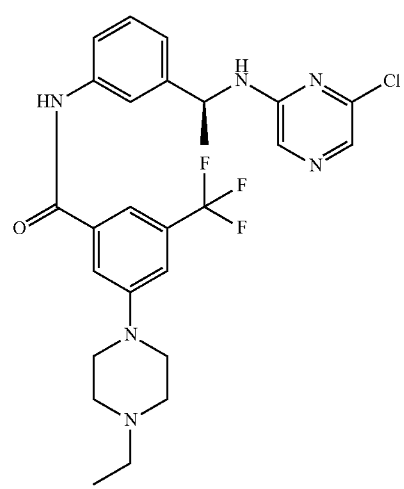 [SMILES: CCN1CCN(c2cc(C(=O)Nc3cccc([C@H](C)Nc4cncc(Cl)n4)c3)cc(C(F)(F)F)c2)CC1] | δ 1.14 (t, J 7.2 Hz, 3H), 1.57 (d, J 6.9 Hz, 3H), 2.49 (q, J 7.2 Hz, 2H), 2.60-2.64 (m, 4H), 3.31-3.34 (m, 4H), 4.84-4.93 (m, 1H), 5.24 (d, J 6.3 Hz, 1H), 7.15 (d, J 7.8 Hz, 1H), 7.23 (s, 1H), 7.33 (t, J 7.5 Hz, 1H), 7.41 (s, 1H), 7.51-7.54 (m, 1H), 7.57 (s, 1H), 7.62 (s, 1H), 7.71 (brs, 1H), 7.76 (s, 1H), 8.07 (brs, 1H) | m/z (ESI) 533 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 158 | 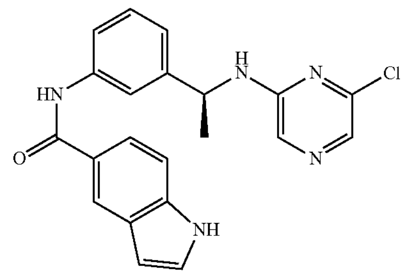 [SMILES: C[C@H](Nc1cncc(Cl)n1)c1cccc(NC(=O)c2ccc3[nH]ccc3c2)c1] | δ 1.55 (d, J 6.6 Hz, 3H), 4.82-4.91 (m, 1H), 5.24 (d, J 6.6 Hz, 1H), 6.61-6.63 (m, 1H), 7.09-7.12 (m, 1H), 7.27-7.34 (m, 2H), 7.42-7.39 (m, 1H), 7.50-7.53 (m, 1H), 7.60 (s, 1H), 7.69-7.73 (m, 1H), 7.75-7.76 (m, 2H), 8.06 (s, 1H), 8.19 (s, 1H), 8.69 (s, 1H) | m/z (ESI) 392 [M + H]⁺ | Example 26 |
| 159 | 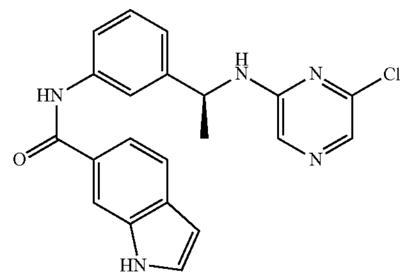 [SMILES: C[C@H](Nc1cncc(Cl)n1)c1cccc(NC(=O)c2ccc3cc[nH]c3c2)c1] | CD₃OD δ 1.55 (d, J 6.6 Hz, 3H), 5.00-5.06 (m, 1H), 6.51-6.52 (m, 1H), 7.16 (d, J 7.5 Hz, 1H), 7.33 (t, J 7.8 Hz, 1H), 7.40 (d, J 3.3 Hz, 1H), 7.54-7.58 (m, 2H), 7.61 (d, J 1.5 Hz, 1H), 7.62 (s, 1H), 7.74 (t, J 1.8 Hz, 1H), 7.76 (s, 1H), 8.02-8.03 (m, 1H) | m/z (ESI) 392 [M + H]⁺ | Example 26 |
| 160 | 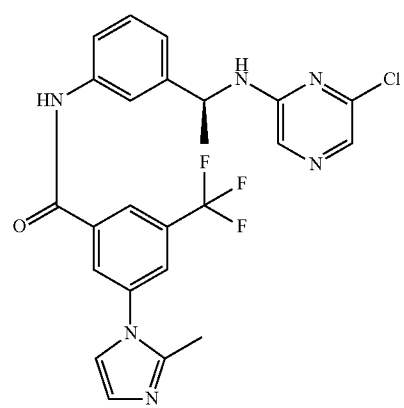 [SMILES: Cc1nccn1-c1cc(C(=O)Nc2cccc([C@H](C)Nc3cncc(Cl)n3)c2)cc(C(F)(F)F)c1] | δ 1.59 (d, J 6.9 Hz, 3H), 2.16 (brs, 3H), 4.85-4.94 (m, 1H), 5.15 (d, J 6.3 Hz, 1H), 6.96 (s, 1H), 7.02 (s, 1H), 7.18 (d, J 8.1 Hz, 1H), 7.36 (t, J 7.8 Hz, 1H), 7.60 (s, 1H), 7.71-7.76 (m, 3H), 7.86 (s, 1H), 8.17 (s, 1H), 8.38 (s, 1H), 9.81-10.11 (m, 1H) | m/z (ESI) 501 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 161 | 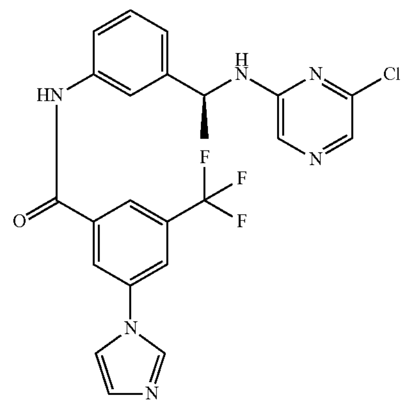 [SMILES: C[C@H](Nc1cncc(Cl)n1)c1cccc(NC(=O)c2cc(-n3ccnc3)cc(C(F)(F)F)c2)c1] | δ 1.59 (d, J 6.6 Hz, 3H), 4.85-4.94 (m, 1H), 5.24 (d, J 6.6 Hz, 1H), 7.18-7.20 (m, 2H), 7.33-7.39 (m, 2H), 7.56-7.64 (m, 2H), 7.74-7.79 (m, 3H), 7.87 (brs, 1H), 8.14-8.16 (m, 2H), 8.93 (brs, 1H) | m/z (ESI) 487 [M + H]⁺ | Example 1 |
| 162 | 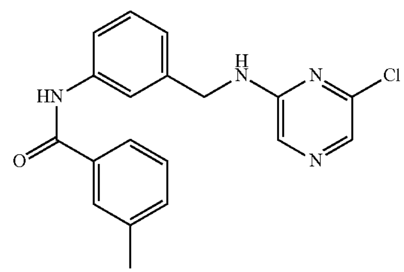 [SMILES: Cc1cccc(C(=O)Nc2cccc(CNc3cncc(Cl)n3)c2)c1] | δ 2.42 (s, 3H), 4.56 (d, J 5.7 Hz, 2H), 5.21 (t, J 5.7 Hz, 2H), 7.11-7.14 (m, 1H), 7.31-7.37 (m, 3H), 7.49-7.52 (m, 1H), 7.61-7.65 (m, 1H), 7.67 (brs, 1H), 7.71 (t, J 1.8 Hz, 1H), 7.76 (d, J 0.3 Hz, 1H), 7.81 (d, J 0.3 Hz, 1H), 7.87 (brs, 1H) | m/z (ESI) 353 [M + H]⁺ | Example 1 |
| 163 | 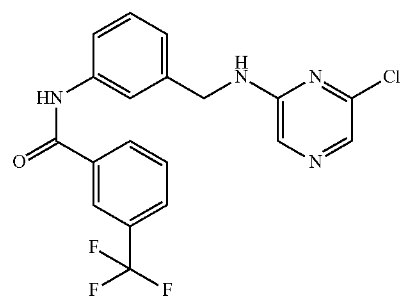 [SMILES: O=C(Nc1cccc(CNc2cncc(Cl)n2)c1)c1cccc(C(F)(F)F)c1] | δ 4.56 (d, J 5.7 Hz, 2H), 5.21 (t, J 5.7 Hz, 2H), 7.16 (d, J 7.5 Hz, 1H), 7.35 (t, J 7.8 Hz, 1H), 7.50-7.53 (m, 1H), 7.62 (t, J 7.8 Hz, 1H), 7.70 (brs, 1H), 7.75 (s, 1H), 7.80-7.84 (m, 2H), 7.96 (brs, 1H), 8.04 (d, J 8.1 Hz, 1H), 8.10 (s, 1H) | m/z (ESI) 407 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 164 | 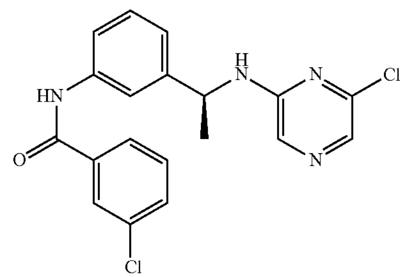 | δ 1.60 (d, J 6.6 Hz, 3H), 4.85-4.94 (m, 1H), 5.12 (d, J 6.3 Hz, 1H), 7.16 (d, J 8.1 Hz, 1H), 7.35 (t, J 8 Hz, 1H), 7.40 (t, J 7.5 Hz 1H), 7.48-7.55 (m, 2H), 7.63 (s, 1H), 7.70-7.75 (m, 2H), 7.79-7.81 (m, 2H), 7.83-7.85 (m, 1H) | m/z (ESI) 387 [M + H]⁺ | Example 1 |
| 165 | 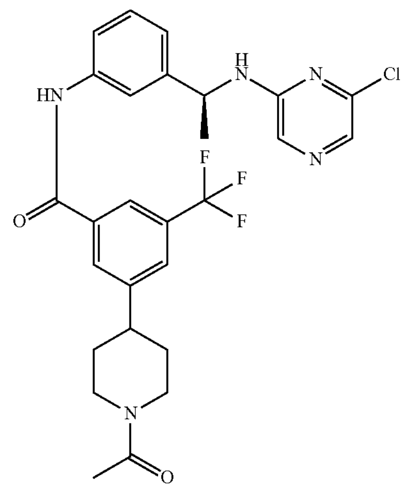 [SMILES: CC(=O)N1CCC(c2cc(C(=O)Nc3cccc([C@H](C)Nc4cncc(Cl)n4)c3)cc(C(F)(F)F)c2)CC1] | δ 1.59 (d, J 6.9 Hz, 3H), 1.66-1.71 (m, 2H), 1.82-1.98 (m, 2H), 2.13 (s, 3H), 2.56-2.65 (m, 1H), 2.83-2.94 (m, 1H), 3.14-3.23 (m, 1H), 3.94-3.98 (m, 1H), 4.72-4.77 (m, 1H), 4.85-4.95 (m, 1H), 5.20 (d, J 6.9 Hz, 1H) 7.17 (d, J 8.1 Hz, 1H), 7.36 (t, J 8 Hz, 1H), 7.56-7.63 (m, 3H), 7.73 (brs, 1H), 7.78 (brs, 1H), 7.92-7.96 (m, 2H), 8.33 (d, J 8.7 Hz, 1H) | m/z (ESI) 546 [M + H]⁺ | Example 1 |
| 166 | 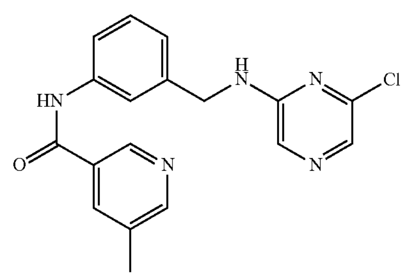 [SMILES: Cc1cncc(C(=O)Nc2cccc(CNc3cncc(Cl)n3)c2)c1] | δ 2.38 (s, 3H), 4.54 (d, J 5.7 Hz, 2H), 5.50 (brs, 1H), 7.14 (d, J 7.5 Hz, 1H), 7.32 (t, J 7.8 Hz, 1H), 7.48-7.51 (m, 1H), 7.68 (s, 1H), 7.74 (s, 1H), 7.78 (s, 1H), 7.96 (s, 1H), 8.28 (brs, 1H), 8.55 (s, 1H), 8.84 (s, 1H) | m/z (ESI) 354 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 167 | (structure: 6-chloropyrazin-2-yl NH-CH(CH₃)- attached to 2-methyl-5-aminophenyl) | δ 1.50 (d, J 6.6 Hz, 3H), 2.30 (s, 3H), 3.54 (brs, 2H), 4.88-4.96 (m, 1H), 5.02 (brd, J 5.7 Hz, 1H), 6.51 (dd, J 8.1, 2.4 Hz, 1H), 6.67 (d, J 2.4 Hz, 1H), 6.95 (d, J 8.1 Hz, 1H), 7.50 (s, 1H), 7.78 (s, 1H) | m/z (ESI) 263 [M + H]⁺ | Example 1, using starting compound: 2-methyl-5-nitrobenzoic acid. |
| 168 | (structure: 6-chloropyrazin-2-yl NH-CH(CH₃)- attached to 2-methyl-5-(3-methylbenzamido)phenyl) | δ 1.53 (d, J 6.3 Hz, 3H), 2.41 (s, 3H), 2.42 (s, 3H), 5.03-5.12 (m, 1H), 5.16 (brd, J 6.6 Hz, 1H), 7.16 (d, J 8.1 Hz, 1H), 7.33-7.35 (m, 2H), 7.42 (dd, J 8.1, 2.4 Hz, 1H), 7.56 (s, 1H), 7.59-7.63 (m, 1H), 7.66 (brs, 2H), 7.76 (s, 1H), 7.80 (brs, 1H) | m/z (ESI) 381 [M + H]⁺ | Example 1 |
| 169 | (structure: 6-chloropyrazin-2-yl NH-CH(CH₃)- attached to 2-methyl-5-(3-trifluoromethylbenzamido)phenyl) | δ 1.51 (d, J 6.9 Hz, 3H), 2.42 (s, 3H), 5.01-5.10 (m, 1H), 5.19 (d, J 6.3 Hz, 1H), 7.16 (d, J 8.1 Hz, 1H), 7.43 (dd, J 8.1, 2.4 Hz, 1H), 7.52-7.63 (m, 3H), 7.74 (s, 1H), 7.78 (d, J 7.5 Hz, 1H), 7.98-8.02 (m, 2H), 8.09 (s, 1H) | m/z (ESI) 435 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 170 | 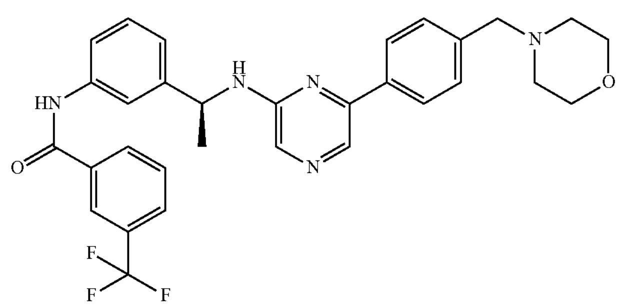 [SMILES: C[C@H](Nc1cncc(-c2ccc(CN3CCOCC3)cc2)n1)c1cccc(NC(=O)c2cccc(C(F)(F)F)c2)c1] | δ 1.64 (d, J 6.3 Hz, 3H), 2.44-2.47 (m, 4H), 3.53 (s, 2H), 3.69-372 (m, 4H), 5.02-5.04 (m, 2H), 7.23 (m, 1H), 7.38-7.41 (m, 2H), 7.52-7.55 (m, 2H), 7.64-7.66 (m, 1H), 7.73 (s, 1H), 7.75-777 (m, 1H), 7.80-7.83 (m, 2H), 7.84-7.87 (m, 2H), 8.04-8.07 (m, 1H), 8.12 (s, 1H), 8.27 (s, 1H) | m/z (ESI) 562 [M + H]⁺ | Example 27 |
| 171 | 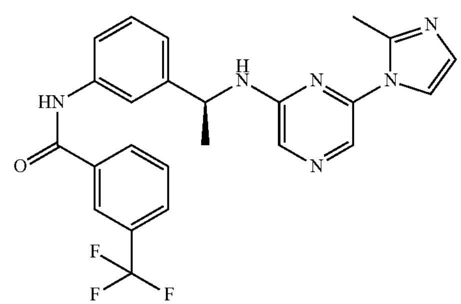 [SMILES: Cc1nccn1-c1cncc(N[C@@H](C)c2cccc(NC(=O)c3cccc(C(F)(F)F)c3)c2)n1] | δ 1.62 (d, J 6.9 Hz, 3H), 2.41 (s, 3H), 4.93-5.02 (m, 1H), 5.28 (d, J 6.6 Hz, 1H), 6.96 (d, J 1.5 Hz, 1H), 7.15-7.18 (m, 2H), 7.35 (t, J 7.8 Hz, 1H), 7.45-7.49 (m, 1H), 7.59-7.64 (m, 1H), 7.79-7.81 (m, 2H), 7.83 (s, 1H), 7.86 (s, 1H), 8.06 (d, J 7.8 Hz, 1H), 8.13 (brs, 1H), 8.17 (brs, 1H) | m/z (ESI) 467 [M + H]⁺ | Example 25 |
| 172 | 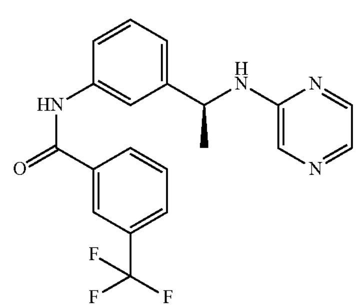 [SMILES: C[C@H](Nc1cnccn1)c1cccc(NC(=O)c2cccc(C(F)(F)F)c2)c1] | δ 1.60 (d, J 6.6 Hz, 3H), 4.91-5.02 (m, 2H), 7.17-7.20 (m, 1H), 7.35 (t, J 7.5 Hz, 1H), 7.52-7.56 (m, 1H), 7.63 (t, J 7.8 Hz, 1H), 7.68-7.69 (m, 1H), 7.78-7.82 (m, 3H), 7.88 (s, 1H), 7.95-7.97 (m, 1H), 8.04-8.06 (m, 1H), 8.12 (s, 1H) | m/z (ESI) 387 [M + H]⁺ | Example 2 (byproduct) |

TABLE 1-continued

| Compound Number | Structure | 1H nmr data (in CDCl3 unless otherwise stated) | Mass spectral data | Synthetic Method |
|---|---|---|---|---|
| 173 | (structure: pyrazine with 4-sulfamoylphenyl, NH-CH(CH3)-phenyl-NHC(O)-3-(trifluoromethyl)phenyl) | CD3OD δ 1.62 (d, J 6.9 Hz, 3H), 5.14 (q, J 6.6 Hz, 1H), 7.26-7.29 (m, 1H), 7.35 (t, J 7.8 Hz, 1H), 7.51-7.54 (m, 1H), 7.72 (t, J 7.8 Hz, 1H), 7.86-7.90 (m, 3H), 7.92 (d, J 8.7 Hz, 2H), 8.06 (d, J 8.7 Hz, 2H), 8.17-8.22 (m, 2H), 8.24 (brs, 1H) | m/z (ESI) 542 [M + H]+ | Example 2 |
| 174 | (structure: pyrazine with 4-hydroxymethylphenyl, NH-CH(CH3)-phenyl-NHC(O)-3-(trifluoromethyl)phenyl) | CD3OD δ 1.61 (d, J 6.9 Hz, 3H), 5.11-5.18 (m, 1H), 4.61 (s, 2H), 7.26-7.29 (m, 1H), 7.32-7.40 (m, 3H), 7.53-7.57 (m, 1H), 7.71 (t, J 7.8 Hz, 1H), 7.80 (brs, 1H), 7.86-7.89 (m, 4H), 8.11 (brs, 1H), 8.18 (d, J 7.5 Hz, 1H), 8.25 (brs, 1H) | m/z (ESI) 493 [M + H]+ | Example 28 |
| 175 | (structure: pyrazine with 3-hydroxyphenyl, NH-CH(CH3)-phenyl-NHC(O)-3-(trifluoromethyl)phenyl) | CD3OD δ 1.60 (d, J 6.6 Hz, 3H), 5.14-5.21 (m, 1H), 6.79-6.83 (m, 1H), 7.20 (t, J 7.7 Hz, 1H), 7.27-7.30 (m, 1H), 7.32-7.37 (m, 2H), 7.42-7.44 (m, 1H), 7.49-7.53 (m, 1H), 7.71 (t, J 7.8 Hz, 1H), 7.79 (brs, 1H), 7.86-7.90 (m, 2H), 8.06 (brs, 1H), 8.19 (d, J 7.8 Hz, 1H), 8.25 (brs, 1H) | m/z (ESI) 479 [M + H]+ | Example 28 |

TABLE 1-continued

| Compound Number | Structure | ¹H nmr data (in CDCl₃ unless otherwise stated) | Mass spectral data | Synthetic Method |
|---|---|---|---|---|
| 176 | 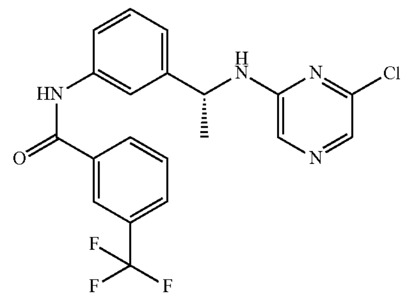 [SMILES: C[C@@H](Nc1cncc(Cl)n1)c1cccc(NC(=O)c2cccc(C(F)(F)F)c2)c1] | δ 1.69 (d, J 6.3 Hz, 3H), 6.16 (q, J 6.3 Hz, 1H), 7.24-7.27 (m, 1H), 7.38 (t, J 7.8 Hz, 1H), 7.59-7.65 (m, 2H), 7.74 (t, J 1.8 Hz, 1H), 7.81 (d, J 7.8 Hz, 1H), 7.96 (brs, 1H), 8.06 (d, J 7.8 Hz, 1H), 8.10 (s, 1H), 8.13 (s, 1H), 8.14 (s, 1H) | m/z (ESI) 422 [M + H]⁺ | Example 29 |
| 177 | 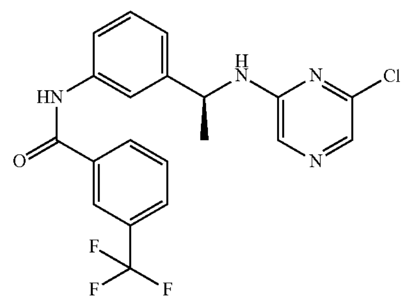 [SMILES: C[C@H](Nc1cncc(Cl)n1)c1cccc(NC(=O)c2cccc(C(F)(F)F)c2)c1] | δ 1.70 (d, J 6.3 Hz, 3H), 6.17 (q, J 6.3 Hz, 1H), 7.24-7.28 (m, 1H), 7.39 (t, J 7.8 Hz, 1H), 7.60-7.67 (m, 2H), 7.74 (t, J 1.8 Hz, 1H), 7.82 (d, J 7.8 Hz, 1H), 7.90 (brs, 1H), 8.07 (d, J 7.8 Hz, 1H), 8.11 (s, 1H), 8.13 (brs, 1H), 8.15 (s, 1H) | m/z (ESI) 422 [M + H]⁺ | Example 29 |
| 178 | 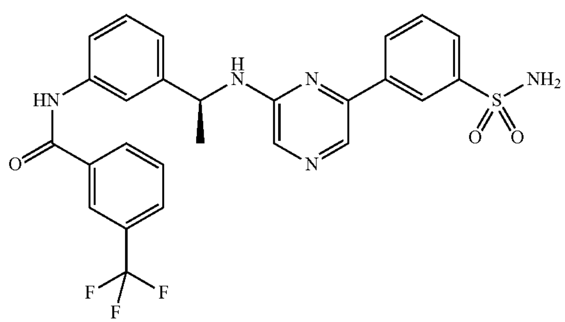 [SMILES: C[C@H](Nc1cncc(-c2cccc(S(N)(=O)=O)c2)n1)c1cccc(NC(=O)c2cccc(C(F)(F)F)c2)c1] | CD₃OD δ 1.61 (d, J 6.9 Hz, 3H), 5.17 (q, J 6.9 Hz, 1H), 7.29-7.38 (m, 2H), 7.55-7.62 (m, 2H), 7.72 (t, J 7.8 Hz, 1H), 7.83-7.93 (m, 4H), 8.10-8.14 (m, 1H), 8.20-8.26 (m, 3H), 8.55 (t, J 1.5 Hz, 1H) | m/z (ESI) 542 [M + H]⁺ | Example 2 |

TABLE 1-continued

| Compound Number | Structure | $^1$H nmr data (in CDCl$_3$ unless otherwise stated) | Mass spectral data | Synthetic Method |
|---|---|---|---|---|
| 179 | 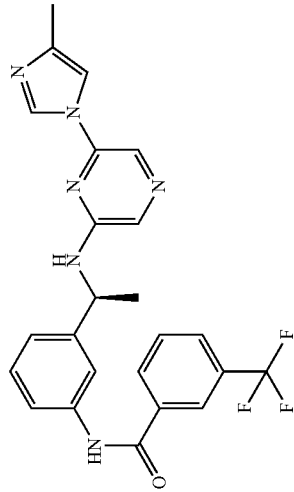 | δ 1.62 (d, J 6.9 Hz, 3H), 2.24 (s, 3H), 4.92-5.01 (m, 1H), 5.28 (d, J 6.0 Hz, 1H), 7.16-7.21 (m, 2H), 7.35 (t, J 7.7 Hz, 1H), 7.45-7.49 (m, 1H), 7.60 (t, J 7.8 Hz, 1H), 7.73 (s, 1H), 7.78 (s, 1H), 7.82 (brs, 1H), 7.85 (s, 1H), 8.04-8.07 (m, 2H), 8.13 (brs, 1H), 8.18 (brs, 1H) | m/z (ESI) 467 [M + H]$^+$ | Example 25 |
| 180 | 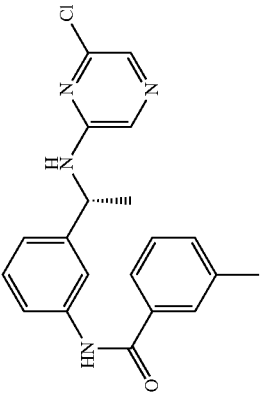 | δ 1.59 (d, J 6.3 Hz, 3H), 2.43 (s, 3H), 4.85-4.94 (m, 1H), 5.13 (d, J 6.6 Hz, 1H), 7.14 (brd, J 7.5 Hz, 1H), 7.31-7.38 (m, 3H), 7.49-7.52 (m, 1H), 7.61-7.68 (m, 3H), 7.73-7.74 (m, 1H), 7.79 (s, 1H), 7.83 (brs, 1H) | m/z (ESI) 367 [M + H]$^+$ | Example 1 |
| 181 | 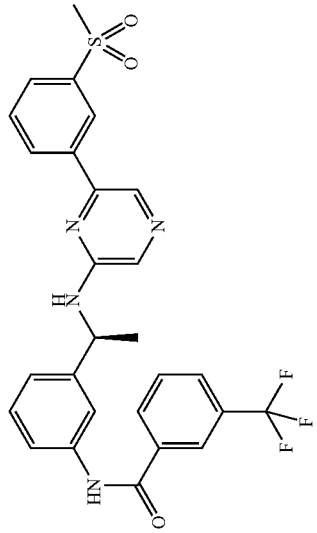 | δ 1.62 (d, J 6.9 Hz, 3H), 2.97 (s, 3H), 5.04-5.13 (m, 1H), 5.21 (d, J 6.0 Hz, 1H), 7.20 (brd, J 8.4 Hz, 1H), 7.36 (t, J 8.0 Hz, 1H), 7.55-7.56 (m, 1H), 7.58-7.68 (m, 2H), 7.80-7.96 (m, 4H), 8.10-8.13 (m, 1H), 8.19 (brd, J 7.8 Hz, 1H), 8.28 (s, 1H), 8.32 (s, 1H), 8.72-8.73 (m, 1H), 8.80 (brs, 1H) | m/z (ESI) 541 [M + H]$^+$ | Example 28 |

| Compound Number | Structure | ¹H nmr data (in CDCl₃ unless otherwise stated) | Mass spectral data | Synthetic Method |
|---|---|---|---|---|
| 182 | 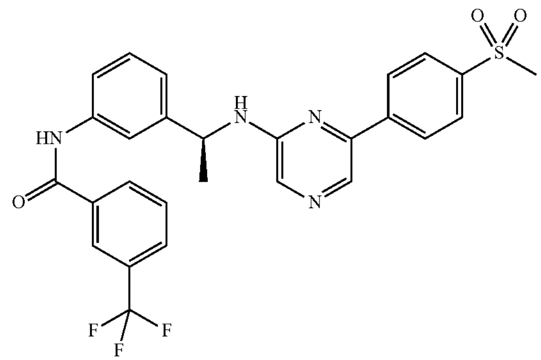 [SMILES: C[C@H](Nc1cncc(-c2ccc(S(C)(=O)=O)cc2)n1)c1cccc(NC(=O)c2cccc(C(F)(F)F)c2)c1] | δ 1.66 (d, J 6.9 Hz, 3H), 3.07 (s, 3H), 5.02-5.11 (m, 1H), 5.19 (d, J 6.0 Hz, 1H), 7.24 (brd, J 7.8 Hz, 1H), 7.38 (t, J 7.8 Hz, 1H), 7.46-7.49 (m, 1H), 7.64 (t, J 7.7 Hz, 1H), 7.80-7.83 (m, 1H), 7.87 (s, 2H), 7.93 (brs, 1H), 7.98 (d, J 8.4 Hz, 2H), 8.05-8.09 (m, 3H), 8.13 (brs, 1H), 8.31 (s, 1H) | m/z (ESI) 541 [M + H]⁺ | Example 28 |
| 183 | 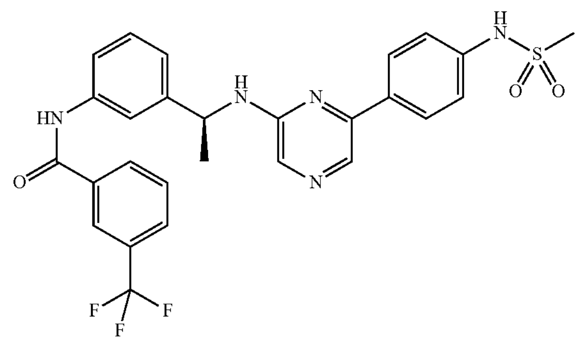 [SMILES: C[C@H](Nc1cncc(-c2ccc(NS(C)(=O)=O)cc2)n1)c1cccc(NC(=O)c2cccc(C(F)(F)F)c2)c1] | CD₃OD δ 1.60 (d, J 7.2 Hz, 3H), 2.96 (s, 3H), 5.13 (q, J 6.9 Hz, 1H), 7.25-7.30 (m, 3H), 7.34 (t, J 7.8 Hz, 1H), 7.51-7.55 (m, 1H), 7.71 (t, J 7.5 Hz, 1H), 7.79 (s, 1H), 7.86-7.90 (m, 4H), 8.08 (s, 1H), 8.19 (d, J 7.5 Hz, 1H), 8.25 (s, 1H) | m/z (ESI) 556 [M + H]⁺ | Example 2 |
| 184 | 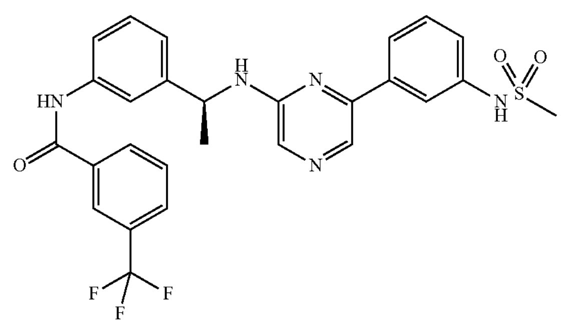 | δ 1.62 (d, J 6.9 Hz, 3H), 2.97 (s, 3H), 5.05 (d, J 6.9 Hz, 1H), 5.19-5.27 (m, 1H), 7.23 (brd, J 8.1 Hz, 1H), 7.29-7.31 (m, 1H), 7.34-7.41 (m, 3H), 7.63-7.71 (m, 2H), 7.81 (d, J 5.7 Hz, 1H), 7.86 (brs, 2H), 7.92 (m, 1H), 8.09 (s, 1H), 8.15-8.18 (m, 2H), 8.24 (d, J 7.8 Hz, 1H), 8.28 (s, 1H) | m/z (ESI) 556 [M + H]⁺ | Example 2 |

TABLE 1-continued

| Compound Number | Structure | ¹H nmr data (in CDCl₃ unless otherwise stated) | Mass spectral data | Synthetic Method |
|---|---|---|---|---|
| 185 | 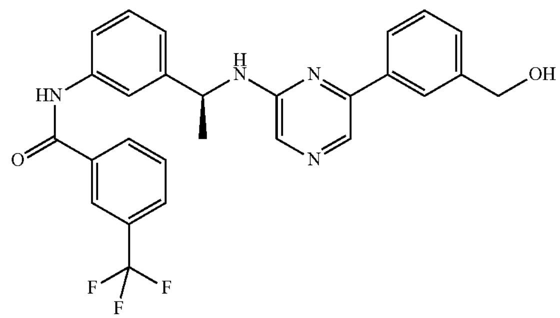 [SMILES: C[C@H](Nc1cncc(-c2cccc(CO)c2)n1)c1cccc(NC(=O)c2cccc(C(F)(F)F)c2)c1] | δ 1.55 (d, J 6.9 Hz, 3H), 4.69 (ABq, J 12.9 Hz, 2H), 4.90-4.99 (m, 1H), 5.14 (d, J 6.0 Hz, 1H), 7.17 (d, J 7.8 Hz, 1H), 7.25-7.30 (m, 2H), 7.35 (t, J 7.8 Hz, 1H), 7.54-7.78 (m, 6H), 7.97 (s, 1H), 8.06 (d, J 7.8 Hz, 1H), 8.16 (s, 2H), 8.65 (s, 1H) | m/z (ESI) 493 [M + H]⁺ | Example 28 |
| 186 | 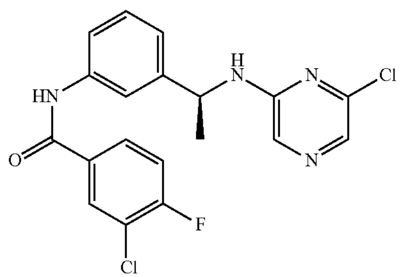 [SMILES: C[C@H](Nc1cncc(Cl)n1)c1cccc(NC(=O)c2ccc(F)c(Cl)c2)c1] | δ 1.59 (d, J 6.9 Hz, 3H), 4.85-4.94 (m, 1H), 5.10 (d, J 6.6 Hz, 1H), 7.16-7.18 (m, 1H), 7.23-7.28 (m, 1H), 7.33-7.38 (m, 1H), 7.47-7.51 (m, 1H), 7.63 (s, 1H), 7.67-7.68 (m, 1H), 7.73-7.78 (m, 2H), 7.80 (s, 1H), 7.94 (dd, J 6.9, 2.4 Hz, 1H) | m/z (ESI) 405 [M + H]⁺ | Example 1 |
| 187 | 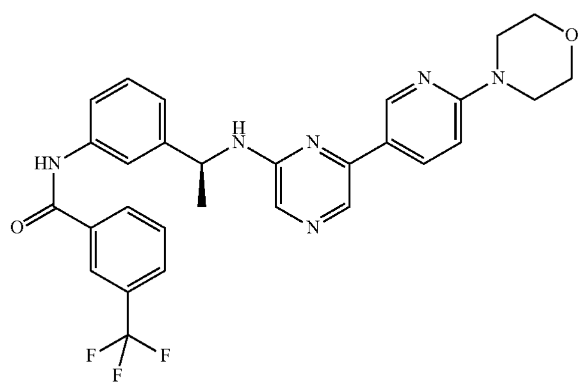 [SMILES: C[C@H](Nc1cncc(-c2ccc(N3CCOCC3)nc2)n1)c1cccc(NC(=O)c2cccc(C(F)(F)F)c2)c1] | δ 1.63 (d, J 6.3 Hz, 3H), 3.57 (t, J 4.8 Hz, 4H), 3.82 (t, J 4.8 Hz, 4H), 5.01-5.08 (m, 2H), 6.67 (d, J 9.3 Hz, 1H), 7.24 (dt, J 7.8, 1.5 Hz, 1H), 7.37 (t, J 7.8 Hz, 1H), 7.52-7.55 (m, 1H), 7.63 (t, J 7.8 Hz, 1H), 7.69 (s, 1H), 7.75 (t, J 1.8 Hz, 1H), 7.82 (d, J 7.8 Hz, 1H), 7.93 (brs, 1H), 8.02-8.09 (m, 2H), 8.14 (brs, 1H), 8.19 (s, 1H), 8.76 (d, J 3.3 Hz, 1H) | m/z (ESI) 549 [M + H]⁺ | Example 28 |

TABLE 1-continued

| Compound Number | Structure | ¹H nmr data (in CDCl₃ unless otherwise stated) | Mass spectral data | Synthetic Method |
|---|---|---|---|---|
| 188 | 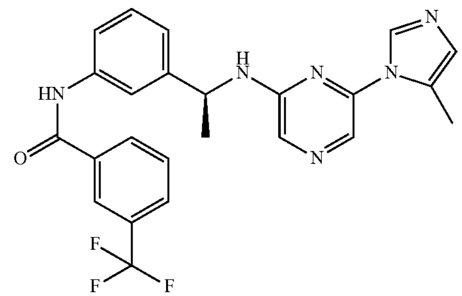 [SMILES: Cc1cncn1-c1cncc(N[C@@H](C)c2cccc(NC(=O)c3cccc(C(F)(F)F)c3)c2)n1] | δ 1.62 (d, J 6.9 Hz, 3H), 2.23 (s, 3H), 4.92-5.00 (m, 1H), 5.29 (d, J 6.0 Hz, 1H), 7.19 (d, J 7.8 Hz, 1H), 7.35 (t, J 7.8 Hz, 1H), 7.48 (d, J 7.8 Hz, 1H), 7.60 (brs, 1H), 7.77-7.84 (m, 5H), 8.07-8.31 (m, 4H) | m/z (ESI) 467 [M + H]⁺ | Example 25 |
| 189 | 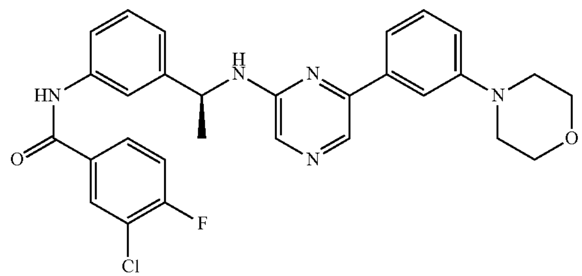 [SMILES: C[C@H](Nc1cncc(-c2cccc(N3CCOCC3)c2)n1)c1cccc(NC(=O)c2ccc(F)c(Cl)c2)c1] | δ 1.59 (d, J 6.9 Hz, 3H), 3.16-3.19 (m, 4H), 3.85-3.89 (m, 4H), 4.93-5.01 (m, 1H), 5.17 (d, J 6.0 Hz, 1H), 6.93-6.97 (m, 1H), 7.18 (t, J 8.4 Hz, 2H), 7.27-7.32 (m, 2H), 7.34-7.35 (m, 1H), 7.43-7.44 (m, 1H), 7.48-7.51 (m, 1H), 7.68-7.75 (m, 3H), 7.92 (dd, J 6.8, 2.3 Hz, 1H), 8.08 (s, 1H), 8.22 (s, 1H) | m/z (ESI) 532 [M + H]⁺ | Example 28 |
| 190 | 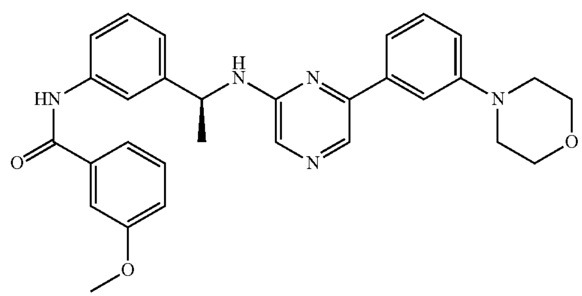 [SMILES: COc1cccc(C(=O)Nc2cccc([C@H](C)Nc3cncc(-c4cccc(N5CCOCC5)c4)n3)c2)c1] | δ 1.62 (d, J 7.2 Hz, 3H), 3.17-3.21 (m, 4H), 3.85 (s, 3H), 3.86-3.89 (m, 4H), 4.94-5.03 (m, 1H), 5.09 (d, J 6.0 Hz, 1H), 6.93-6.97 (m, 1H), 7.04-7.10 (m, 1H), 7.18-7.21 (m, 1H), 7.30-7.37 (m, 5H), 7.39-7.51 (m, 3H), 7.73 (s, 1H), 7.76-7.77 (m, 1H), 7.87 (s, 1H), 8.25 (s, 1H) | m/z (ESI) 510 [M + H]⁺ | Example 28 |

TABLE 1-continued

| Compound Number | Structure | ¹H nmr data (in CDCl₃ unless otherwise stated) | Mass spectral data | Synthetic Method |
|---|---|---|---|---|
| 191 | 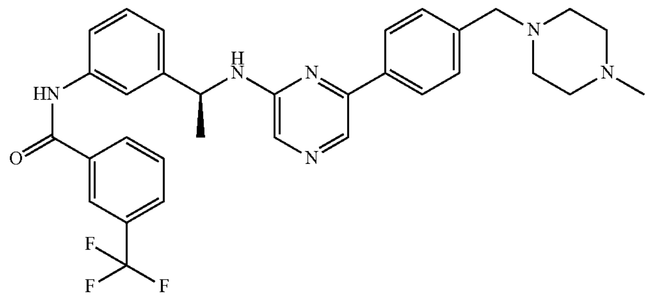 [SMILES: C[C@H](Nc1cncc(-c2ccc(CN3CCN(C)CC3)cc2)n1)c1cccc(NC(=O)c2cccc(C(F)(F)F)c2)c1] | δ 1.63 (d, J 6.6 Hz, 3H), 2.30 (s, 3H), 2.48 (brs, 8H), 3.54 (s, 2H), 4.98-5.08 (m, 2H), 7.24 (d, J 7.2 Hz, 1H), 7.34-7.40 (m, 3H), 7.53-7.56 (m, 1H), 7.62 (t, J 7.8 Hz, 1H), 7.72 (s, 1H), 7.75 (s, 1H), 7.79-7.86 (m, 3H), 7.96 (brs, 1H), 8.06 (d, J 8.4 Hz, 1H), 8.13 (s, 1H), 8.26 (s, 1H) | m/z (ESI) 575 [M + H]⁺ | Example 27 |
| 192 | 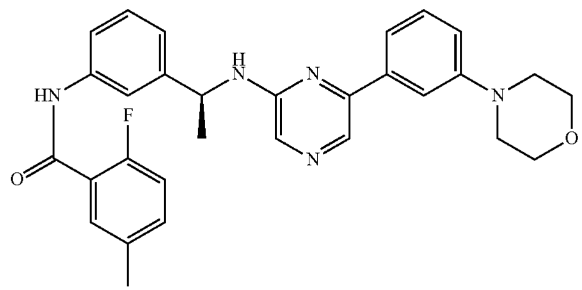 [SMILES: Cc1ccc(F)c(C(=O)Nc2cccc([C@H](C)Nc3cncc(-c4cccc(N5CCOCC5)c4)n3)c2)c1] | δ 1.64 (d, J 6.9 Hz, 3H), 2.38 (s, 3H), 3.18-3.22 (m, 4H), 3.86-3.90 (m, 4H), 4.96-5.05 (m, 1H), 5.07-5.09 (m, 1H), 6.93-6.97 (m, 1H), 7.02-7.09 (m, 1H), 7.21 (d, J 7.5 Hz, 1H), 7.27-7.40 (m, 4H), 7.46-7.52 (m, 2H), 7.75 (s, 1H), 7.80 (brs, 1H), 7.93-7.96 (m, 1H), 8.25 (s, 1H), 8.42-8.48 (m, 1H) | m/z (ESI) 512 [M + H]⁺ | Example 28 |
| 193 | 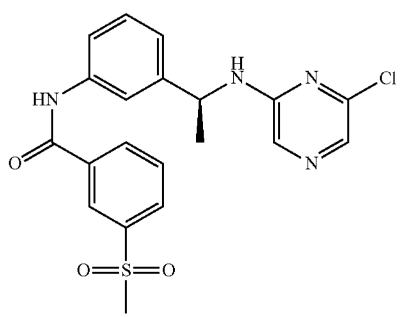 [SMILES: C[C@H](Nc1cncc(Cl)n1)c1cccc(NC(=O)c2cccc(S(C)(=O)=O)c2)c1] | δ 1.58 (d, J 6.3 Hz, 3H), 3.10 (s, 1H), 4.87-4.96 (m, 1H), 5.27-5.32 (m, 1H), 7.17 (d, J 7.5 Hz, 1H), 7.35 (t, J 8.4 Hz, 1H), 7.61 (d, J 8.1 Hz, 1H), 7.65 (s, 1H), 7.67-7.72 (m, 2H), 7.76 (brs, 1H), 8.09 (b, J 7.8 Hz, 1H), 8.21 (d, J 7.8 Hz, 1H), 8.33 (brs, 1H), 8.42 (brs, 1H) | m/z (ESI) 431 [M + H]⁺ | Example 1 |

TABLE 1-continued

| Compound Number | Structure | ¹H nmr data (in CDCl₃ unless otherwise stated) | Mass spectral data | Synthetic Method |
|---|---|---|---|---|
| 194 | 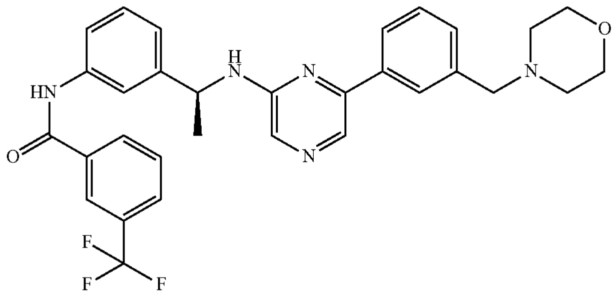 [SMILES: C[C@H](Nc1cncc(-c2cccc(CN3CCOCC3)c2)n1)c1cccc(NC(=O)c2cccc(C(F)(F)F)c2)c1] | δ 1.62 (d, J 6.9 Hz, 3H), 2.45 (t, J 3.5 Hz, 4H), 3.55 (s, 2H), 3.70 (t, J 3.5 Hz, 4H), 4.96-5.05 (m, 1H), 5.12 (d, J 6.3 Hz, 1H), 7.24 (d, J 7.8 Hz, 1H), 7.33-7.39 (m, 3H), 7.52-7.55 (m, 1H), 7.60 (t, J 7.8 Hz, 1H), 7.72 (s, 1H), 7.76-7.80 (m, 3H), 7.84 (s, 1H), 8.03-8.07 (m, 2H), 8.12 (s, 1H), 8.26 (s, 1H) | m/z (ESI) 562 [M + H]⁺ | Example 27 |

The terms "$C_{1-6}$alkyl" and "$C_{1-4}$alkyl" refer to straight chain or branched chain hydrocarbon groups having from 1 to 6 or 1 to 4 carbon atoms. Examples include ethyl, propyl, isopropyl, butyl, isobutyl, sec-butyl, tert-butyl, pentyl, neopentyl and hexyl.

The terms "$C_{1-6}$alkylene" and "$C_{1-4}$alkylene" refer to the divalent equivalent of "$C_{1-6}$alkyl" and "$C_{1-4}$alkyl" defined above.

The term "$C_{3-8}$cycloalkyl" refers to non-aromatic cyclic hydrocarbon groups having from 3 to 8 carbon atoms. Examples include cyclopropyl, cyclobutyl, cyclopentyl and cyclohexyl.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl. 5- or 6-membered aryls such as phenyl are preferred.

The term "heterocyclyl" refers to saturated or unsaturated, monocyclic or polycyclic hydrocarbon groups containing at least one heteroatom atom selected from the group consisting of N, O, S and $SO_2$.

Suitable heterocyclyls include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyridinyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidinyl or piperazinyl;

unsaturated condensed heterocyclic groups containing 1 to 5 nitrogen atoms, such as indolyl, isoindolyl, indolizinyl, pyrrolinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furanyl;

unsaturated 3 to 6-membered heteromonocyclic group containing 1 to 2 sulfur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl, benzoxadiazolyl or benzodioxolyl;

unsaturated 3 to 6-membered heteromonocyclic group containing 1 to 2 sulfur atoms and 1 to 3 nitrogen atoms, such as, thiazolyl or thiadiazolyl;

saturated 3 to 6-membered heteromonocyclic group containing 1 to 2 sulfur atoms and 1 to 3 nitrogen atoms, such as, thiomopholino or thiazolidinyl; and saturated 3 to 6-membered heteromonocyclic group containing 1 to 2 sulfur atoms, 1 to 3 nitrogen atoms and 1 to 2 oxygen atoms such as thiomorpholino-1-oxide and thiomorpholino-1,1-dioxide;

unsaturated condensed heterocyclic group containing 1 to 2 sulfur atoms and 1 to 3 nitrogen atoms, such as, benzothiazolyl or benzothiadiazolyl.

Preferred heterocyclyls are pyridinyl, pyrazinyl, piperidinyl, furanyl, pyrazolyl, indolyl, benzimidazolyl, 1,3-benzodioxolyl, piperazinyl, morpholinyl, thiophenyl or imidazolyl.

The term "halogen" refers to fluorine, chlorine, bromine and iodine, preferably fluorine.

The term "substituted or substituted" refers to a group that may or may not be further substituted with one or more groups selected from $C_{1-6}$ alkyl, $Si(C_{1-6}alkyl)_3$, $C_{3-6}$ cycloalkyl, $C_{2-6}$ alkenyl, $C_{2-6}$ alkynyl, aryl, heterocycylyl, halo, halo$C_{1-6}$alkyl, halo$C_{3-6}$cycloalkyl, halo$C_{2-6}$alkenyl, halo$C_{2-6}$alkynyl, haloaryl, haloheterocycylyl, hydroxy, $C_1$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{1-6}$alkenylacyl, $C_{2-6}$alkynylacyl, arylacyl, heterocycylylacyl, acylamino, acyloxy, aldehydo, $C_{1-6}$alkylsulfonyl, arylsulfonyl, $C_{1-6}$alkylsulfonylamino, arylsulphonylamino, $C_{1-6}$alkylsulfonyloxy, arylsulfonyloxy, $C_{1-6}$alkylsulfenyl, $C_{2-6}$alklysulfenyl, arylsulfenyl, carboalkoxy, carboaryloxy, mercapto, $C_{1-6}$alkylthio, arylthio, acylthio, cyano and the like. Preferred optional substituents are selected from the group consisting of $C_{1-4}$ alkyl, nitro, $C_{3-6}$ cycloalkyl, $C_{2-6}$ alkenyl, $C_{2-6}$ alkynyl, aryl, heterocycylyl, halo, hydroxy, $C_{1-4}$ alkoxy, aryloxy, carboxy, amino, arylacyl, heterocycylylacyl, acylamino, acyloxy, $OP(O)(OH)_2$, arylsulfonyl and cyano.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer. The compound may also exist as tautomers.

This invention also encompasses prodrugs of the compounds of formula I. For example, compounds of formula I having free amino, amido, hydroxy or carboxylic acid groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of the appropriate nitrogen and sulfur atoms in formula I.

This invention also encompasses methods of treating or preventing disorders that can be treated or prevented by the inhibition of protein kinases such as diseases associated with members of the class III PTK receptor family such as FMS (CFS-1R), c-KIT, PDGFRα or FLT3 and KDR, SRC, EphA2, EphA3, EphA8, FLT1, FLT4, HCK, LCK, PTK5, RET, SYK, DDR1 or DDR2 comprising administering drugs or prodrugs of compounds of the invention.

Process of Making Compounds

Compounds of the general formula I are generally prepared starting from a dihaloheterocycle.

The first step is a nucleophilic aromatic substitution to generate a monoamino-monohalo intermediate.

The nucleophilic aromatic substitution is typically carried out by addition of a primary or secondary amine to the dihalogenated heterocycle in a solvent such as ethanol, isopropanol, tert-butanol, dioxane, THF, DMF, ethoxyethanol, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include Pd(OAc)$_2$/P(t-Bu)$_3$, Pd$_2$(dba)$_3$/BINAP and Pd(OAc)$_2$/BINAP. These reactions are typically carried out in solvents such as toluene or dioxane, in the presence of bases such as caesium carbonate or sodium or potassium tert-butoxide at temperatures ranging from room temperature to reflux (e.g. Hartwig, J. F., *Angew. Chem. Int. Ed.* 1998, 37, 2046).

The amines employed in the first step of the synthesis of these compounds are obtained commercially or are prepared using methods well known to those skilled in the art. Of particular interest are α-alkylbenzylamines which may be prepared through reduction of oximes. Typical reductants include lithium aluminium hydride, hydrogen gas in the presence of palladium on charcoal catalyst, Zn in the presence of hydrochloric acid, sodium borohydride in the presence of a Lewis acid such as TiCl$_3$, ZrCl$_4$, NiCl$_2$ and MoO$_3$, or sodium borohydride in conjunction with Amberlyst H15 ion exchange resin and LiCl.

α-Alkylbenzylamines may also be prepared by reductive amination of the corresponding ketones. A classical method for such a transformation is the Leuckart-Wallach reaction, though catalytic conditions (HCO$_2$NH$_4$, [(CH$_3$)$_5$C$_5$RhCl$_2$]$_2$) or alternative procedures (e.g. NH$_4$OAc, Na(CN)BH$_3$) can also be used.

α-Alkylbenzylamines may also be prepared from the corresponding α-alkylbenzyl alcohols. Such methods include derivatisation of the hydroxyl as a mesylate or tosylate and displacement with a nitrogen nucleophile, such as phthalimide or azide which is converted to the primary amine using conventional synthetic methods; or, displacement of the hydroxyl with a suitable nitrogen nucleophile under Mitsunobu-like conditions. α-Alkylbenzyl alcohols can be prepared by reduction of the corresponding ketones with a reducing agent such as sodium borohydride in a solvent such as methanol. Alternatively, α-alkylbenzyl alcohols can be obtained through addition of an alkyl metal species (such as a Grignard reagent) to a benzaldehyde derivative, typically performed at room temperature or below in solvents such as tetrahydrofuran.

α-Alkyl benzylamines of high optical purity may be prepared from chiral α-alkyl benzyl alcohols using the methods outlined above. The chiral α-alkyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The monoamino-monohalo intermediate formed from the dihaloheterocycle and the amine described above, may then be further functionalised. For example, where the amine substituent bears an additional functional group, this functional group may be derivatised or functionalised using methods well-known to those skilled in the art. For example, a free primary amino group could be further functionalised to an amide, sulphonamide or urea functionality, or could be alkylated to generate a secondary or tertiary amine derivative. Preferable methods for the formation of an amide include coupling the amine with a carboxylic acid using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane, tetrahydrofuran or 1,4-dioxane. Alternatively, the acid component may be activated by conversion to an acid chloride (using thionyl chloride, oxalyl chloride, bis(trichloromethyl)carbonate or cyanuric chloride) or to mixed anhydride species (using, for example, t-butyl chloroformate or isopropyl chloroformate) or to active ester intermediates (such as N-hydroxysuccinimidyl, pentafluorophenyl or p-nitrophenyl esters) prior to reaction with the amine.

The monoamino-monochloro intermediate may then be reacted in a palladium mediated cross-coupling reaction with a suitably functionalised coupling partner to replace the halogen atom with an alternative moiety. Typical coupling partners are organoboronic acids or esters (Suzuki coupling: see for example Miyaura, N. and Suzuki, *Chem. Rev.* 1995, 95 2457), organostannanes (Stille coupling: see for example Stille, J. K., *Angew. Chem., Int. Ed. Engl.*, 1986, 25, 508), Grignard reagents (Kumada coupling: Kumada, M.; Tamao, K.; Sumitani, K. *Org. Synth.* 1988, Coll. Vol. 6, 407.) or organozinc species (Negishi coupling: Negishi, E.; *J. Organomet. Chem.* 2002, 653, 34).

The Suzuki coupling is the preferred coupling method and is typically performed in a solvent such as DME, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from Pd(PPh$_3$)$_4$, Pd(OAc)$_2$, [PdCl$_2$(dppf)], Pd$_2$(dba)$_3$/P(t-Bu)$_3$.

The monoamino-monochloro intermediate may also be subjected to a second nucleophilic aromatic substitution reaction using similar conditions to those outlined above.

Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, 1999). The products formed from the reaction sequences described above may be further derivatised using techniques well known to those skilled in the art.

The leaving group may be any suitable known type such as those disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen, more preferably chlorine.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly in the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, poly-vinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided.

In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorohexidine and thickening agents such as hypromellose may also be included.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents. Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) rectally or intravaginally, e.g. as a pessary, cream or foam.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: endothelin receptor antagonists (eg ambrisentan, bosentan, sitaxsentan), PDE-V inhibitors (eg sildenafil, tadalafil, vardenafil), Calcium channel blockers (eg amlodipine, felodipine, varepamil, diltiazem, menthol), prostacyclin, treprostinil, iloprost, beraprost, nitric oxide, oxygen, heparin, warfarin, diuretics, digoxin, cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD401g and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABA's such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

Methods of Treatment

The compounds of formula I may be used in the treatment of kinase associated diseases including diseases associated with members of the class III PTK receptor family such as FMS (CSF-1R), c-KIT, PDGFRβ, PDGRα or FLT3 and KDR, SRC, EphA2, EphA3, EphA8, FLT1, FLT4, HCK, LCK, PTK5, RET, SYK, DDR1 or DDR2 such as immunological and inflammatory diseases; hyperproliferative diseases including cancer and diseases involving neo-angiogenesis; renal and kidney diseases; bone remodeling diseases; metabolic diseases; and vascular diseases.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The term "kinase associated diseases" refers to a disorder or disorders that directly or indirectly result from or are aggravated by aberrant kinase activity, in particular activity associated with members of the class III PTK receptor family such as FMS (CSF-1R), c-KIT, PDGFRβ, PDGRα and FLT3, KDR, SRC, EphA2, EphA3, EphA8, FLT1, FLT4, HCK, LCK, PTK5 (FRK) or RET and/or which are alleviated by inhibition of one or more of these kinase enzymes.

In a preferred embodiment the kinase associated disease state involves diseases such as immunological and inflammatory diseases; hyperproliferative diseases including cancer and diseases involving neo-angiogenesis; renal and kidney diseases; bone remodeling diseases; metabolic diseases; and vascular diseases.

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease, cystic fibrosis, inflammatory bowel disease, irritable bowl syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Lou Gehrig's disease, Paget's disease, sepsis, conjunctivitis, neranl catarrh, chronic arthrorheumatism, systemic inflammatory response syndrome (SIRS), polymyositis, dermatomyositis (DM), Polaritis nodoa (PN), mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and diseases involving neo- and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfrorna (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphomaj; çji: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myeloproliferative diseases such as polycythemia rubra vera, primary myelofibrosis, thrombocythemia, essential thrombocythemia (ET), agnoneic myeloid metaplasia (AMM), also referred to as idiopathic myelofibrosis (IMF), and chronic myelogenous leukemia (CML).

The term "renal and kidney diseases" refers to diseases affecting the kidney and renal system, including but not limited to transplant allograft rejection, and acute and chronic kidney disease including glomerulonephritis and uremia.

The term "bone remodeling diseases" refers to diseases which involve bone cells including osteoclasts which diseases include but are but not limited to osteoporosis, Paget's disease of the bone, osteogenesis imperfecta, bone spurs, bone tumor craniosynostosis, enchondroma, fibrous displasia, giant cell tumour of the bone, infectious arthritis, Klippel-Feil syndrome, osteitis condensans, osteoichondritis dissecans, osteochondroma, osetomyelitis, and osteomalacia.

The term "metabolic disease" refers to diseases which are caused by an abnormal metabolic process including but not limited to atherosclerosis, metabolic syndrome, obesity, hepatic steatosis, high cholesterol, high plasma lipids, insulin resistance, type 2 diabetes, hypoglycemia, diabetic ketoacidosis, nonketotic hyperosmolar syndrome, acid-base imbalance, metabolic acidosis, metabolic alkalosis, amyloidosis, calcium metabolism disorders, iron metabolism disorders, malabsorption disorders, phosphorus metabolism disorders, porphyries, metabolic skin diseases, wasting syndrome, water-electrolyte imbalance, lipid metabolism disorders, metabolic syndrome X, mitochondrial diseases, glucose metabolism disorders, and DNA repair-deficiency disorders.

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

In one preferred embodiment, the present invention is directed to the control of macrophage populations.

In another preferred embodiment, the disease state is selected from the group consisting of Mastocytosis/Mast Cell Leukemia, Gastrointestinal Stromal Tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma.

In yet another preferred embodiment, the disease state is selected from the group consisting of restenosis, including coronary restenosis after angioplasty, atherectomy, or other invasive methods of plaque removal, and renal or peripheral artery restenosis after the same procedures; vascular proliferative phenomena and fibrosis associated with other forms of acute injury such as: pulmonary fibrosis associated with adult respiratory distress syndrome, renal fibrosis associated with nephritis, coronary stenosis associated with Kawasake's disease, and vascular narrowings associated with other arteritides such as Takayasha's disease; prevention of narrowings in vein grafts; prevention of narrowings due to accelerated smooth muscle cell migration and proliferation in transplanted organs; other fibrotic processes, such as scleroderma, myofibrosis, and; inhibition of tumor cell proliferation that is mediated by PDGF.

In a particularly preferred embodiment the disease state is selected from the group consisting of breast, pancreatic, lung, ovarian, oesophageal, colonic, thyroid and gastrointestinal tumours, head and neck cancer, gastric cancer, neuroblastoma, melanoma, mesothelioma, metastases both in bone and visceral organs, acute myelogenous leukaemia (AML) and chronic myelogenous leukemia (CML), transplant allograft rejection, fibrosis of the liver and kidney, arthrosclerosis, osteoporosis, rheumatoid arthritis (RA), atopic dermatitis, asthma, Crohn's disease, psoriasis, inflammatory bowel disease (IBD), multiple sclerosis, Alzheimer's Disease, Hodgkin's Disease, pulmonary adenoma, non small cell carcinoma, interstitial cystitis (IC) and Type I diabetes.

Dosages

The term "therapeutically effective amount" refers to the amount of the compound of formula I that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

DESCRIPTION OF THE FIGURES

In the examples, reference will be made to the accompanying figures in which.

EXAMPLES

Figure 1:
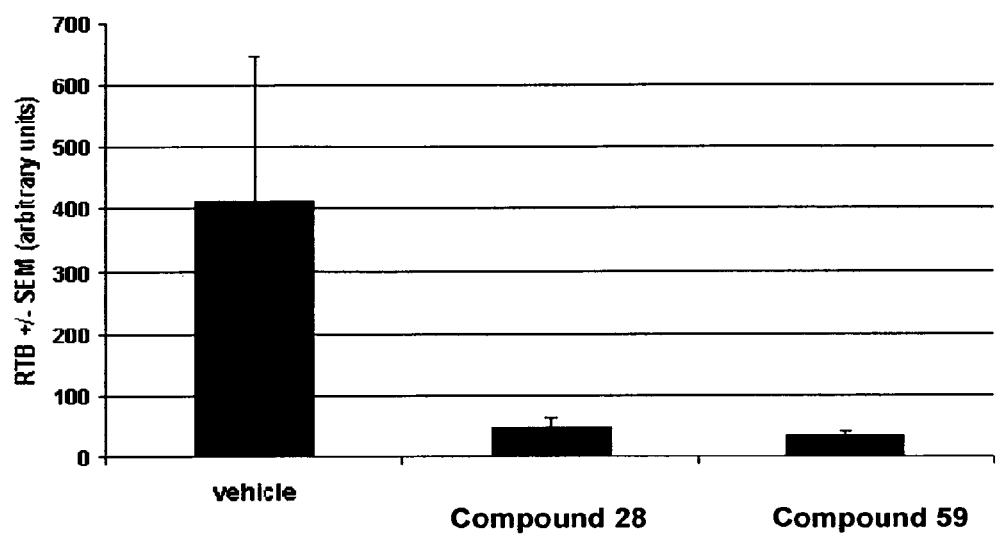
FIG. 1 is a graph showing the tumour burden in liver (relative to Vimentin) in tumour bearing mice treated with Compounds 28 and 59 compared with that of Vehicle as described in Example 33.

In order to exemplify the nature of the present invention such that it may be more clearly understood, the following non-limiting examples are provided.

Example 1

To a solution of (1S,2R)-(−)-cis-1-amino-2-indanol (1.49 g, 10 mmol) in tetrahydrofuran (100 mL), cooled to 0° C., was added borane-N,N-diethylaniline complex (17.8 mL, 100 mmol) and the mixture was stirred at 0° C. for 1 hour. After this time a solution of 3'-nitroacetophenone (16.5 g, 100 mL) in tetrahydrofuran (300 mL) was added dropwise over 4 hours and the mixture was allowed to warm to room temperature over night with stirring. After this time the mixture was quenched by stirring with acetone (40 mL) for 1 hour after which it was concentrated under reduced pressure. The yellow residue was dissolved in toluene (250 mL) and washed sequentially with dilute aqueous sulfuric acid (1M, 4×100 mL), water (100 mL), saturated aqueous sodium hydrogen carbonate (100 mL), water (100 mL) and brine (100 mL). The organic solution was dried over $MgSO_4$ and concentrated under reduced pressure to give (1R)-1-(3-nitrophenyl)ethanol (14.3 g, 86%).

To a solution of (1R)-1-(3-nitrophenyl)ethanol (12 g, 72 mmol) in tetrahydrofuran (220 mL), cooled to 0° C., was added diphenylphosphoryl azide (31 mL, 145 mmol) in one portion followed by 1,8-diazabicyclo[5.4.0]undec-7-ene (22 mL, 145 mmol) dropwise over 30 minutes. The reaction mixture was allowed to warm slowly to room temperature and was stirred for 38 hours after which time the mixture was diluted with ethyl acetate (100 mL) and water (100 mL), the two phases separated and the aqueous phase extracted with ethyl acetate (2×100 mL). The combined organic phases were washed with brine (100 mL), dried ($MgSO_4$) and concentrated under reduced pressure to give a black liquid. The crude liquid was purified by flash chromatography (silica, ethyl acetate/hexanes) to give 1-[(1S)-1-azidoethyl]-3-nitrobenzene (18 g) as a yellow liquid in acceptable purity.

To a solution of 1-[(1S)-1-azidoethyl]-3-nitrobenzene (16.5 g, 86 mmol) in a mixture of toluene (325 mL) and water (40 mL) was added triphenylphosphine (44.5 g, 170 mmol) in one portion. The mixture was immediately heated to 80° C. where it was stirred for 3 hours. After this time the mixture was allowed to cool to room temperature, was diluted with ethyl acetate (100 mL), the two phases separated and the organic phase extracted with dilute aqueous hydrochloric acid (2M, 3×100 mL). The acidic extracts were basified to pH>10 with solid potassium hydroxide and were then extracted with dichloromethane (3×100 mL). The organic extracts were washed with brine (100 mL), dried ($MgSO_4$) and concentrated under reduced pressure to give (1S)-1-(3-nitrophenyl)ethanamine (13.1 g, 92%) as a yellow liquid.

A mixture of (1S)-1-(3-nitrophenyl)ethanamine (13.1 g, 79.4 mmol) and 10% palladium on carbon (0.75 g) in methanol (250 mL) was stirred vigorously under an atmoshphere of hydrogen for 19 hours. After this time the mixture was filtered through a pad of Celite and the pad was washed with methanol (800 mL). The combined filtrates were concentrated under reduced pressure to give 3-[(1S)-1-aminoethyl]aniline as a brown solid (10.8 g, 100%).

A mixture of 3-[(1S)-1-aminoethyl]aniline (7.5 g, 55 mmol), 2,6-dichloropyrazine (12.3 g, 82.5 mmol) and potassium carbonate (15.2 g, 110 mmol) in dioxane (140 mL) was heated at reflux for 3 days. After this time the mixture was cooled to room temperature, filtered and concentrated under reduced pressure to give an orange oil which was purified by flash chromatography (silica, ethyl acetate/hexanes) to give N-[(1S)-1-(3-aminophenyl)ethyl]-6-chloropyrazin-2-amine (11.6 g, 85%) as a beige solid.

A mixture of N-[(1S)-1-(3-aminophenyl)ethyl]-6-chloropyrazin-2-amine (300 mg, 1.2 mmol), 6-methylnicotinic acid (182 mg, 1.32 mmol), N-(3-dimethylaminopropyl)-N'-ethylcarbodiimide hydrochloride (277 mg, 1.45 mmol), 4-pyrrolidinopyridine (36 mg, 0.24 mmol) and triethylamine (0.34 mL, 2.4 mmol) in dichloromethane (6 mL) was stirred at room temperature for 72 hours. After this time the mixture was diluted with ethyl acetate (20 mL), washed successively with saturated aqueous sodium hydrogen carbonate (2×15 mL) and brine (15 mL), dried ($Na_2SO_4$) and concentrated under reduced pressure to give a yellow oil which was purified by flash chromatography (silica, ethyl acetate/hexanes) to give N-(3-{(1S)-1-[(6-chloropyrazin-2-yl)amino]ethyl}phenyl)-6-methylnicotinamide (380 mg, 86%) as a white solid.

Example 2

A mixture of N-(3-{(1S)-1-[(6-chloropyrazin-2-yl)amino]ethyl}phenyl)-6-methylnicotinamide (74 mg, 0.2 mmol), 3-methoxyphenylboronic acid (40 mg, 0.26 mmol) and tetrakis(triphenylphosphine)palladium(0) (23 mg, 0.02 mmol) in toluene (3 mL) and n-propanol (1 mL) was evacuated and backfilled with nitrogen three times. To this mixture was added dilute aqueous sodium carbonate (0.15 mL, 2M, 0.3 mmol) and the mixture was heated at reflux for 17 hours. After this time the mixture was allowed to cool to room temperature and was diluted with ethyl acetate (20 mL) then washed successively with saturated aqueous sodium hydrogen carbonate (2×15 mL) and brine (15 mL), dried ($Na_2SO_4$) and concentrated under reduced pressure to give a yellow oil which was purified by flash chromatography (silica, ethyl acetate/methanol). The residue was dissolved in tetrahydrofuran (3 mL), treated with Si-Thiol for 1.5 hours, filtered through Celite and concentrated under reduced pressure to give the product (80 mg, 91%) as a white foam.

Example 3

To a solution of the aniline (66 mg, 0.15 mmol) in tetrahydrofuran (1 mL) at room temperature was sequentially added methanesulfonyl chloride (0.014 mL, 0.18 mmol) and triethylamine (0.052 mL, 0.38 mmol) dropwise. The resulting suspension was stirred at room temperature for 2.5 hours and was then diluted with ethyl acetate (10 mL) and water (10 mL). The two phases were separated and the aqueous phase extracted with ethyl acetate (2×10 mL) and the combined organic phases combined and extracted with dilute aqueous hydrochloric acid (2M, 3×10 mL). The combined acidic extracts were basified to pH>12 with solid potassium hydroxide and were extracted with ethyl acetate (3×10 mL). The organic extracts were washed with brine (10 mL), dried ($Na_2SO_4$) and concentrated under reduced pressure to give a yellow oil which was separated into its components by flash chromatography (silica, ethyl acetate/methanol) to yield the mono sulphonate (58 mg, 75%) and the bis sulphonate (15 mg, 17%).

Example 4

To a solution of benzaldehyde (0.1 mL, 1 mmol) and N-[(1S)-1-(3-aminophenyl)ethyl]-6-chloropyrazin-2-amine (248 mg, 1 mmol) in dichloroethane (5 mL) was added sodium triacetoxyborohydride (300 mg, 1.4 mmol) in one portion and the mixture was stirred at room temperature for 16 hours. After this time a solution of saturated aqueous sodium hydrogen carbonate (20 mL) was added and the mixture was stirred for 10 minutes. The mixture was extracted with ethyl acetate (2×20 mL) and the extracts washed with brine (20 mL), dried ($Na_2SO_4$) and concentrated under reduced pressure to give N-{(1S)-1-[3-(benzylamino)phenyl]ethyl}-6-chloropyrazin-2-amine (330 mg, 97%) as an off white solid of reasonable purity.

Example 5

A solution of the N-Boc material (200 mg, 0.38 mmol) in 20% trifluoroacetic acid in dichloromethane (5 mL) was stirred at room temperature for 1.5 hours. After this time the mixture was concentrated under reduced pressure and the residue was partially dissolved in water and the suspension basified to pH 12 with aqueous ammonia. The mixture was extracted with ethyl acetate (3×20 mL) and the combined extracts were washed with brine (10 mL), dried ($Na_2SO_4$) and concentrated under reduced pressure to give the secondary amine (155 mg, 95%) as a white foam.

Example 6

To a solution of the phenol (45 mg, 0.1 mmol) in tetrahydrofuran (5 mL) was added sodium tert-butoxide (12 mg, 0.11 mmol). After heating at 60° C. for 5 minutes tetrabenzylpyrophosphate (59 mg, 0.11 mmol) was added in one portion. The mixture was heated for 1.5 hours, cooled to room temperature, diluted with tetrahydrofuran (5 mL) and filtered through Celite. The filtrate was concentrated under reduced pressure to give a yellow oil which was purified by flash chromatography (silica, ethyl acetate/methanol) to give the dibenzylphosphate (62 mg, 87%) as an unstable pale yellow solid.

A mixture of dibenzylphosphate (10 mg, 0.014 mmol) and 10% palladium on carbon in methanol (3 mL) was stirred under an atmosphere of hydrogen for 16 hours after which time it was filtered through Celite and concentrated under reduced pressure to give the deprotected phosphate (6.7 mg, 89%) as a pale yellow solid.

Example 7

A mixture of N-(3-{(1S)-1-[(6-chloropyrazin-2-yl)amino]ethyl}phenyl)-3-methylbenzamide (73 mg, 0.2 mmol), 3-methoxyphenylboronic acid (46 mg, 0.3 mmol), tetrakis (triphenylphosphine)palladium(0) (23 mg, 0.02 mmol) and dilute aqueous sodium carbonate (0.2 mL, 2M, 0.4 mmol) in toluene (1.5 mL) and n-propanol (1.5 mL) was heated in a microwave reactor at 150° C. for 10 minutes. After this time the mixture was allowed to cool to room temperature and was diluted with ethyl acetate (20 mL) then washed successively with saturated aqueous sodium hydrogen carbonate (3×15 mL) and brine (15 mL), dried ($Na_2SO_4$) and concentrated under reduced pressure to give a brown oil which was purified by flash chromatography (silica, ethyl acetate/hexanes). The residue was dissolved in dichloromethane (3 mL), treated with Si-Thiol for 1.5 hours, filtered through Celite and concentrated under reduced pressure to give the product (80 mg, 91%) as a colourless oil.

Example 8

To a mixture of 5-aminonicotinic acid (35 mg, 0.25 mmol), N-[(1S)-1-(3-aminophenyl)ethyl]-6-chloropyrazin-2-amine (125 mg, 0.5 mmol) and N-(3-dimethylaminopropyl)-N'-ethylcarbodiimide hydrochloride (95 mg, 0.5 mmol) in N,N-dimethylformamide (2 mL) was added 1-hydroy-7-azabenzotriazole (1 mL, 0.5-0.7M in N,N-dimethylformamide, 0.5 mmol) then N-methylmorpholine (0.055 mL, 0.5 mmol) and the mixture was stirred at room temperature for 16 hours. After this time the mixture was diluted with ethyl acetate (40 mL), washed successively with saturated aqueous sodium hydrogen carbonate (2×30 mL) and brine (30 mL), dried ($Na_2SO_4$) and concentrated under reduced pressure to give a yellow oil which was purified by flash chromatography (silica, ethyl acetate/methanol) to give 5-amino-N-(3-{(1S)-1-[(6-chloropyrazin-2-yl)amino]ethyl}phenyl)nicotinamide (35 mg, 38%) as a pale yellow solid.

Example 9

To a solution of N-[1-(3-bromophenyl)ethyl]-6-chloropyrazin-2-amine (312 mg, 1 mmol) in methanol (10 mL) was added [1,1'-bis(diphenyl-phosphino)ferrocene]palladium[II] chloride, 1:1 complex with dichloromethane (146 mg, 0.2 mmol) then triethylamine (0.28 mL, 2 mmol). The mixture was evacuated and backfilled with carbon monoxide four times and then heated to reflux and stirred under an atmosphere of carbon monoxide for 17 hours. After this time the mixture was filtered through Celite to give a brown oil which was purified by flash chromatography (silica, ethyl acetate/hexanes) to give the methyl 6-{[1-(3-bromophenyl)ethyl]amino}pyrazine-2-carboxylate (90 mg, 27%) as a yellow oil.

Example 10

A mixture of (1S)-1-(3-nitrophenyl)ethanamine (365 mg, 2.2 mmol), 2,6-dibromopyridine (474 mg, 2 mmol), tris(dibenzylidene)dipalladium(0) (92 mg, 0.1 mmol), (+/−)-bis(diphenyphosphino)-1,1'-binaphthalene (125 mg, 0.2 mmol) and sodium tert-butoxide (270 mg, 2.8 mmol) in anhydrous toluene (4 mL) was heated at 80° C. for 17 hours. The mixture was cooled, diluted with ethyl acetate (50 mL), washed successively with saturated aqueous sodium hydrogen carbonate (3×30 mL) and brine (30 mL), dried ($Na_2SO_4$) and concentrated under reduced pressure to give a black oil which was purified by flash chromatography (silica, ethyl acetate/hexanes) to give 6-bromo-N-[(1S)-1-(3-nitrophenyl)ethyl]pyridin-2-amine (210 mg, 33%) and the di-addition product (205 mg, 50%) both as yellow oils.
To a solution of 6-bromo-N-[(1S)-1-(3-nitrophenyl)ethyl]pyridin-2-amine (100 mg, 0.31 mmol) in ethanol (5 mL) was added a solution of ammonium chloride (166 mg, 3.1 mmol) in water (2.5 mL), then indium powder (142 mg, mesh 100, 1.24 mmol). The mixture was heated at reflux for 4.5 hours, was allowed to cool to room temperature and was filtered through Celite. The filter cake was washed with water and ethanol and the combined filtrates were extracted with dichloromethane (2×30 mL) and the extracts washed with brine (30 mL), dried ($Na_2SO_4$) and concentrated under reduced pressure to give N-[(1S)-1-(3-aminophenyl)ethyl]-6-bromopyridin-2-amine (70 mg, 77%) as a dark yellow oil.
A mixture of N-[(1S)-1-(3-aminophenyl)ethyl]-6-bromopyridin-2-amine (70 mg, 0.24 mmol), 5-methylnicotinic acid (39 mg, 0.29 mmol), N-(3-dimethylaminopropyl)-N'-ethylcarbodiimide hydrochloride (69 mg, 0.36 mmol), 4-pyrrolidinopyridine (7 mg, 0.05 mmol) and triethylamine (0.08 mL, 0.58 mmol) in dichloromethane (3 mL) was stirred at room temperature for 17 hours. After this time the mixture was diluted with dichloromethane (20 mL), washed successively with saturated aqueous sodium hydrogen carbonate (2×15 mL) and brine (15 mL), dried ($Na_2SO_4$) and concentrated under reduced pressure to give a dark yellow oil which was purified by flash chromatography (silica, ethyl acetate/hexanes) to give N-(3-{(1S)-1-[(6-bromopyridin-2-yl)amino]ethyl}phenyl)-5-methylnicotinamide (62 mg, 63%) as a pale yellow foam.

Example 11

To a suspension of pyridine-3-sulfonylchloride hydrochloride (94 mg, 0.44 mmol) and N-[(1S)-1-(3-aminophenyl)ethyl]-6-chloropyrazin-2-amine (100 mg, 0.4 mmol) in dichloromethane (5 mL) was added triethylamine (0.17 mL, 1.2 mmol) dropwise at room temperature and the mixture was stirred for 17 hours. After this time the mixture was diluted with ethyl acetate (20 mL), washed successively with saturated aqueous sodium hydrogen carbonate (2×20 mL) and brine (20 mL), dried ($Na_2SO_4$) and concentrated under reduced pressure to give a yellow oil which was purified by flash chromatography (silica, ethyl acetate/hexanes) to give N-(3-{(1S)-1-[(6-chloropyrazin-2-yl)amino]ethyl}phenyl)pyridine-3-sulfonamide (44 mg, 28%) as a pale yellow foam.

Example 12

To a solution of 1-(5-methylpyridin-3-yl)ethanone (135 mg, 1 mmol) and N-[(1S)-1-(3-aminophenyl)ethyl]-6-chloropyrazin-2-amine (248 mg, 1 mmol) in 1,2-dichloroethane (5 mL) was added sodium triacetoxyborohydride (300 mg, 1.4 mmol), in one portion, and glacial acetic acid (0.18 mL, 3 mmol). The mixture was heated in the microwave reactor at 80° C. for 1 hour. After this time the mixture was stirred with dilute aqueous hydrochloric acid (2M, 7 mL) for 15 minutes and the two phases were separated. The aqueous phase was basified to pH 9 with solid potassium hydroxide and was extracted with dichloromethane (2×20 mL). The extracts were washed with brine (20 mL), dried ($MgSO_4$) and concentrated under reduced pressure to give an orange oil which was purified by flash chromatography (silica, ethyl acetate/methanol) to give 6-chloro-N-[(1S)-1-(3-{[1-(3-methylphenyl)ethyl]amino}phenyl)ethyl]pyrazin-2-amine (52 mg, 14%) as a pale yellow oil.

Example 13

A mixture of 3'-bromoacetophenone (2.66 mL, 20 mmol), ammonium formate (6.31 g, 100 mmol) and dichloro(pentamethylcyclopentadienyl)rhodium(III)dimer (124 mg, 0.2 mmol) in anhydrous methanol (20 mL) under an atmosphere of nitrogen was heated at reflux for 5 hours then allowed to cool to room temperature overnight. The mixture was diluted with water (20 mL), acidified to pH 2 with dilute aqueous hydrochloric acid (2M) and washed with dichloromethane (2×60 mL). The aqueous solution was basified to pH 12 with solid potassium hydroxide, extracted with dichloromethane (3×50 mL) and the extracts washed with brine (50 mL), dried ($Na_2SO_4$) and concentrated under reduced pressure to give 1-(3-bromophenyl)ethanamine (3.4 mg, 85%) as a yellow liquid.
A solution of 1-(3-bromophenyl)ethanamine (1 g, 5 mmol), di-tert-butyl-dicarbonate (1.1 g, 5 mmol) and triethylamine (0.85 mL, 6 mmol) in tetrahydrofuran (25 mL) was stirred at room temperature for 20 hours. After this time the mixture was concentrated under reduced pressure, the residue was dissolved in 50 ml dichloroethane and washed successively with saturated aqueous sodium hydrogen carbonate (3×20 mL) and brine (20 mL), dried ($Na_2SO_4$) and concentrated under reduced pressure to give tert-butyl 1-(3-bromophenyl)ethylcarbamate (1.5 g, 100%) as a white solid.

To a solution of tert-butyl 1-(3-bromophenyl)ethylcarbamate (300 mg, 1 mmol) in methanol (10 mL) was added [1,1'-bis(diphenyl-phosphino)ferrocene]palladium [II]chloride, 1:1 complex with dichloromethane (146 mg, 0.2 mmol) then triethylamine (0.28 mL, 2 mmol). The mixture was evacuated and backfilled with carbon monoxide four times and was then heated to reflux and stirred under an atmosphere of carbon monoxide for 17 hours. After this time the mixture was filtered through Celite to give a brown solid which was purified by flash chromatography (silica, ethyl acetate/hexanes) to give methyl 3-{1-[(tert-butoxycarbonyl)amino]ethyl}benzoate (210 mg, 75%) as a white solid. A solution of methyl 3-{1-[(tert-butoxycarbonyl)amino]ethyl}benzoate (200 mg, 0.72 mmol) in 20% trifluoroacetic acid in dichloromethane (10 mL) was stirred at room temperature for 1.5 hours. After this time the mixture was concentrated under reduced pressure and the residue was dissolved in water and basified to pH 11 with aqueous ammonia. The mixture was extracted with ethyl acetate (2×15 mL) and the extracts were washed with brine (20 mL), dried ($Na_2SO_4$) and concentrated under reduced pressure to give methyl 3-(1-aminoethyl)benzoate (130 mg, 100%) as a pale yellow oil. A mixture of methyl 3-(1-aminoethyl)benzoate (120 mg, 0.67 mmol), 2,6-dichloropyrazine (150 mg, 1 mmol) and potassium carbonate (280 mg, 2 mmol) in dioxane (5 mL) was heated in a microwave reactor at 150° C. for 6 hours. After this time the mixture was cooled to room temperature, filtered and concentrated under reduced pressure to give a yellow oil which was purified by flash chromatography (silica, ethyl acetate/hexanes) to give methyl 3-{1-[(6-chloropyrazin-2-yl)amino]ethyl}benzoate (30 mg, 15%) as a pale yellow oil. A mixture of methyl 3-{1-[(6-chloropyrazin-2-yl)amino]ethyl}benzoate (30 mg, 0.1 mmol) in dilute aqueous sodium hydroxide (0.5 mL, 2M, 1 mmol), methanol (2 mL) and dichloromethane (1 mL) was stirred at room temperature for 16 hours. After this time the mixture was concentrated under reduced pressure and the residue was dissolved in water (5 mL) which was then acidified to pH 6 with dilute aqueous hydrochloric acid (1M). The aqueous solution was extracted with ethyl acetate (3×10 mL) and the extracts were washed with brine (10 mL), dried ($MgSO_4$) and concentrated under reduced pressure to give 3-{1-[(6-chloropyrazin-2-yl)amino]ethyl}benzoic acid (11 mg, 41%) as a beige coloured oil. A mixture of 3-{1-[(6-chloropyrazin-2-yl)amino]ethyl}benzoic acid (11 mg, 0.04 mmol), 5-methylpyridin-3-amine (5 mg, 0.048 mmol), N-(3-dimethylaminopropyl)-N'-ethylcarbodiimide hydrochloride (11 mg, 0.059 mmol), 4-pyrrolidinopyridine (1.2 mg, 0.008 mmol) and triethylamine (0.013 mL, 0.095 mmol) in dichloromethane (1 mL) was stirred at room temperature for 17 hours. After this time the mixture was diluted with dichloromethane (20 mL), washed successively with saturated aqueous sodium hydrogen carbonate (2×15 mL) and brine (15 mL), dried ($Na_2SO_4$) and concentrated under reduced pressure to give a dark yellow oil which was purified by flash chromatography (silica, ethyl acetate/methanol) to give 3-{1-[(6-chloropyrazin-2-yl)amino]ethyl}-N-(5-methylpyridin-3-yl)benzamide (9 mg, 61%) as a pale yellow oil.

Example 14

To a vigorously stirred mixture of N-[(1S)-1-(3-aminophenyl)ethyl]-6-chloropyrazin-2-amine (49 mg, 0.2 mmol) and saturated aqueous sodium hydrogen carbonate (1.2 mL) in dichloromethane (1.2 mL) was added triphosgene (20 mg, 0.067 mmol) in one portion and the mixture was stirred for 3 hours. After this time 5-methylpyridin-3-amine (60 mg, 0.55 mmol) was added and the mixture was stirred for 17 hours. The mixture was then diluted with dichloromethane (20 mL) and was washed with brine (20 mL), dried ($MgSO_4$) and concentrated under reduced pressure. The residue was dissolved in ethyl acetate (20 mL) and extracted with dilute aqueous hydrochloric acid (0.5M, 3×15 mL). The combined acidic extracts were basified to pH 5 with solid potassium hydroxide and were then extracted with dichloromethane (3×20 mL). The combined organic extracts were washed with brine (20 mL), dried ($MgSO_4$) and concentrated under reduced pressure to give an orange oil which was purified by passage through a column of Sephadex with methanol as eluant. N-(3-{(1S)-1-[(6-Chloropyrazin-2-yl)amino]ethyl}phenyl)-N-(5-methylpyridin-3-yl)urea (32 mg, 42%) was obtained as a colourless foam.

Example 15

A mixture of N-(3-{(1S)-1-[(6-chloropyrazin-2-yl)amino]ethyl}phenyl)-5-methylnicotinamide (55 mg, 0.15 mmol) and morpholine (1.5 mL) was heated in a microwave reactor at 160° C. for 30 minutes and then for a further 1 hour at 180° C. The mixture was allowed to cool to room temperature and was diluted with ethyl acetate (30 mL), washed successively with water (6×15 mL) and brine (20 mL), dried ($Na_2SO_4$) and concentrated under reduced pressure to give a pale yellow oil which was purified by flash chromatography (silica, ethyl acetate/methanol) to give the product (32 mg, 51%) as a pale yellow oil.

Example 16

A mixture of N-(3-{(1S)-1-[(6-chloropyrazin-2-yl)amino]ethyl}phenyl)-3-methylbenzamide (183 mg, 0.5 mmol), 4-hydroxypiperidine (61 mg, 0.6 mmol), dicyclohexylphosphine (2-biphenyl) (4.6 mg, 0.012 mmol), tris(dibenzylidene)dipalladium(0) (4.6 mg, 0.005 mmol) and lithium bis(trimethylsilyl)amide (1.5 mL, 1M in tetrahydrofuran, 1.5 mmol) was heated in a microwave reactor at 100° C. for 30 minutes then at 140° C. for 30 minutes. The mixture was allowed to cool to room temperature and was then stirred vigorously with dilute aqueous hydrochloric acid (1M, 2 mL) for 15 minutes. The mixture was diluted with ethyl acetate (15 mL), the two phases separated and the organic phase dried ($MgSO_4$) and filtered through Celite to give a brown oil which was purified by flash chromatography (silica, ethyl acetate/methanol) followed by dissolution in dichloromethane (3 mL) and treatment with Si-Triamine to give the product (100 mg, 46%) as a yellow foam.

Example 17

To a mixture of 2,2,2-trifluoro-1-(5-methylpyridin-3-yl)ethanone (200 mg, 1.06 mmol), N-[(1S)-1-(3-aminophenyl)ethyl]-6-chloropyrazin-2-amine (263 mg, 1.06 mmol) and triethylamine (0.44 mL, 3.17 mmol) in dichloromethane (6 mL) was added titanium tetrachloride (0.52 mL, 1M in dichloromethane, 0.52 mmol) dropwise and the mixture was stirred at room temperature for 72 hours. After this time a solution of sodium triacetoxyborohydride (200 mg, 0.94 mmol) in methanol (2.5 mL) was added in one portion and the resulting suspension stirred for 3 hours. The mixture was basified to pH 12 with aqueous sodium hydroxide (2M), diluted with dichloromethane (20 mL) and washed successively with water (2×20 mL) and brine (20 mL), dried (Na$_2$SO$_4$) and concentrated under reduced pressure to give a yellow oil a portion of which was purified by passage through a column of Sephadex with methanol as eluant. The product (28 mg) was obtained as a yellow oil as a mixture of diastereoisomers.

Example 18

A solution of (S)-(−)-α,α-diphenyl-2-pyrrolidinemethanol (253 mg, 1 mmol) and trimethyl borate (0.135 mL, 1.2 mmol) in tetrahydrofuran (10 mL) was stirred at room temperature for 1 hour after which time borane-methylsulfide complex (10 mL, 2M in tetrahydrofuran, 20 mmol) was added in one portion and the mixture cooled to 0° C. A solution of 3-acetyl-5-bromopyridine (2 g, 10 mmol) in tetrahydrofuran (10 mL) was added dropwise over 2 hours at 0° C. and then the mixture was allowed to warm to room temperature and was stirred overnight. After this time dilute aqueous hydrochloric acid (2M, 90 mL) was added with initial cooling and the mixture was stirred at room temperature for 2 hours. Dimethyl sulfide and tetrahydrofuran were removed under reduced pressure and the resulting yellow solution was basified to pH 11 with aqueous ammonia, extracted with ethyl acetate (3×50 mL) and the extracts washed with brine (50 mL), dried (MgSO$_4$) and concentrated under reduced pressure to give (1R)-1-(5-bromopyridin-3-yl)ethanol (1.9 g) in acceptable purity.
To a solution of (1R)-1-(5-bromopyridin-3-yl)ethanol (10 mmol) in tetrahydrofuran (40 mL), cooled to 0° C., was added diphenylphosphoryl azide (4.3 mL, 20 mmol) in one portion followed by 1,8-diazabicyclo[5.4.0]undec-7-ene (3 mL, 20 mmol) dropwise over 30 minutes. After this time the reaction mixture was allowed to warm slowly to room temperature and was stirred overnight. The mixture was diluted with ethyl acetate (50 mL) and water (50 mL), the two phases separated and the aqueous phase extracted with ethyl acetate (3×50 mL). The combined organic phases were washed with brine (50 mL), dried (MgSO$_4$) and concentrated under reduced pressure to give a black liquid which was purified by flash chromatography (silica, ethyl acetate/hexanes) to give 3-[(1S)-1-azidoethyl]-5-bromopyridine (1.7 g, 75%) as a colourless liquid.
A mixture of m-toluamide (164 mg, 1.21 mmol), 3-[(1S)-1-azidoethyl]-5-bromopyridine (227 mg, 1 mmol), copper (I) iodide (9.6 mg, 0.05 mmol), N,N-dimethylethylene diamine (0.011 mL, 0.1 mmol) and potassium carbonate (276 mg, 2 mmol) in dioxane (1 mL) was heated in a microwave reactor at 110° C. for 30 minutes then at 160° C. for a further 30 minutes. After this time the mixture was allowed to cool to room temperature, was diluted with ethyl acetate (5 mL) and was filtered through Celite. The filtrate was concentrated under reduced pressure to give a brown oil which was purified by flash chromatography (silica, ethyl acetate/dichloromethane) to give N-{5-[(1S)-1-azidoethyl]pyridin-3-yl}-3-methylbenzamide (80 mg, 28%) as a colourless oil.
To a solution of N-{5-[(1S)-1-azidoethyl]pyridin-3-yl}-3-methylbenzamide (80 mg, 0.28 mmol) in a mixture of toluene (2 mL) and water (0.25 mL) was added triphenylphosphine (150 mg, 0.56 mmol) in one portion. The mixture was immediately heated to 80° C. where it was stirred for 3 hours. After this time the mixture was allowed to cool to room temperature, was diluted with ethyl acetate (10 mL), the two phases separated and the organic phase extracted with dilute aqueous hydrochloric acid (2M, 3×10 mL).
The acidic extracts were basified to pH>10 with solid potassium hydroxide and were then extracted with dichloromethane (3×10 mL). The organic extracts were washed with brine (10 mL), dried (Na$_2$SO$_4$) and concentrated under reduced pressure to give the N-{5-[(1S)-1-aminoethyl]pyridin-3-yl}-3-methylbenzamide (65 mg, 91%) as a yellow oil.
A mixture of N-{5-[(1S)-1-aminoethyl]pyridin-3-yl}-3-methylbenzamide (65 mg, 0.27 mmol), 2,6-dichloropyrazine (61 mg, 0.41 mmol) and potassium carbonate (76 mg, 0.54 mmol) in dioxane (2 mL) was heated in a microwave reactor at 150° C. for 1.5 hours. After this time the mixture was cooled to room temperature, filtered and concentrated under reduced pressure to give a yellow oil which was purified by flash chromatography (silica, ethyl acetate/methanol) to give N-(5-{(1S)-1-[(6-chloropyrazin-2-yl)amino]ethyl}pyridin-3-yl)-3-methylbenzamide (6 mg, 6%) as a pale yellow oil.

Example 19

To a solution of the alcohol (50 mg, 0.11 mmol) in tetrahydrofuran (1 mL), cooled to 0 C, was added diphenylphosphoryl azide (0.05 mL, 0.23 mmol) in one portion followed by 1,8-diazabicyclo[5.4.0]undec-7-ene (0.35 mL, 0.23 mmol) dropwise. After this time the reaction mixture was allowed to warm to room temperature and was stirred overnight. The mixture was diluted with ethyl acetate (10 mL) and water (10 mL), the two phases were separated and the aqueous phase was extracted with ethyl acetate (2×10 mL). The combined organic phases were washed with brine (15 mL), dried (Na$_2$SO$_4$) and concentrated under reduced pressure to give a brown oil which was purified by flash chromatography (silica, ethyl acetate/methanol) to give the product (40 mg, 55%) as a dark brown solid.

Example 20

To a solution of (S)—N-(3-(1-(6-chloropyrazin-2-ylamino)ethyl)phenyl)-3-nitro-5-(trifluoromethyl)benzamide (74 mg, 0.16 mmol) in ethanol (3 mL) was added a solution of ammonium chloride (85 mg, 1.6 mmol) in water (1.5 mL), then indium powder (73 mg, mesh 100, 0.64 mmol). The mixture was heated at reflux for 40 hours, was allowed to cool to room temperature and was filtered through Celite. The filter cake was washed with ethanol and the combined filtrates were concentrated under reduced pressure. The residue was dissolved in ethyl acetate (30 mL) and water (30 mL), the phases separated and the organic phase washed with brine (30 mL), dried (Na$_2$SO$_4$) and concentrated under reduced pressure to give a yellow oil which was purified by flash chromatography (silica, ethyl acetate/hexanes) to give (S)-3-amino-N-(3-(1-(6-chloropyrazin-2-ylamino)ethyl)phenyl)-5-(trifluoromethyl)benzamide (45 mg, 65%) as a pale yellow solid.

Example 21

A mixture of (S)—N-(3-(1-(6-chloropyrazin-2-ylamino)ethyl)phenyl)-3-methylbenzamide (55 mg, 0.15 mmol), benzylamine (0.033 mL, 0.3 mmol), bis(tri-t-butylphosphine)palladium(0) (8 mg, 0.015 mmol) and sodium tert-butoxide (22 mg, 0.225 mmol) in dry toluene (1 mL) was heated in a microwave reactor at 110° C. for 1 hour. After this time the mixture was allowed to cool to room temperature and was diluted with ethyl acetate (5 mL)/methanol (5 mL), filtered through Celite and concentrated under reduced pressure to give a yellow solid which was purified by flash chromatography (silica, ethyl acetate/hexanes) followed by passage through a column of Sephadex with methanol as eluant to give the (S)—N-(3-(1-(6-(benzylamino)pyrazin-2-ylamino)ethyl)phenyl)-3-methylbenzamide (13 mg, 20%) as an unstable blue oil.

Example 22

A mixture of (S)-3-amino-N-(3-(1-(6-chloropyrazin-2-ylamino)ethyl)phenyl)-5-(trifluoromethyl)benzamide (38 mg, 0.09 mmol), 2-chloroethyl ether (0.012 mL, 0.1 mmol) and potassium carbonate (30 mg, 0.21 mmol) in N,N-dimethyl formamide (1 mL) was heated in a microwave reactor at 180° C. for 40 minutes. After this time the mixture was allowed to cool to room temperature and was filtered through cotton wool, diluted with ethyl acetate (15 mL), washed with saturated aqueous sodium hydrogen carbonate (2×10 mL), water (2×10 mL), brine (2×10 mL), dried ($Na_2SO_4$) and concentrated under reduced pressure to give a brown oil which was purified by flash chromatography (silica, ethyl acetate/methanol) followed by passage through a column of Sephadex with methanol as eluant to give the byproduct (S,Z)—N-(3-(1-(6-chloropyrazin-2-ylamino)ethyl)phenyl)-3-((dimethylamino)methyleneamino)-5-(trifluoromethyl)benzamide (7 mg, 16%) as a yellow oil.

Example 23

A mixture of (S)-3-amino-N-(3-(1-(6-chloropyrazin-2-ylamino)ethyl)phenyl)-5-(trifluoromethyl)benzamide (43 mg, 0.1 mmol), iodomethane (0.04 mL, 0.5 mmol) and sodium hydride (20 mg, 60% oil dispersion, 0.5 mmol) in tetrahydrofuran (1 mL) was heated at 60° C. for 20 hours. After this time the mixture was allowed to cool to room temperature and was quenched with water (10 mL), diluted with saturated aqueous sodium hydrogen carbonate (15 mL), extracted with ethyl acetate (20 mL), washed with saturated aqueous sodium hydrogen carbonate (10 mL), brine (10 mL), dried ($Na_2SO_4$) and concentrated under reduced pressure to give a yellow oil which was purified by flash chromatography (silica, ethyl acetate/hexanes) followed by passage through a column of Sephadex with methanol as eluant to give a mixture of (S)-3-amino-N-(3-(1-(6-chloropyrazin-2-ylamino)ethyl)phenyl)-N-ethyl-5-(trifluoromethyl)benzamide, (S)-3-amino-N-(3-(1-((6-chloropyrazin-2-yl)(ethyl)amino)ethyl)phenyl)-N-ethyl-5-(trifluoromethyl)benzamide and (S)—N-(3-(1-((6-chloropyrazin-2-yl)(ethyl)amino)ethyl)phenyl)-N-ethyl-3-(ethylamino)-5-(trifluoromethyl)benzamide.

Example 24

A mixture of (S)—N-(3-(1-(6-chloropyrazin-2-ylamino)ethyl)phenyl)-3-methylbenzamide (183 mg, 0.5 mmol), [1,1'-bis(diphenylphosphino)ferrocene]palladium (II) chloride (73 mg, 0.1 mmol) and triethylamine (0.14 mL, 1 mmol) in methanol (5 mL) was heated at 80° C. under an atmosphere of carbon monoxide gas for 40 hours. After this time the mixture was allowed to cool, filtered through Celite and concentrated under reduced pressure to give a red solid which was purified by flash chromatography (silica, ethyl acetate/dichloromethane) to give (S)-methyl 6-(1-(3-(3-methylbenzamido)phenyl)ethylamino)pyrazine-2-carboxylate (48 mg, 25%) as a brown oil.

A solution of (S)-methyl 6-(1-(3-(3-methylbenzamido)phenyl)ethylamino)pyrazine-2-carboxylate (40 mg, 0.1 mmol) and aqueous ammonia (4 mL, 28%) in dioxane (2 mL) was heated at 130° C. in a sealed tube for 18 hours. After this time the mixture was allowed to cool to room temperature and was diluted with ethyl acetate (20 mL). The two phases were separated and the aqueous phase extracted with ethyl acetate (10 mL). The combined organic solutions were washed with brine (15 mL), dried ($Na_2SO_4$) and concentrated under reduced pressure to give (S)-6-(1-(3-(3-methylbenzamido)phenyl)ethylamino)pyrazine-2-carboxamide (37 mg, 98%) as a beige solid.

Example 25

A mixture of (S)—N-(3-(1-(6-chloropyrazin-2-ylamino)ethyl)phenyl)-3-methylbenzamide (92 mg, 0.25 mmol), palladium acetate (3 mg, 0.0125 mmol), (R)-(+)-2,2'-bis(diphenylphosphino)-1,1'-binaphthyl (8 mg, 0.0125 mmol), imidazole (17 mg, 0.25 mmol) and sodium tert-butoxide (36 mg, 0.375 mmol) in N,N-dimethyl formamide (0.5 mL) was heated in a microwave reactor at 180° C. for 20 minutes. After this time the mixture was allowed to cool to room temperature and was diluted with saturated aqueous sodium hydrogen carbonate (10 mL), extracted with ethyl acetate (3×15 mL), washed with brine (15 mL), dried ($Na_2SO_4$) and concentrated under reduced pressure to give a yellow oil which was purified by flash chromatography (silica, ethyl acetate/methanol) to give (S)—N-(3-(1-(6-(1H-imidazol-1-yl)pyrazin-2-ylamino)ethyl)phenyl)-3-methylbenzamide (40 mg, 40%) as a brown solid.

Example 26

A mixture of 5-benzimidazole carbonyl chloride (108 mg, 0.5 mmol), (S)—N-(1-(3-aminophenyl)ethyl)-6-chloropyrazin-2-amine (144 mg, 0.5 mmol) and triethylamine (0.7 mL, 5 mmol) was stirred at room temperature for 72 hours. After this time the mixture was allowed to cool to room temperature and was diluted with ethyl acetate (20 mL), washed with saturated aqueous sodium hydrogen carbonate (2×15 mL), brine (15 mL), dried ($MgSO_4$) and concentrated under reduced pressure to give a yellow oil which was purified by flash chromatography (silica, ethyl acetate/methanol) to give (S)—N-(3-(1-(6-chloropyrazin-2-ylamino)ethyl)phenyl)-1H-benzo[d]imidazole-6-carboxamide as a yellow powder.

Example 27

To a solution of (S)—N-(3-O-(6-(4-(hydroxymethyl)phenyl)pyrazin-2-ylamino)ethyl)phenyl)-3-(trifluoromethyl)benzamide (100 mg, 0.2 mmol) (made according to example 28) and triphenylphosphine (105 mg, 0.4 mmol) in dichloromethane (2.5 mL) was added a solution of carbon tetrabromide (132 mg, 0.4 mmol) in dichloromethane (1 mL) dropwise and the mixture was stirred at room temperature for 1 hour. After this time morpholine (0.07 mL, 0.8 mmol) was added and the mixture was stirred for a further 17 hours. After this time the mixture was diluted with ethyl acetate (30 mL), washed with saturated aqueous sodium hydrogen carbonate (2×20 mL) and extracted with dilute aqueous hydrochloric acid (2M, 3×30 mL). The acidic extracts were basified to pH>12 with solid potassium hydroxide and were then extracted with ethyl acetate (3×20 mL). The organic extracts were washed with brine (30 mL), dried ($Na_2SO_4$) and concentrated under reduced pressure to give a yellow oil which was purified by flash chromatography (silica, ethyl acetate/methanol) to give (S)—N-(3-(1-(6-(4-(morpholinomethyl)phenyl)pyrazin-2-ylamino)ethyl)phenyl)-3-(trifluoromethyl)benzamide (38 mg, 17%) as a yellow solid.

Example 28

To a degassed solution of (S)—N-(3-(1-(6-chloropyrazin-2-ylamino)ethyl)phenyl)-3-(trifluoromethyl)benzamide (210 mg, 0.5 mmol), 4-(hydroxymethyl)phenylboronic acid (152 mg, 1 mmol) and aqueous sodium carbonate (0.62 mL, 2M, 1.55 mmol) in N,N-dimethyl formamide (3 mL) was added dichloro[1,1'-bis(diphenylphosphino)ferrocene]palladium(II) (24 mg, 0.03 mmol) and the mixture was heated at 80° C. for 18 hours in a sealed tube. After this time the mixture was allowed to cool, was poured into a mixture of brine/water (2:3, 50 mL) and was extracted with a mixture of ethyl acetate/tetrahydrofuran (4:1, 3×30 mL). The combined organic extracts were concentrated under reduced pressure and the residue was taken up in ethyl acetate (50 mL), dried ($Na_2SO_4$) and concentrated under reduced pressure to give a black oil which was purified by flash chromatography (silica, ethyl acetate/hexanes) to give (S)—N-(3-(1-(6-(4-(hydroxymethyl)phenyl)pyrazin-2-ylamino)ethyl)phenyl)-3-(trifluoromethyl)benzamide (80 mg, 33%) as a pale yellow solid.

Example 29

To a solution of (R)-1-(3-nitrophenyl)ethanol (167 mg, 1 mmol) and 2,6-dichloropyrazine (164 mg, 1.1 mmol) in dioxane was added sodium hydride (88 mg, 60% oil dispersion, 2.2 mmol) in one portion and the mixture was heated at reflux for 4 hours. After this time the mixture was allowed to cool to room temperature and was poured into saturated aqueous sodium hydrogen carbonate (25 mL) and ethyl acetate (25 mL). The two phases were separated and the aqueous phase was extracted with ethyl acetate (25 mL). The combined organic phases were washed with brine (25 mL), dried ($Na_2SO_4$) and concentrated under reduced pressure to give (R)-2-chloro-6-(1-(3-nitrophenyl)ethoxy)pyrazine (250 mg, 89%) as an orange oil.

To a solution of (R)-2-chloro-6-(1-(3-nitrophenyl)ethoxy)pyrazine (240 mg, 0.86 mmol) in ethanol (12 mL) was added a solution of ammonium chloride (460 mg, 8.6 mmol) in water (6 mL), then indium powder (394 mg, mesh 100, 3.4 mmol). The mixture was heated at reflux for 20 hours, was allowed to cool to room temperature and was filtered through Celite. The filter cake was washed with ethanol and the combined filtrates were concentrated under reduced pressure. The residue was dissolved in ethyl acetate (25 mL) and was washed with water (15 mL), brine (15 mL), dried ($Na_2SO_4$) and concentrated under reduced pressure to give (R)-3-(1-(6-chloropyrazin-2-yloxy)ethyl)aniline as a dark yellow liquid (160 mg).

A mixture of (R)-3-(1-(6-chloropyrazin-2-yloxy)ethyl) aniline (160 mg, 0.64 mmol), 3-trifluoromethylbenzoic acid (183 mg, 0.96 mmol), N-(3-dimethylaminopropyl)-N'-ethylcarbodiimide hydrochloride (246 mg, 1.28 mmol), 4-dimethylamino pyridine (4 mg, 0.032 mmol) and triethylamine (0.36 mL, 2.57 mmol) in dichloromethane (6 mL) was stirred at room temperature for 18 hours. After this time the mixture was diluted with dichloromethane (30 mL), washed successively with saturated aqueous sodium hydrogen carbonate (2×20 mL) and brine (20 mL), dried ($Na_2SO_4$) and concentrated under reduced pressure to give an orange oil which was purified by flash chromatography (silica, ethyl acetate/hexanes) to give (R)—N-(3-(1-(6-chloropyrazin-2-yloxy)ethyl) phenyl)-3-(trifluoromethyl)benzamide (110 mg, 30% over 2 steps) as a yellow foam.

Example 30

Enzyme Screening

Compound Dilution

For screening purposes, compounds were diluted in 96 well plates at a concentration of 20 μM. Plates were warmed at 37° C. for 30 minutes before assay.

CSF1-R and c-KIT Tyrosine Kinase Domains Production

The kinase domains were produced in the following manner:

CSF-1R

The kinase domain of human CSF1-R from codon I553 to Q961 was cloned into the pDEST-20 expression vector (Invitrogen). The CSF1-R plasmid was then transformed into competent DH10Bac cells (Gibco), and the recombinant baculovirus produced prepared for transfection into Sf9 insect cells.

c-KIT

The kinase domain of human c-kit from codon M552 to end was cloned into the pDEST-20 expression vector (Invitrogen). The c-kit plasmid was then transformed into competent DH10Bac cells (Gibco), and the recombinant baculovirus produced prepared for transfection into Sf9 insect cells.

Large Scale Production of Kinase Domains

Baculovirus preparations from each of construct were infected into five liters of SF9 cells (Invitrogen) grown in SF-900 medium (Invitrogen) to a cell density of approximately $1-2 \times 10^6$ cells/ml. Cells are infected with virus at a MOI of 0.8-3.0. Cells were harvested and lysed. Tyrosine kinase domains were purified by affinity chromatography on a glutathione-agarose column (Scientifix Pty. Ltd. catalog #: GSH-200).

FLT-3 and PDGFR β tyrosine kinase enzymes were purchased from Upstate Cell Signalling Solutions, CA, USA (flt-3 catalog #: 14-500 and PDGFR β catalog #: 14-463). KDR protein kinase enzyme was purchased from Millipore (catalogue #14-630M).

Assay Protocols

Kinase assays were performed in 384 well Optiplates (Packard) using an Alphascreen Protein Tyrosine Kinase kit. Using approximately 1-50 ng of affinity purified PTK domain in the presence of 50 mM HEPES, pH 7.5, 10 mM $MgCl_2$, 150 mM NaCl and 10 μM-1 mM ATP. The biotinylated peptides Biotin-EQEDEPEGDYFEWLEPE-$NH_2$ for c-KIT and PDGFRβ and Biotin-EGPWLEEEEEAYGWMDF-$NH_2$ for CSF1-R and FLT-3 (final concentration 0.1-3 μM) were used as substrates. Alphascreen phosphotyrosine acceptor beads followed by streptavidin donor beads were added under subdued light. The Alphascreen plates were read on a Packard Fusion Alpha. Inhibitors were added to the assays thirty minutes prior to the addition of ATP. Inhibitors were added in aqueous DMSO, with DMSO concentrations never exceeding 1%.

Table 2 shows the results of biological assays for compounds according to the present invention.

TABLE 2

| Compound No. | CSF-1R | c-KIT | Flt3 | PDGFRβ | KDR |
| --- | --- | --- | --- | --- | --- |
| 1 | +++ | +++ | − | ++ | NT |
| 3 | +++ | +++ | NT | +++ | NT |
| 7 | +++ | +++ | + | +++ | NT |
| 11 | ++ | ++ | NT | ++ | NT |
| 13 | +++ | +++ | NT | +++ | NT |
| 16 | +++ | +++ | NT | ++ | NT |

TABLE 2-continued

| Compound No. | CSF-1R | c-KIT | Flt3 | PDGFRβ | KDR |
|---|---|---|---|---|---|
| 19 | +++ | +++ | NT | ++ | NT |
| 20 | +++ | +++ | NT | ++ | NT |
| 22 | +++ | +++ | NT | ++ | NT |
| 24 | +++ | +++ | + | +++ | +++ |
| 28 | +++ | +++ | + | +++ | NT |
| 29 | +++ | +++ | + | +++ | NT |
| 35 | +++ | ++ | NT | ++ | NT |
| 36 | +++ | +++ | NT | ++ | NT |
| 38 | +++ | +++ | + | NT | NT |
| 42 | +++ | +++ | − | ++ | NT |
| 59 | +++ | +++ | − | +++ | NT |
| 62 | +++ | +++ | NT | +++ | +++ |
| 65 | +++ | +++ | NT | +++ | +++ |
| 76 | +++ | +++ | + | ++ | NT |
| 77 | +++ | +++ | − | ++ | +++ |
| 78 | +++ | +++ | − | ++ | NT |
| 79 | +++ | +++ | − | ++ | NT |
| 80 | +++ | +++ | − | ++ | NT |
| 81 | +++ | +++ | − | ++ | NT |
| 82 | +++ | ++ | − | ++ | NT |
| 83 | +++ | ++ | ++ | ++ | NT |
| 90 | +++ | ++ | + | ++ | NT |
| 91 | +++ | ++ | − | ++ | NT |
| 93 | +++ | ++ | − | ++ | NT |
| 95 | +++ | ++ | − | ++ | NT |
| 100 | +++ | ++ | NT | +++ | +++ |
| 114 | +++ | ++ | NT | +++ | +++ |
| 127 | | | | | |
| 129 | +++ | +++ | NT | +++ | +++ |
| 133 | +++ | +++ | NT | +++ | +++ |
| 143 | +++ | +++ | NT | +++ | +++ |
| 147 | +++ | +++ | NT | +++ | +++ |
| 148 | +++ | +++ | NT | +++ | +++ |
| 149 | +++ | ++ | NT | +++ | +++ |
| 169 | ++ | ++ | | | +++ |
| 173 | +++ | | | | |
| 174 | +++ | +++ | | | +++ |
| 177 | +++ | | | | |
| 178 | +++ | ++ | | | +++ |
| 179 | +++ | +++ | | | +++ |
| 181 | +++ | +++ | | | +++ |
| 182 | +++ | ++ | | | +++ |
| 183 | +++ | ++ | | | +++ |
| 185 | +++ | ++ | | | +++ |
| 187 | +++ | ++ | | | +++ |
| 188 | +++ | +++ | | | +++ |
| 189 | +++ | ++ | | | +++ |
| 190 | +++ | +++ | | | +++ |
| 191 | +++ | +++ | | | +++ |
| 192 | +++ | +++ | | | +++ |

Where:
+++ = $IC_{50}$ less than 100 nM
++ = $IC_{50}$ less than 1 uM
+ = $IC_{50}$ less than 10 uM
− = $IC_{50}$ more than 10 uM
NT = Not tested Example 31

Additional Enzyme Screening

Further enzyme assays were conducted at Upstate Biotechnology (Dundee, UK) in the KinaseProfiler™ Assay system.

The general protocol is as follows. All kinases are pre-diluted to a 10× working concentration prior to addition into the assay. The composition of the dilution buffer for the kinases is 20 mM MOPS pH 7.0, 1 mM EDTA, 0.1% β-mercaptoethanol, 0.01% Brij-35, 5% glycerol, 1 mg/ml BSA. All substrates are dissolved and diluted to working stocks in de-ionised water.

The specific details for each kinase screened is given below:

EphA2 (h)

In a final reaction volume of 25 EphA2 (h) (5-10 mU) is incubated with 8 mM MOPS pH 7.0, 0.2 mM EDTA, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

EphA3 (h)

In a final reaction volume of 25 EphA3 (h) (5-10 mU) is incubated with 8 mM MOPS pH 7.0, 0.2 mM EDTA, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

Flt1(h)

In a final reaction volume of 25 Flt1 (h) (5-10 mU) is incubated with 8 mM MOPS pH 7.0, 0.2 mM EDTA, 250 μM KKKSPGEYVNIEFG, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Hck(h)

In a final reaction volume of 25 μl, Hck (h) (5-10 mU) is incubated with 8 mM MOPS pH 7.0, 0.2 mM EDTA, 250 μM KVEKIGEGTYGVVYK (Cdc2 peptide), 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Lck(h)

In a final reaction volume of 25 μl, Lck (h) (5-10 mU) is incubated with 50 mM Tris pH 7.5, 0.1 mM EGTA, 0.1 mM Na₃VO4, 250 μM KVEKIGEGTYGVVYK (Cdc2 peptide), 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Ret(h)

In a final reaction volume of 25 μl, Ret (h) (5-10 mU) is incubated with 8 mM MOPS pH 7.0, 0.2 mM EDTA, 250 μM KKKSPGEYVNIEFG, 10 mM MgAcetate and [γ-33P-ATP]

(specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

The results are outlined in Table 3 expressed as % inhibition.

TABLE 3

| | compound 77 | | compound 143 | | compound 149 | | compound 114 | | compound 129 | | compound 133 | | compound 147 | | compound 148 | | compound 168 | |
|---|---|---|---|---|---|---|---|---|---|---|---|---|---|---|---|---|---|---|
| | 0.1 µM | 1 µM | 0.1 µM | 1 µM | 0.1 µM | 1 µM | 0.1 µM | 1 µM | 0.1 µM | 1 µM | 0.1 µM | 1 µM | 0.1 µM | 1 µM | 0.1 µM | 1 µM | 0.1 µM | 1 µM |
| cSRC(h) | 23 | 74 | 14 | 65 | 69 | 96 | 24 | 80 | 38 | 85 | 1 | 14 | 45 | 87 | 86 | 96 | 53 | 95 |
| EphA2(h) | 87 | 102 | 80 | 99 | 96 | 102 | 96 | 101 | 24 | 93 | 69 | 99 | 97 | 102 | 93 | 102 | 102 | 103 |
| EphA3(h) | 17 | 70 | 0 | 58 | 46 | 94 | 24 | 92 | 18 | 76 | -4 | 34 | 44 | 91 | 79 | 99 | 69 | 98 |
| EphA8(h) | 66 | 99 | 30 | 82 | 81 | 103 | 67 | 97 | 42 | 90 | 7 | 64 | 71 | 98 | 81 | 100 | 91 | 102 |
| Flt1(h) | 98 | 100 | 90 | 96 | 56 | 99 | 85 | 99 | 96 | 100 | 92 | 99 | 95 | 100 | 92 | 99 | 91 | 100 |
| Flt4(h) | 98 | 97 | 95 | 99 | 96 | 99 | 92 | 99 | 100 | 100 | 95 | 100 | 100 | 99 | 96 | 99 | 96 | 97 |
| Hck(h) | 64 | 95 | 55 | 82 | 94 | 100 | 74 | 102 | 84 | 99 | 23 | 84 | 90 | 100 | 96 | 99 | 96 | 101 |
| Lck(h) | 45 | 84 | 24 | 77 | 68 | 95 | 53 | 90 | 73 | 96 | 0 | 16 | 50 | 89 | 95 | 97 | 85 | 98 |
| PTK5(h) | 91 | 99 | 88 | 96 | 95 | 100 | 98 | 100 | 99 | 100 | 80 | 98 | 94 | 100 | 99 | 100 | 100 | 100 |
| Ret(h) | 22 | 67 | 8 | 58 | 89 | 96 | 66 | 95 | 19 | 75 | 1 | 36 | 68 | 92 | 89 | 96 | 39 | 95 |

Example 32

Cellular Assays

Cellular Assays were Performed as Follows:

Cells for the assays were prepared by harvesting cells from culture, and then diluting them in the appropriate growth medium to between 40,000 cell/mL and 600,000 cell/mL, depending on the cell line.

The compounds to be tested were added (10⁴, 10× final concentration) to a flat bottomed 96-well plate. The cellular suspension (80 µL per well) was added, and one hour later the growth factor was added (human M-CSF at 20 ng/ml for mNFS-60, mouse IL-3 at 5 ng/ml for Baf3-WT). The plate was then incubated for 72 hr at 37° C., 5% $CO_2$. Alamar Blue (10⁴ per well) was added and the plates returned to the incubator for a further 4-8 hours.

The plates were then read using a fluorescence plate reader at excitation 544 nm and emission 590 nm.

The results are outlined in Table 4

TABLE 4

| Compound No. | mNFS-60 | Baf3-WT |
|---|---|---|
| 24 | +++ | - |
| 62 | ++ | - |
| 65 | +++ | - |
| 77 | +++ | - |
| 100 | +++ | - |
| 114 | ++ | - |
| 127 | ++ | - |
| 129 | +++ | + |
| 133 | +++ | - |
| 143 | +++ | + |
| 147 | +++ | - |
| 148 | +++ | + |
| 149 | ++ | - |
| 169 | +++ | + |
| 173 | ++ | - |
| 174 | +++ | - |

TABLE 4-continued

| Compound No. | mNFS-60 | Baf3-WT |
|---|---|---|
| 177 | + | - |
| 178 | +++ | + |
| 179 | +++ | + |
| 181 | +++ | + |

TABLE 4-continued

| Compound No. | mNFS-60 | Baf3-WT |
|---|---|---|
| 182 | +++ | - |
| 183 | +++ | + |
| 185 | +++ | + |
| 187 | +++ | - |
| 188 | +++ | - |
| 189 | +++ | - |
| 190 | +++ | - |
| 191 | +++ | + |
| 192 | +++ | - |

+++ = $IC_{50}$ less than 200 nM
++ = $IC_{50}$ less than 1uM
+ = $IC_{50}$ less than 10 uM
- = $IC_{50}$ more than 10 uM
NT = Not tested

Example 33

Tumour Growth and Metastisis

The effects of compounds 28 and 59 on a mammary tumour cell line were investigated.

The neomycin-resistant tumour line was cultured in alpha-MEM plus 5% foetal calf serum and penicillin/streptomycin. Cells were lifted with EDTA (0.03%) and counted in a haema-cytometer to give a concentration of $1 \times 10^7$ cells per ml in phosphate buffered saline (PBS) for injection. Compounds 28 and 59 were dissolved in a vehicle containing DMSO:PEG: water at a ratio of 1:9:10. Compound 28 was dissolved at 6 mg/ml whilst Compound 59 was prepared at 4 mg/ml. The two compounds were administered twice daily as intraperitoneal injections at 60 mg/Kg (Compound 28) and 40 mg/Kg (Compound 59). A control group of mice was administered the vehicle only.

Tissues for tumour burden analysis from the liver were snap frozen in liquid nitrogen and pulverised in stainless steel homogenisers chilled to liquid nitrogen temperature.

Genomic DNA was isolated using proteinase K digestion, phenol:chloroform extraction and ethanol precipitation. Tumour burden for the liver was measured using RTQ-PCR incorporating TaqMan® chemistry (Applied Biosystems, Foster City, Calif.). RTQ-PCR detects the cycle threshold (Ct) for vimentin DNA (endogenous mouse tissue) and neomycin DNA (tumour cells only). By comparing these two Ct values, a score for relative tumour burden (RTB) was calculated using the following formula:

$$RTB=10000\times 1/2e^{\Delta Ct}$$

Using this formula, a tissue without tumour scores zero, whilst a tissue comprised entirely of tumour cells scores 10,000. PCR was performed using an ABI Prism 7000 thermocycler (Applied Biosystems). All PCR reagents were obtained from Applied Biosystems except for neomycin and vimentin forward and reverse primers (GeneWorks, Australia). Sequences for primers and probes used in TaqMan® assays were designed using Primer Express version 2.0 software (Applied Biosystems).

The tumor burden reported in the presence of compound 28 and compound 59 compared with that of vehicle is shown in FIG. 1.

Example 34

Mesothelioma Model

In a mesothelioma model, the mesothelioma cell line that was originally derived from Balb/C mice was injected into two groups of twenty mice at $10^6$ cells subcutaneously per mouse. Vehicle (DMSO:PEG400:water at a ratio of 1:9:10) or compound 28 60 mg/kg in this vehicle were given to each group from the time of tumour inoculation by i.p. at 200 µl injection twice daily. The experiment was allowed to proceed for 19 days during which time the daily body weight was recorded. The tumour size of each mouse was measured from day 7 until end of the experiment. At the end of the experiment, the mice were killed and the tumour exercised and weighed.

Figure 2:
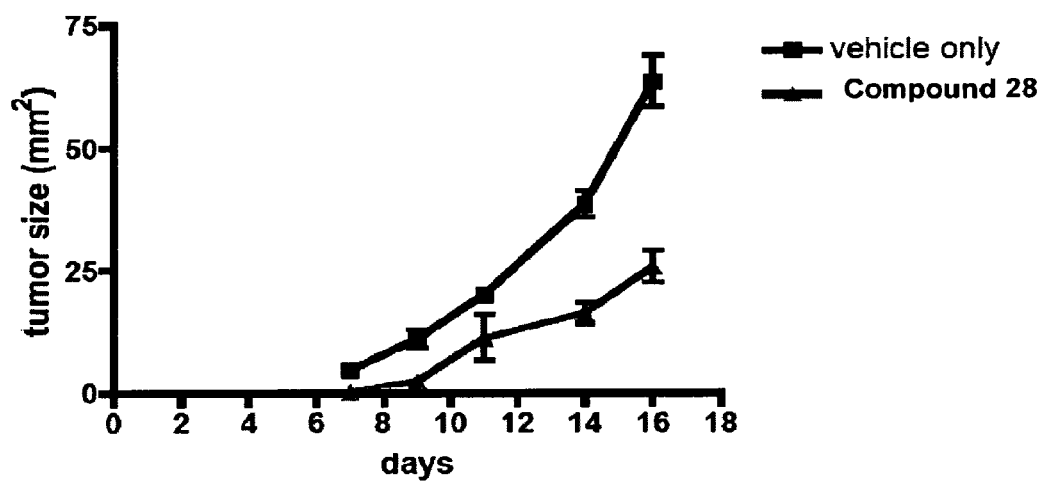
FIG. 2 is a graph showing the progression of tumour size after administration of Compound 28 compared with Vehicle as described in Example 34.

The progression of tumour size after administration of compound 28, compared with vehicle, is shown in FIG. 2.

Example 35

Cell lines derived from human tumors including pancreatic, lung, ovarian, oesophageal, colonic, neuroblastoma, melanoma, mesothelioma and gastric cancers can be used to verify the efficacy of kinase inhibitor molecules. The effects of elevated SRC kinase activity have been extensively studied in vitro using a variety of human neoplastic cell lines and in vivo with murine models. Using these systems, the effects of SRC on tumour initiation and progression have been studied and a role for c-SRC in almost every aspect of a cell's life has been suggested including mitogenesis, proliferation, survival, control of cellular adhesion and migration. All of these processes are de-regulated during cancer progression. Elevated SRC kinase activity has been found in human mammary carcinoma. In one validation model, a human breast cancer cell line, MDA-MB-231, can be injected into the left ventricle of Balb/C-nu/nu mice. A c-SRC inhibitor, can be given by p.o. route, to examine the effect on morbidity and lethality, and the effect on the incidence of metastases both in bone and visceral organs. Osteoclast formation and bone resorption can also be assessed to verify the effect on osteoclast activity. One advantage for using SRC inhibitors for cancer therapy is that deficiency of SRC in mice appears to affect only bone cell formation with no effects on other organs.

Cardiovascular Diseases such as artherosclerosis provide another potential therapeutic use for FMS inhibitors. Experimentally, the efficacy of FMS inhibitors can be investigated in two mouse models of artherosclerosis. In the first approach, inhibitors or vehicle controls are given to apolipoprotein E knock-out (apoE-KO) mice for 17 weeks fed a normal chow diet. In this model, early lesions can be assessed by histomorphometric analysis of fatty streaks containing macrophage-derived foam cells with intracellular lipid accumulation (AHA TYPE II) or pools of extracellular lipid (AHA type III) whereas advanced lesions are seen as extracellular lipid, a lipid core (AHA typeIV) and/or a bifrous cap (AHA type Va-c). Other assessment parameters include immunohistochemical analysis assessing T cells and macrophage contents, lipid core content, collagen content and α-smooth muscle actin (ASMA) content. Another model utilises LDL-R deficient mice given a high-cholesterol diet for 13 weeks to induce lesions. Inhibitors are given for an additional 13 weeks after which computer-assisted image quantification is used to determine the thickness of the aortic wall, medial and intima area. Other parameters of interest are macrophage, lipid, smooth muscle cells (SMC) and collagen positive areas.

Acute episodes of renal allograft rejection also provides an opportunity for therapeutic intervention using a FMS inhibitor may be of use is in as macrophages have been shown to accumulate in the graft by recruitment and local proliferation. It has been documented in a mouse model in which kidneys from C57BL/6 mice were allografted onto Balb/C mice. Anti-fms antibodies given immediately post-operatively by i.p. injections daily at 50 mg/kg/day were seen to reduce proliferating macrophages by 82%, interstitial macrophages accumulation by 53% and glomerular macrophages by 71%. The macrophages were detected by CD68 staining. Moreover, the severity of tubulointerstitial rejection was reduced as shown by decreased tubulitis. Degree of tubulitis was defined by the BANFF 97 classification of renal allograft pathology which assessed each tubular cross-section as (1) normal tubule (2) tubular atrophy (3) mild tubulitis (4) moderate tubulitis and (5) severe tubulitis according to the degree of tubular basement membrane disruption and the number of infiltrating mononuclear cells. Other measurements include serum creatinine plus urinalysis for protein excretion and full blood count for impact on bone marrow. This model is therefore a useful verification for other small molecule inhibitors of FMS, such as those in the present invention.

Rheumatoid arthritis (RA) is a chronic, destructive inflammatory polyarticular joint disease characterised by passive synovial proliferation and subintimal infiltration of inflammatory cells. Although the aetiology remains to be elucidated, it is generally acknowledged that RA is an autoimmune disease and arthritis is a consequence of loss of tolerance against a cartilage specific autoantigen. In this context, animal models have been established that evolves around induction of RA by an autoantigen such as 1. type II collagen-induced arthritis (CIA) and 2. a combination of an antigen from gram-ve bacteria (LPS) with a panel of 4 monoclonal antibodies (mAb). A third model of arthritis is the Adjuvant-induced arthritis (AIA) which is performed mainly in rats. The underlying mechanism of AIA is still controversial. However, a 65 kD myobacterial heat shock protein was shown to share a nonapeptide sequence in the core protein molecule of proteoglycan, and suggests that AIA is also a disease inducible by autologous antigen.

In AIA, eight-week old Lewis rats are given Complete Freund's Adjuvant (CFA) prepared by suspending as an emulsion of heat-killed *Mycobacterium* butyricum in liquid paraffin at 12 mg/ml. CFA-induced arthritis can be stimulated by injection of 50 µl of CFA emulsion intradermally either in to the footpad or to the base of the tail. From day 7 (onset of arthritis), rats are examined daily for clinical arthritic score on a 0-4 scale: 0, normal; 1, minimal swelling; 2, medium swelling; 3, severe swelling; and 4, severe and non-weight bearing. For each limb, the mid-forpaw, the wrist, the joints of the fingers, the midfoot, the ankle and the joints of the digits are scored giving a maximum clinical score of 48 per rat. The animals are sacrificed on day 17 and the hindpaws are amputated and fixed in 7.4% formalin. After decalcification and embedment in paraffin, the limbs are sectioned in a mid-sagittal plane, stained by eosin and hematoxylin and examined microscopically for pannus formation (cartilage and bone erosion and destruction), vascularity (blood vessel formation by CD31 staining) and mononuclear cell infiltration (T, B and macrophages).

In CIA, DBA/1 mice that bear $H$-$2^q$ MHC haplotype are used as they are more susceptible to CIA. In general, heterologous collagen is used as they are more immunogenic/ arthritogenic tha homologous type II collagen. The mice are primed with an emulsion consisting of bovine type II collagen and Complete-Freund's Adjuvant at a 1:1 ratio (final concentration=2 mg/ml). The emulsion (0.1 ml) is injected into the tail of each mouse approximately 1-2 cm from the base. A whitish bolus beneath the dermis should be visible. A type II collagen booster (200 µg per mouse) is given intraperitoneally in PBS on day 21. High CIA-susceptible mice (DBA/ 1) generally develop arthritis 4-5 weeks after initial priming. Fully developed arthritis including red and swollen paws, can be observed 3-5 days after the onset and active inflammatory arthritis persists more than 3-4 weeks. Although inflammation will eventually subside, joint damage as seen as ankylosis is permanent. Assessment of CIA symptoms is essentially similar to the AIA model in which clinical signs is assigned clinical score (0-4) based on the severity of the disease. Histological measurements can also be performed on formalin-fixed joints to assess erosin, cellular infiltrates and hyperplasia.

In combined LPS-mAB induced Arthritis, a severe and consistent arthritis can be induced in mice by a combination of LPS and mAB cocktail that recognize individual epitopes clustered within an 83 amino acid peptide fragment located within CB11 region of type II collagen. This model was developed based on the hypothesis that bacterial toxin(s) absorbed through the GI tract play a synergistic and pathologic role with sub-arthritogenic levels of autoantibodies to type II collagen in triggering RA. The advantages of this model are: 1. synchronized arthritis (100%) is induced rapidly within 7 days 2. a variety of mouse strains can be used as administration of anti-type II collagen mAB cocktail bypasses the requirement for the host's generation of autoantibodies to type II collagen thus arthritis can be induced in mice that do not possess CIA-susceptible MHC haplotypes and 3. ease of administration of mAB and LPS by either i.v. and i.p. routes.

Inflammmatory Bowel Diseases (IBD) which includes Crohn's disease (CD) and ulcerative colitis (UC) represents a group of chronic disorders characterized by inflammation of the gastrointestinal tract. CD can affect any part of the digestive track whereas UC affects only the colon and rectum. UC causes inflammation and ulcers, usually in the sigmoid colon and rectum. Cellular infiltrates are complex and pro-inflammatory cytokines are evident in CD and UC.

An experimental model of UC is established in Balb/C mice by administration of dextran sulphate sodium (3% DSS) isolated from *Leuconostoc* spp. into the drinking water. The experiment has a relatively short time-course (8 days) and parameters for assessment of colitis include loss of body weight, stool consistency, rectal bleeding, shortening of colonic length, crypt damage and cytokine analysis of colonic rings.

In CD, Balb/C mice are sensitized at day 0 with 2×50 µl of 5 mg/ml of dinitrofluobenzene (DNFB) epicutaneously to shaved abdomen and feet on two consecutive days. DNFB is typically solubilised in acetone:olive oil (4:1). On day 5, the mice are challenged intracolonically with 50 µl dintrobenzene sulphonic acid (DNS) at 6 mg/ml in 10% ethanol. The mice are sacrificed on day 8. Parameters to be measured include suppression of total blood cell number and cell types, mucosal mast cell protease 1 (MMCP-1) in serum, TNFα level in colon homogenate, stool consistency, vascular permeability and number of colonic patches. Number of neutrophils and mast cells which are indicative of colonic damage and cellular influx will also be assessed by histological and microscopical examinations.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of formula I:

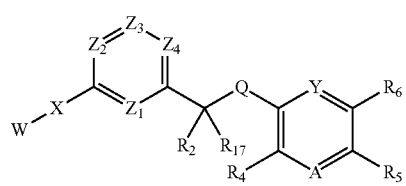

I wherein

Q is $NR_3$;

W is cyclopropyl, or a saturated or unsaturated 5 or 6 membered heterocyclyl containing 1 or 2 heteroatoms selected from N, O and S wherein the cyclopropyl, or saturated or unsaturated 5 or 6 membered heterocyclyl may be substituted with 1 or 2 substituents independently selected from the group consisting of $C_{1-4}$alkyl, OH, $NO_2$, $NR_7R_8$, halogen, $CF_3$, $CO_2R_9$, $OC_{1-4}$alkyl, $COR_9$, $SO_2 C_{1-4}$alkyl and a saturated or unsaturated 5 or 6 membered heterocyclyl containing 1 or 2 heteroatoms selected from the group consisting of N, O and S;

X is selected from the group consisting of NHCO and CONH;

each of $Z_1$, $Z_2$, $Z_3$ and $Z_4$ is independently selected from the group consisting of N and $CR_1$ provided that no more than two of $Z_1$, $Z_2$, $Z_3$ and $Z_4$ are N;

each $R_1$ is independently selected from the group consisting of H, halogen, $CF_3$, $OCF_3$, $C_{1-4}$alkyl and $OC_{1-4}$alkyl;

$R_2$ and $R_{17}$ are independently selected from the group consisting of H, $C_{1-4}$alkyl, $CF_3$, $C_{1-4}$alkylOH and $C_{1-4}$alkylOC$_{1-4}$alkyl or $R_2$ and $R_{17}$ together with the carbon atom to which they are attached form $C_{3-8}$cycloalkyl or 3, 4, 5, 6, 7 or 8 membered saturated heterocyclyl;

$R_3$ is selected from the group consisting of H and $C_{1-4}$alkyl;

A is N and Y is $CR_3$ or A is $CR_3$ and Y is N;

$R_4$ and $R_5$ are independently selected from the group consisting of H, $C_{1-4}$alkyl, $CF_3$, halogen and $NR_9R_{10}$;

$R_6$ is selected from the group consisting of H, halogen, $OR_{11}$, $NR_{12}R_{13}$, $C_{1-4}$alkyl, $C_{1-4}$alkylOH, $CO_2R_9$, $CONR_7R_8$, $S(O)_nR_{14}$, aryl and 5, 6 or 7 membered heterocyclyl having 1, 2 or 3 heteroatoms selected from the group consisting of N, O, S, SO and $SO_2$, wherein the aryl or heterocyclyl may be substituted with 1, 2 or 3 substituents independently selected from the group consisting of $C_{1-4}$alkyl, OH, $NR_{15}R_{16}$, halogen, $CF_3$, $OCF_3$, CN, $OC_{1-4}$alkyl, $OC_{2-4}$alkyleneOH, $OC_{2-4}$alkyleneNR$_7R_8$, $C_{1-4}$alkyleneOH, $C_{1-4}$alkyleneOC$_{1-4}$alkyl, $C_{1-4}$alkyleneNR$_7R_8$, $CONR_7R_8$, $CO_2R_9$, $NR_7COR_9$, $NR_7SO_2C_{1-4}$alkyl, $N(SO_2C_{1-4}alkyl)_2$, $NR_7CONR_8C_{1-4}$alkyl, $SO_2NR_9R_{10}$, $OP(O)(OR_7)_2$, $SO_2C_{1-4}$alkyl, aryl and heterocyclyl;

n is 0, 1 or 2;

$R_7$ and $R_8$ are independently selected from the group consisting of H, $C_{1-4}$alkyleneOH, $C_{1-4}$alkylene OC$_{1-4}$alkyl, $C_{1-4}$alkylene NR$_{15}R_{16}$, COC$_{1-4}$alkyl and aryl; or $R_7$ and $R_8$ together with the nitrogen to which they are attached form a 5, 6, or 7 membered heterocyclyl which contains 1 or 2 heteroatoms selected from the group consisting of N, O, S, SO and $SO_2$ and which may be substituted with H, $C_{1-4}$alkyl, $OR_9$ or $NR_9R_{10}$;

$R_9$ and $R_{10}$ are independently selected from the group consisting of H and $C_{1-4}$alkyl;

$R_{11}$ is independently selected from the group consisting of H, $C_{1-4}$alkyl, $C_{2-4}$alkyleneOH and $C_{2-4}$alkylene NR$_7R_8$;

$R_{12}$ and $R_{13}$ are independently selected from the group consisting of H, $C_{1-4}$alkyl, aryl, $C_{2-4}$alkyleneOH, COC$_{1-4}$alkyl, COaryl and COheterocyclyl; or $R_{12}$ and $R_{13}$ together with the nitrogen to which they are attached form a 5, 6, or 7 membered heterocyclyl which contains 1 or 2 heteroatoms selected from N, O, S, SO and $SO_2$ and which may be substituted with $C_{1-4}$ alkyl, $OR_9$ or $NR_9R_{10}$;

$R_{14}$ is aryl or a 5, 6, or 7 membered heterocyclyl having 1, 2 or 3 heteroatoms selected from the group consisting of N, O, S, SO and $SO_2$, wherein the aryl or heterocyclyl may be substituted with 1, 2 or 3 substituents selected from the group consisting of $C_{1-4}$alkyl, OH, $NR_{15}R_{16}$, halogen, $CF_3$, $OCF_3$, CN, $OC_{1-4}$alkyl, $OC_{2-4}$alkyleneOH, $C_{1-4}$alkylene OH, $C_{1-4}$alkyleneOC$_{1-4}$alkyl, $C_{1-4}$alkyleneNR$_{15}R_{16}$, $CONR_{15}R_{16}$, $CO_2R_9$, $NR_7SO_2CH_3$, $N(SO_2CH_3)_2$, $NR_7CONR_8C_{1-4}$alkyl, $SO_2NR_{15}R_{16}$, $OP(O)(OR_7)_2$, aryl and heterocyclyl;

$R_{15}$ and $R_{16}$ are independently selected from the group consisting of H, $C_{1-4}$alkyl, $C_{1-4}$alkylOH, $C_{1-4}$alkyl OC$_{1-4}$alkyl, COC$_{1-4}$alkyl and $S(O)CH_3$; or $R_{15}$ and $R_{16}$ together with the nitrogen to which they are attached form a 5 or 6 membered heterocyclyl which contains 1 or 2 heteroatoms selected from N, O and S which may be substituted with $C_{1-4}$alkyl, $OR_9$ or $NR_9R_{10}$, or a pharmaceutically acceptable salt thereof or stereoisomer thereof.

2. The compound according to claim 1, wherein the compound of formula I has the formula Ia

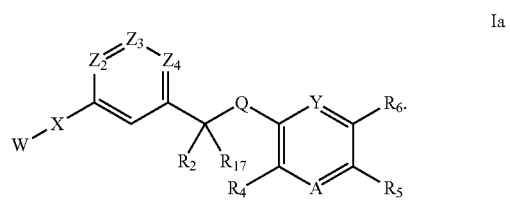

3. The compound according to claim 1, wherein the compound of formula I has the formula Ib

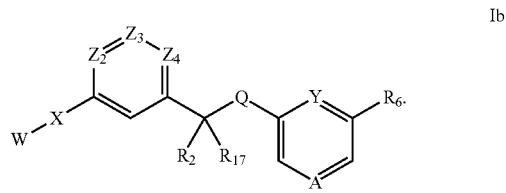

4. The compound according to claim 3, wherein $R_6$ is H, halogen, $CO_2R_9$, $CONR_7R_8$, phenyl, saturated or unsaturated 5 or 6 membered heterocyclyl containing 1 or 2 heteroatoms selected from the group consisting of N, O and S, or a condensed heterocyclyl containing 1 or 2 oxygen atoms, wherein the phenyl or heterocyclyl may be substituted with 1 or 2 substituents independently selected from the group consisting of $OC_{1-4}$alkyl, OH, $NR_7CONR_8$, $NR_{15}R_{16}$, $SO_2NR_9R_{10}$, $OP(O)(OH)_2$, $CO_2R_9$, $C_{1-4}$alkylOH, $C_{1-4}$alkyleneNR$_{15}R_{16}$ and 6 membered heterocyclyl containing 1 or 2 heteroatoms selected from the group consisting of N and O.

5. The compound according to claim 1, wherein one of $R_2$ and $R_{17}$ is H and the other is H or $C_{1-4}$alkyl.

6. The compound according to claim 1, wherein both $R_4$ and $R_5$ are H.

7. The compound according to claim 1, wherein both $Z_2$ and $Z_3$ are CH and $Z_4$ is CH or $C(CH_3)$, or one of $Z_2$ and $Z_3$ is N and $Z_4$ is CH.

8. The compound according to claim 1, wherein the methylene substituted with $R_2$ and $R_{17}$ is of S chirality.

9. The compound according to claim 1, wherein X is CONH.

10. The compound of claim 1 wherein X is NHCO.

11. The compound of claim 1 which is

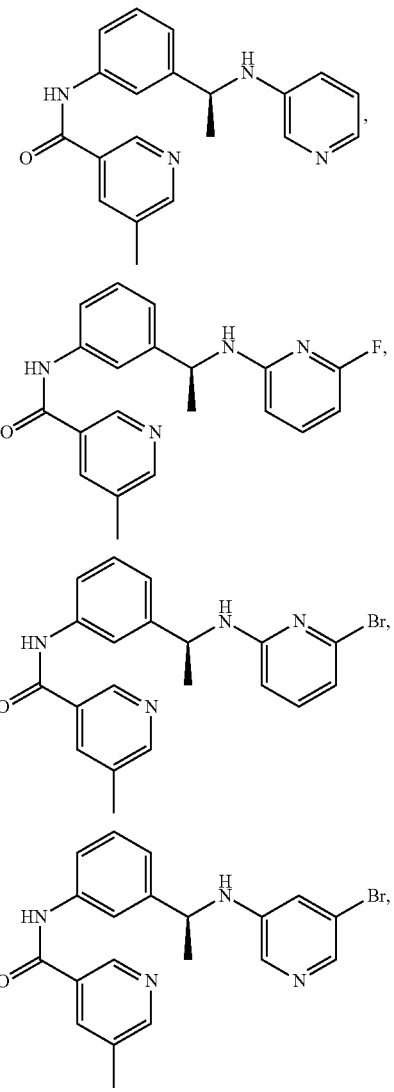

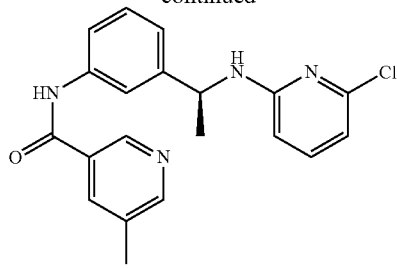

or a pharmaceutically acceptable salt thereof or stereoisomer thereof.

12. A pharmaceutical composition comprising the compound of formula I according to claim 1 and a pharmaceutically acceptable carrier.

13. An implant which comprises the compound of formula I according to claim 1.

14. A method of inhibiting a protein tyrosine kinase in a cell comprising contacting said cell with the compound of formula I according to claim 1.

15. A method for controlling macrophage populations in a subject, comprising contacting said macrophage population with the compound of formula I according to claim 1.

16. A process for the preparation of the compound of formula I according to claim 1, which comprises the step of coupling a compound of formula II:

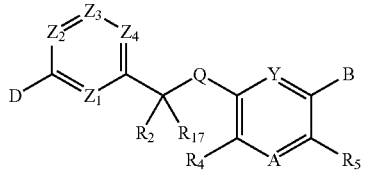

Formula II wherein D is $NH_2$, NHR or $CO_2H$, where R is $C_{1-4}$ alkyl; with WR', wherein W is as defined in claim 1, and R' is $NH_2$, NHR, $CO_2H$ or COCl, where R is $C_{1-4}$ alkyl.

* * * * *